(12) United States Patent
Shetty

(10) Patent No.: US 6,699,989 B1
(45) Date of Patent: Mar. 2, 2004

(54) ANTIVIRAL AND ANTIMICROBIAL GUANIDINE OR BIGUANIDINE DERIVATIVES

(76) Inventor: B. Vithal Shetty, 14438 Long Channel Cir., Germantown, MD (US) 20874

( * ) Notice: Subject to any disclaimer, the term of this patent is extended or adjusted under 35 U.S.C. 154(b) by 0 days.

(21) Appl. No.: 09/649,014

(22) Filed: Aug. 28, 2000

(51) Int. Cl.[7] .................. A61P 31/00; A61K 31/55; A61K 31/495; C07D 487/00; C07D 257/02

(52) U.S. Cl. ............ 540/580; 514/215; 514/224.5; 514/230.2; 514/235.8; 514/252.11; 514/253.04; 514/253.08; 514/300; 514/312; 544/32; 544/73; 544/101; 544/121; 544/279; 544/357; 544/362; 544/363; 546/123; 546/156; 540/474

(58) Field of Search .................. 514/215, 224.5, 514/230.2, 252.11, 300, 312; 540/580; 544/32, 73, 101, 279, 357, 362, 363; 546/123, 156

(56) References Cited

U.S. PATENT DOCUMENTS

| | | | | |
|---|---|---|---|---|
| 4,281,138 A | | 7/1981 | Shetty et al. | 548/306 |
| 4,560,694 A | * | 12/1985 | Oeckl et al. | 514/359 |
| 5,221,693 A | | 6/1993 | Shetty | 514/635 |

OTHER PUBLICATIONS

Hirsch et al., Antiviral Agents, Fields Virology, Third Edition, p. 431, 1996.*

* cited by examiner

*Primary Examiner*—Brenda Coleman
(74) *Attorney, Agent, or Firm*—Rothwell, Figg, Ernst & Manbeck, P.C.

(57) ABSTRACT

Disclosed are guanidine and biguanidine derivatives which have anti-viral and anti-bacterial activity. Also disclosed are pharmaceutical compositions containing such compounds as an active ingredient, and anti-viral and anti-bacterial methods utilizing such compounds.

2 Claims, 4 Drawing Sheets

ANTIVIRAL AND ANTIMICROBIAL GUANIDINE OR BIGUANIDINE DERIVATIVES

STATEMENT REGARDING FEDERALLY SPONSORED RESEARCH OR DEVELOPMENT

This invention was made with governmental support through the National Institutes of Health and the Food and Drug Administration. The United States Government has certain rights in this invention.

CROSS REFERENCES TO RELATED APPLICATIONS

Not applicable.

BACKGROUND OF THE INVENTION

1. Field of the Invention

The present invention relates to guanidine and biguanidine derivatives which are active as anti-viral agents, specifically having anti-HIV activity. Certain compounds have dual mechanisms of action; i.e. they possess as a single molecular structure both anti-HIV and anti-bacterial activities.

2. Description of the Related Art

Quinolones and azaquinolones are well known antibacterial agents which have been commercially available for more than 20 years under various names like Nalidixic acid, ciprofloxacin, ofloxacin, norfloxacin, lomefloxacin, enoxacin, sparfloxacin, pefloxacin and others. The primary use of these agents is to treat bacterial infection. The first quinolone compound was synthesized in 1976 and its mechanism of action was discovered in 1976, Gellert et al. (Proc. Natl. Acad. Sci., U.S.A., 73, 3872 (1976)). The mode of action of the quinolones is through the inhibition of the bacterial DNA gyrase enzyme. This essential enzyme is a bacterial type II topoisomerase which controls DNA topology and assists with DNA replication, repair, decatenation and transcription. The bactericidal nature of quinolones and azaquinolones is due to their potent inhibition of bacterial DNA gyrase, an enzyme which regulates the supercoiling, uncoiling and spatial geometry of bacterial DNA functions that are necessary for controlling DNA replication and repair, transcription and recombination. Quinolones appear to induce a cellular repair mechanism in these same organisms, leading to unbalanced growth and alteration of cellular structure, which results in the death of the bacterial cell.

DNA gyrase is a type 2 topoisomerase, which has 2A subunits and 2B subunits. These subunits are the target proteins for the quinolones. Mammalian topoisomerase II is highly resistant to inhibition by the quinolones and azaquinolones. Furthermore, the eukaryotic enzyme differs from DNA gyrase by structurally and functionally removing, as opposed to inducing, supertwists into DNA. The bacterial gyrase enzyme is approximately 100 times more sensitive to inhibition than the eukaryotic equivalent.

Quinolones have a paradoxical effect of decreased killing at higher drug concentration. This is because of the fact that at high doses, quinolones inhibit RNA synthesis and protein synthesis. This paradoxical effect of quinolones and azaquinolones are important in designing target compounds against the AIDS virus.

Tetraaza macrocyclic ligands ranging from 12 members to 16 members are known in the literature. For example, the preparation of macrocycles (cyclam) are reported by L. Y. Martin, et al., in J. Am. Chem. Soc., 96, 4046 (1974) and J. Am. Chem. Soc. 99, 2968 (1997). Cyclam is also commercially available from Aldrich. The preparation of bis (macrocycles) is reported by Barefield, E. K., et al., in J. Chem. Soc. Chem. Commun., 302–304 (1981) and Cimpolini, M. et al., in Inorg. Chem., 26, 3527–3533 (1987). These broad families of synthetic macrocyclic and bis (macrocyclic) ligands have been studied not only for their complexation properties with metals but also for their antiviral activities. In the present work, these ligands are used as a template for the guanidine and biguanidine derivatives for their dual mechanism of action as anti-HIV and anti-bacterial activities.

The core structure of the AIDS virus is protected by a lipid layer and highly glycosylated protein (gp 160) which endoproteolytically splits into gp 41 and gp 120. The latter protein binds to $CD_4$ of the T lymphocyte and converts the virus RNA into DNA with the help of the enzyme, reverse transcriptase. The highly balanced hydrophilic-hydrophobic site-specific compounds of the present invention possibly penetrate the viral envelope to reach to the core structure of the AIDS virus and thus act as virucidal-bactericidal agents.

The acquired immunodeficiency syndrome (AIDS) is caused by human immunodeficiency virus (HIV) which is also known by several names, namely HIV-1, LAV (lymphadenopathy-associated virus), HTLV-3 (human T-lymphotropic virus type 3) and ARV (AIDS related virus). The genomes of HIV-1 and HIV-2 are only about 50% homologous at the nucleotide level. Yet the two viruses contain the same complement of genes and appear to attack and kill the same human cells by much the same mechanism. In the US, all the AIDS cases are associated with HIV-1 infections. Since the two viruses, HV-1 and HIV-2 share similar biological properties, they have similar mechanism of action. Both HIV-1 and HIV-2 are retroviruses in which the genetic material is RNA rather than DNA. HIV-1 and HIV-2 viruses may not necessarily cause the death of a patient, but they do, in many cases, cause the patient's immune system to be severely depressed. This results in various other diseases (secondary infection or tumor formation) such as various bacterial infections (e.g., pneumocystis carinii pneumonia) herpes, cytomegalovirus, Kaposi Sarcoma and Epstein-Barr virus related lymphomas among others. These secondary infections are generally referred to as opportunistic infections. They are separately treated using other medications. There is thus a great need for drugs which are capable of both treating the underlying HIV infection, as well as secondary opportunistic infections.

SUMMARY OF THE INVENTION

In one aspect, the present invention relates to a compound having one of the following structures:

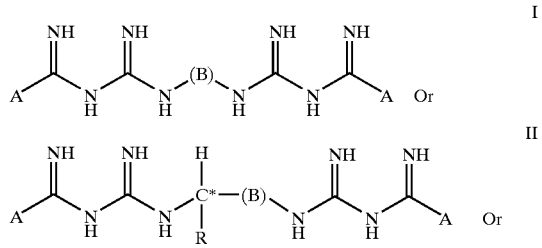

-continued

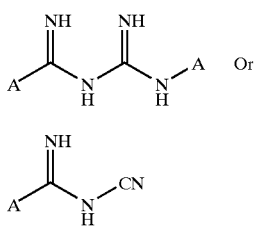

wherein:

a) each A is the same or different, and is selected from the group consisting of i) hydrogen, ii) a nitrile, iii) an amino, iv) an antibacterial agent, v) an antibiotic, vi) a quinolone, vii) an azaquinolone and viii) one of the following groups:

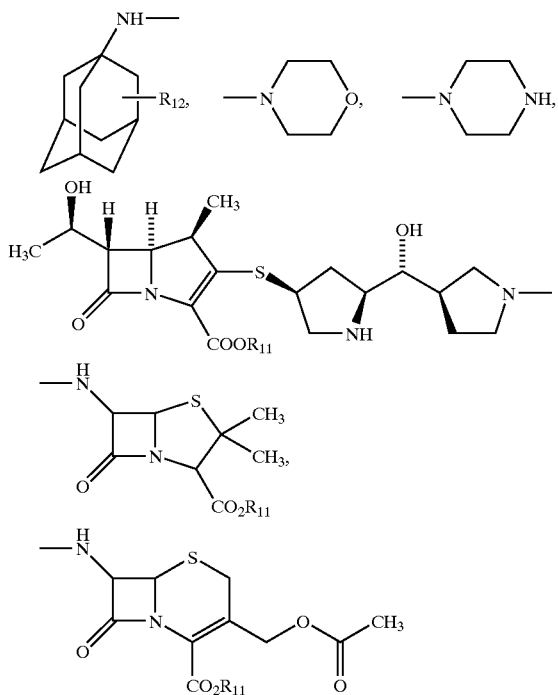

where $R_{12}$ is hydrogen or $C_1$–$C_6$ straight or branched alkyl, and $R_{11}$ is hydrogen, lower alkyl, an aromatic group or a heterocyclic group, with the proviso that with respect to structures I–III, both A's cannot be the adamantane structure above at the same time;

b) B is a straight chain or branched $C_1$–$C_{30}$ alkyl group, which may be interrupted by oxygen, sulfur, optionally substituted aromatic nuclei, sulphoxide, optionally substituted cyclohexane, nitrogen optionally substituted with —NH—C(NH)—NH—C(NH)—A where A is defined above, tris (2-aminoethyl) amine, a heterocycle of the following structure:

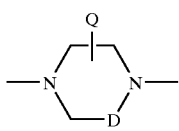

where D is 1–3 carbon atoms and Q is hydrogen, halogen or lower alkyl; or

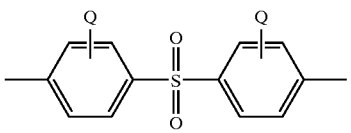

where Q is hydrogen, halogen or lower alkyl; or

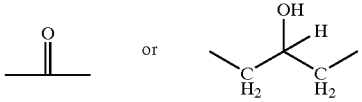

or a hydrophilic moiety; and c) R is hydrogen or $C_1$–$C_6$ straight or branched alkyl;

and pharmaceutically acceptable salts thereof.

In another aspect, the present invention relates to a compound having the following structure:

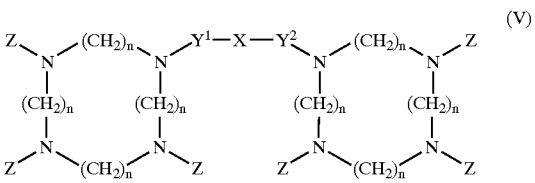

where each n is independently from 1–5;

$Y^1$ and $Y^2$ are the same or different, and are optionally substituted alkyl; optionally substituted aryl; an optionally substituted heterocycle; or a single bond;

X is optionally substituted alkyl; optionally substituted aryl; or an optionally substituted heterocycle; and Z is independently —C(NH)—NH—C(NH)—A, where each A is the same or different, and is selected from the group consisting of i) hydrogen, ii) a nitrile, iii) an amino, iv) an antibacterial agent, v) an antibiotic, vi) a quinolone, vii) an azaquinolone and viii) one of the following groups:

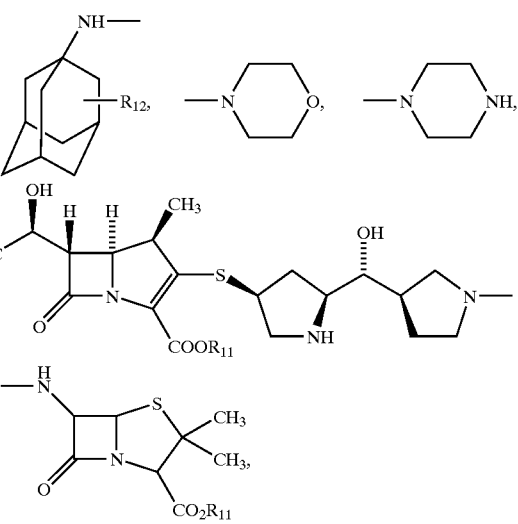

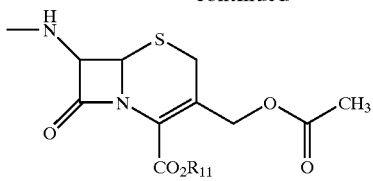

where $R_{12}$ is hydrogen or $C_1$–$C_6$ straight or branched alkyl, and $R_{11}$ is hydrogen, lower alkyl, an aromatic group or a heterocyclic group;

and pharmaceutically acceptable salts thereof.

In another aspect, the present invention relates to a compound having the following structure:

(VI)

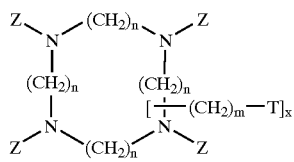

where each n is independently from 1–5;

each m is independently from 0–12;

each Z is independently —C(NH)NH—C(NH)—A, where each A is the same or different, and is selected from the group consisting of i) hydrogen, ii) a nitrile, iii) an amino, iv) an antibacterial agent, v) an antibiotic, vi) a quinolone, vii) an azaquinolone and viii) one of the following groups:

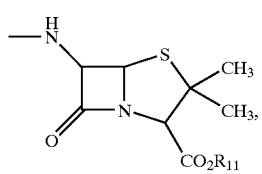

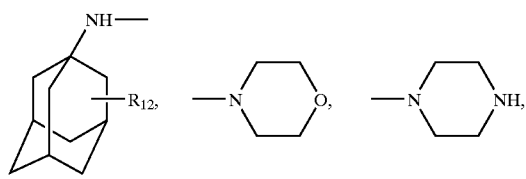

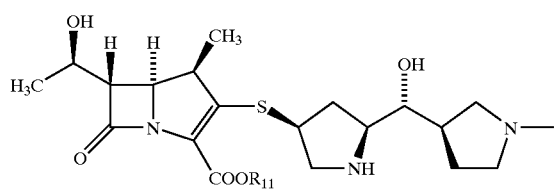

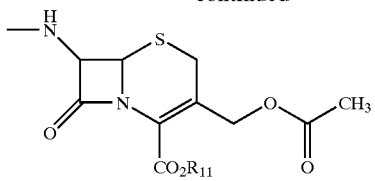

where $R_{12}$ is hydrogen or $C_1$–$C_6$ straight or branched alkyl, and $R_{11}$ is hydrogen, lower alkyl, an aromatic group or a heterocyclic group, T is hydrogen, lower alkyl, optionally substituted aryl or optionally substituted heterocycle; and X is from 0–8.

In another aspect, the present invention relates to a compound having the following structure:

(VII)

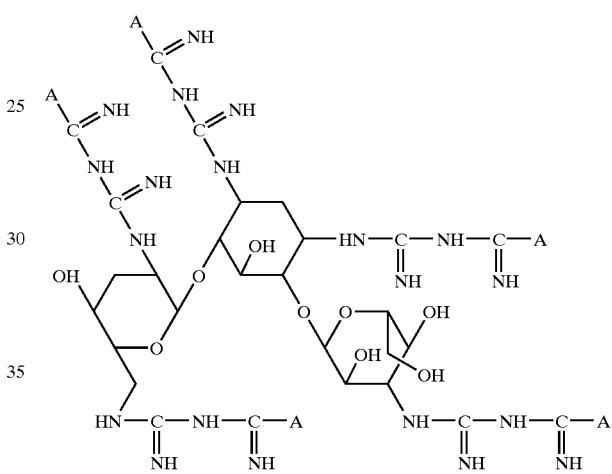

where each A is the same or different, and is selected from the group consisting of i) hydrogen, ii) a nitrile, iii) an amino, iv) an antibacterial agent, v) an antibiotic, vi) a quinolone, vii) an azaquinolone and viii) one of the following groups:

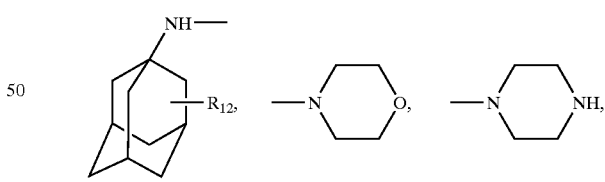

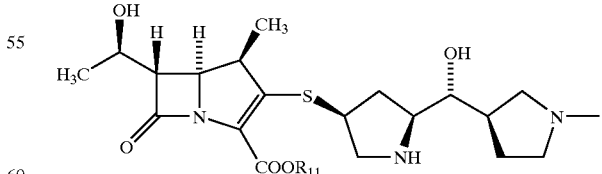

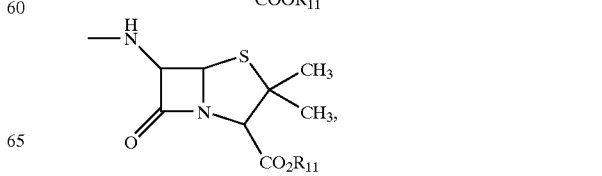

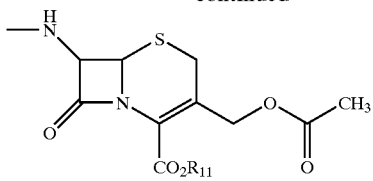

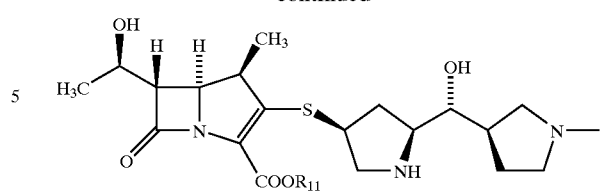

where $R_{12}$ is hydrogen or $C_1$–$C_6$ straight or branched alkyl, and $R_{11}$ is hydrogen, lower alkyl, an aromatic group or a heterocyclic group with the proviso that at least one A is not hydrogen.

In another aspect, the present invention relates to a compound having the following structure:

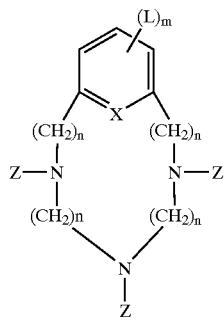

(VIII)

wherein each n is independently from 1–5;

m is from 0–3;

each L is independently hydrogen, lower alkyl, optionally substituted aryl, or nitro;

X is CH or N;

each Z is independently —C(NH)NH—C(NH)—A where each A is the same or different, and is selected from the group consisting of i) hydrogen, ii) a nitrile, iii) an amino, iv) an antibacterial agent, v) an antibiotic, vi) a quinolone, vii) an azaquinolone and viii) one of the following groups:

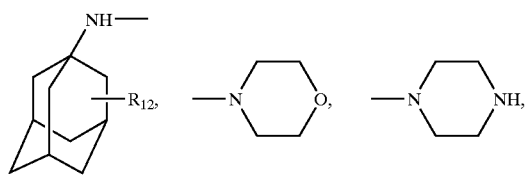

where $R_{12}$ is hydrogen or $C_1$–$C_6$ straight or branched alkyl, and $R_{11}$ is hydrogen, lower alkyl, an aromatic group or a heterocyclic group.

In another aspect, the present invention relates to a compound having the following structure:

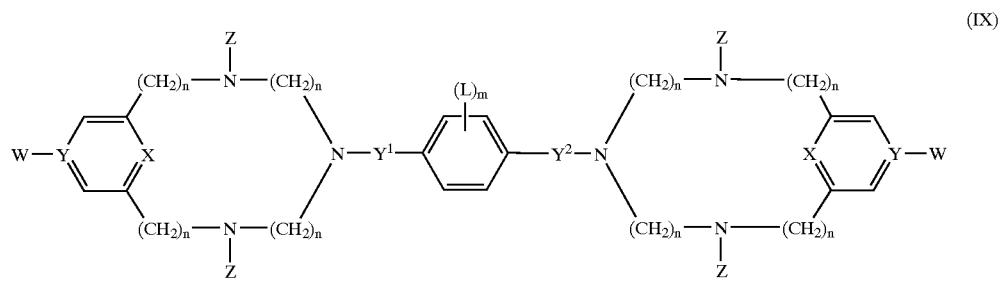

(IX)

where m is from 0–4;

each L is independently hydrogen, halogen, alkyl, aryl or nitro;

each W is independently hydrogen, halogen, alkyl, alkoxy, or aryl;

X and Y are each independently CH or N;

$Y^1$ and $Y^2$ are each independently optionally substituted alkyl or a single bond; and each Z is independently —C(NH)—NH—C(NH)—A, where each A is the same or different, and is selected from the group consisting of i) hydrogen, ii) a nitrile, iii) an amino, iv) an antibacterial agent, v) an antibiotic, vi) a quinolone, vii) an azaquinolone, and viii) one of the following groups:

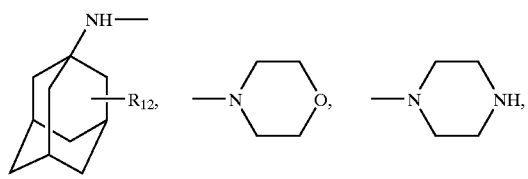

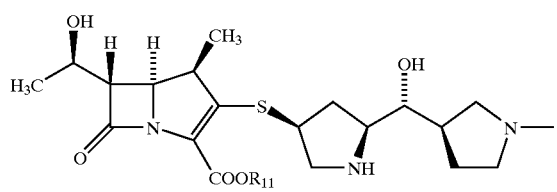

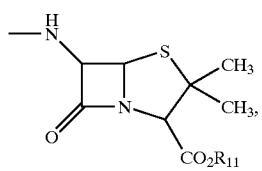

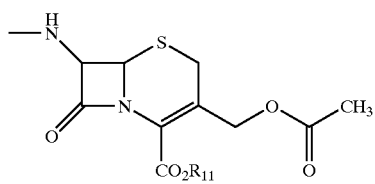

where $R_{12}$ is hydrogen or $C_1$–$C_6$ straight or branched alkyl, and $R_{11}$ is hydrogen, lowere alkyl, an aromatic group or a heterocyclic group;

and pharmaceutically acceptable salts thereof

In another aspect, the present invention relates to an antiviral composition which comprises:
a) an effective amount of a compound described above; and
b) a pharmaceutically acceptable carrier.

In another aspect, the present invention relates to an antibacterial composition which comprises:
a) an effective amount of a compound described above; and
b) a pharmaceutically acceptable carrier.

In another aspect, the present invention relates to an antiviral and antibacterial composition which comprises:
a) an effective amount of a compound described above; and
b) a pharmaceutically acceptable carrier.

In another aspect, the present invention relates to a method for preventing or treating a bacterial infection in a mammalian host, said method comprising administering to a mammal in need thereof an effective amount of a compound described above.

In another aspect, the present invention relates to a method for preventing or treating a viral infection in a mammalian host, said method comprising administering to a mammal in need thereof an effective amount of a compound described above.

In another aspect, the present invention relates to a method for preventing or treating a viral infection and an opportunistic bacterial infection in a mammalian host, said method comprising administering to a mammal in need thereof an effective amount of a compound described above.

In another aspect, the present invention relates to compounds useful in the synthesis of the compounds of structure (v) above, and which compounds have the following structure:

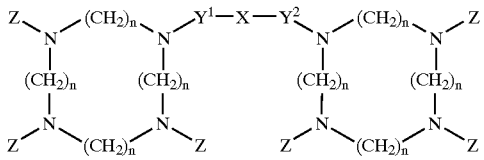

where each n is independently from 1–5;

$Y^1$ and $Y^2$ are the same or different, and are optionally substituted alkyl; optionally substituted aryl; an optionally substituted heterocycle; or a single bond;

X is optionally substituted alkyl; optionally substituted aryl; or an optionally substituted heterocycle; and each Z is independently —C(NH)—NH—CN or —(CH$_2$)$_m$—NH—C(NH)—NH—CN where m is from 1 to 6.

In another aspect, the present invention relates to compounds useful in the synthesis of the compounds of structure (VI) above, which compounds have the following structure:

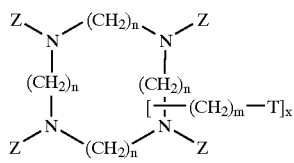

where each n is independently from 1–5;
each m is independently from 0–12;
each Z is independently —C(NH)—NH—CN or —(CH$_2$)$_q$—NH—C(NH)—NH—CN where q is from 1 to 6, and T is hydrogen, lower alkyl optionally substituted aryl or an optionally substituted heterocycle; and X is from 0–8.

DETAILED DESCRIPTION OF THE INVENTION

Figure 1:
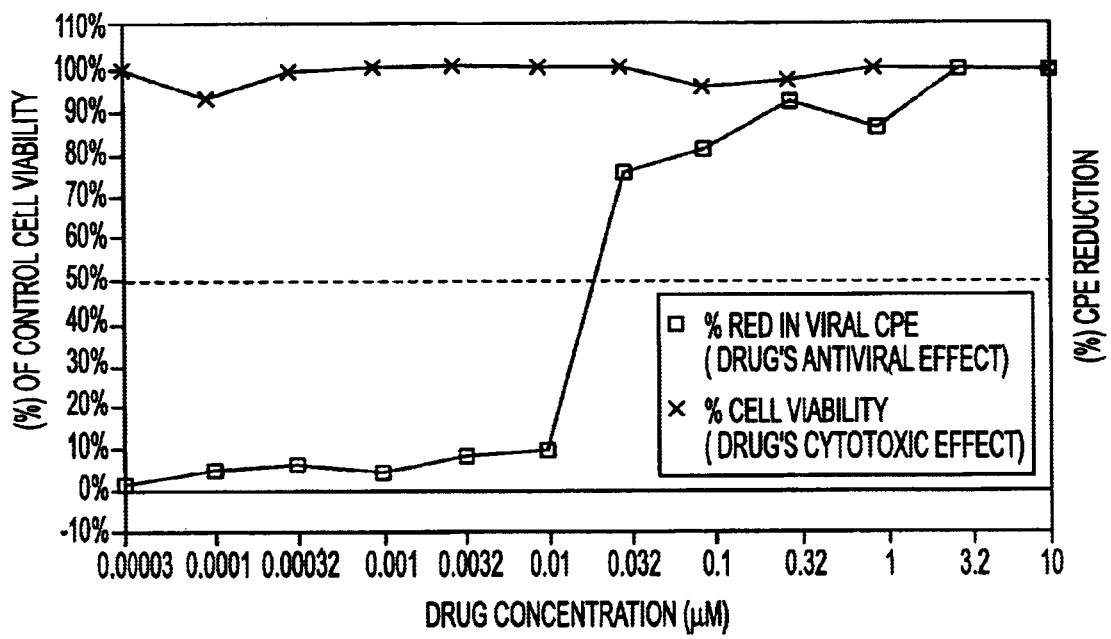
FIG. 1 is a graph depicting the antiviral activity of a prior art compound.
Figure 2:
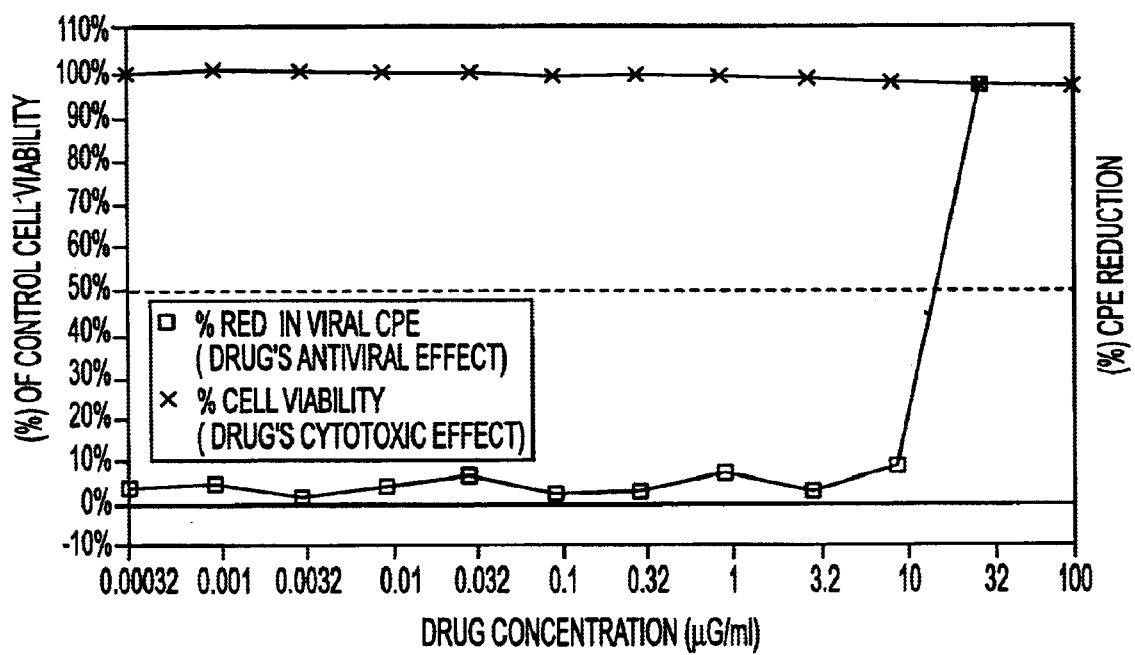
FIG. 2 is a graph depicting the antiviral activity of a compound of the present invention.
Figure 3:
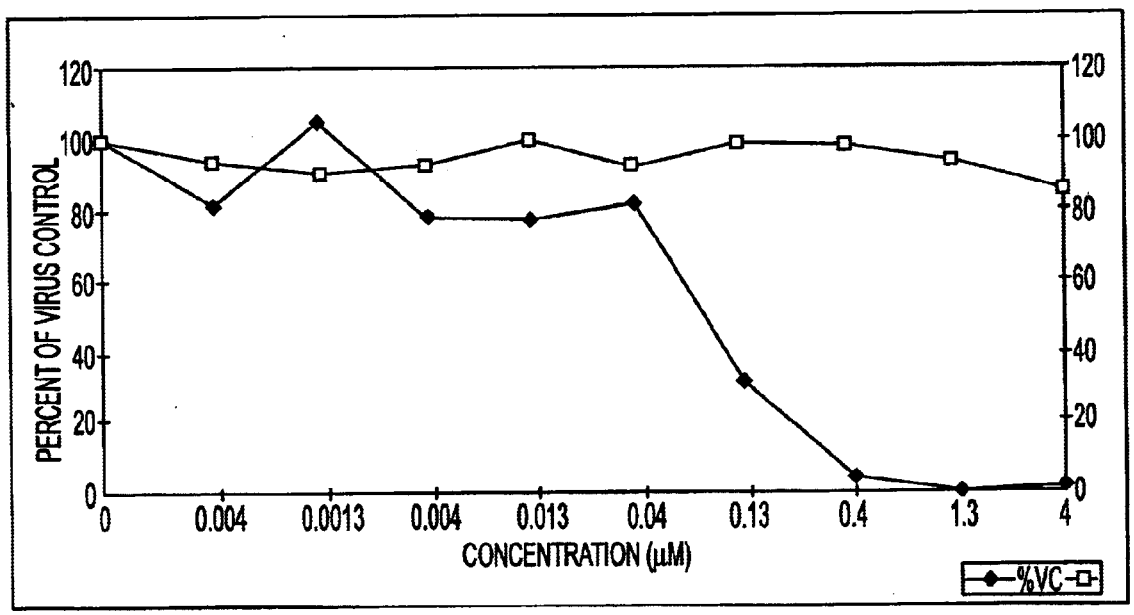
FIG. 3 is a graph depicting the antiviral activity of a prior art compound.
Figure 4:
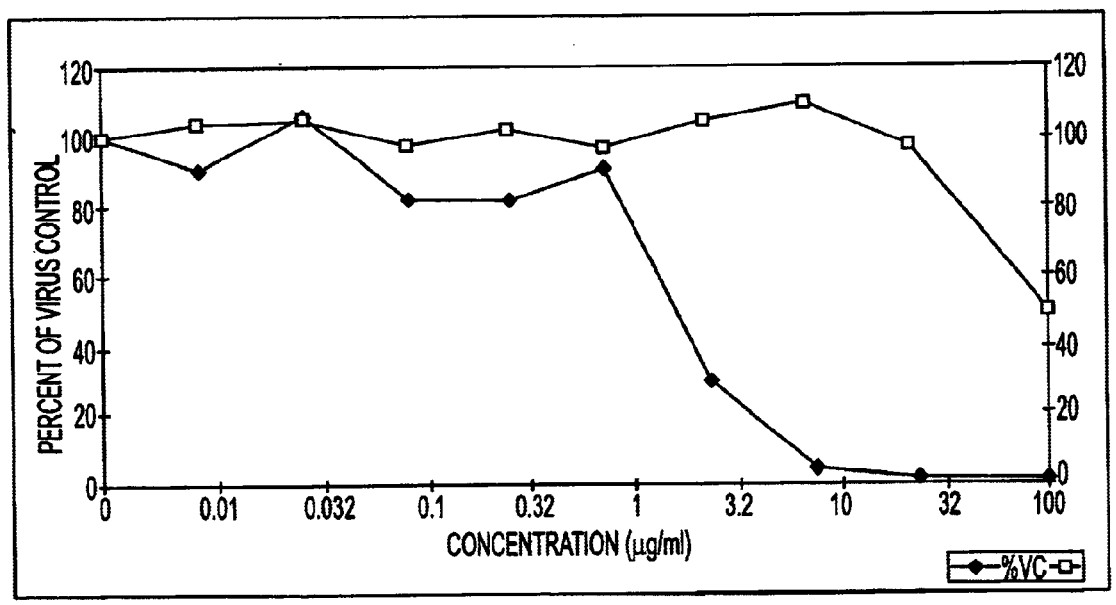
FIG. 4 is a graph depicting the antiviral activity of a compound of the present invention.

It has now been discovered that the compounds of this invention have dual mechanism of anti-HIV and antibacterial action. For example the compound known as "BVS-10A" having the formula:

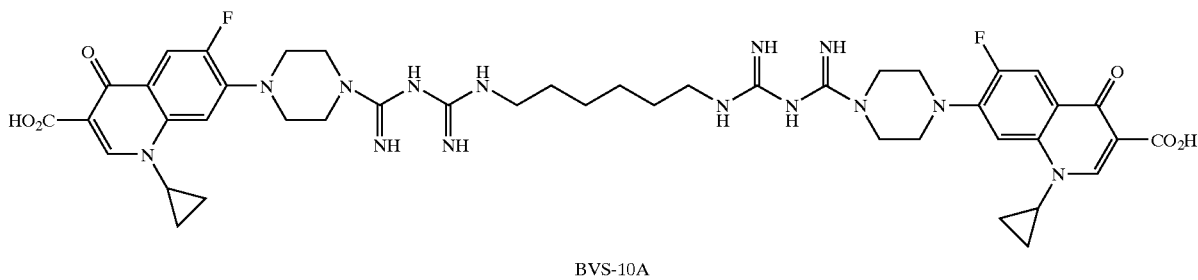

BVS-10A was found to have dual anti-HIV and antibacterial activity. The compound and its derivatives have the advantage of treating not only humans identified as having AIDS as well as humans identified as infected by or carrying the AIDS virus to prevent or inhibit the acquired immunodeficiency syndrome, but also to prevent or inhibit opportunistic infections. It is recognized that in AIDS patients, there is an imbalance in the two basic types of immune system cells, namely helper/inducer T lymphocytes, with the ratio of suppressor cells to helper/inducer cells greatly elevated. It was shown that the imbalance is caused by depletion of the helper/inducer T cells. When the patient is treated with the "BVS-10" compound or its derivatives, it is possible that the number of helper T cells, T cells and platelets may increase over those before treatment.

The bifunctional compounds of the present invention exhibit a broadened antiviral and antibacterial spectrum of activity reflecting both quinolone, azaquinoline, (aza)quinolone-cyclam, (aza)quinolone-bicyclam and biguanidine or guanidine contribution, and suggestive of a dual mode of action. The beneficial influence of quaternary nitrogen substituents on the biological activity has been noted by the potency of the molecule against both AIDS virus and bacteria. The activity may involve the transportation, RNA and intracellular inactivation and inhibition of the essential enzymes reverse transcriptase and DNA gyrase. The invention relates to a method of treating AIDS virus in warm-blooded animals with the antiviral composition or antibacterial composition containing the compounds of the invention. More particularly, the invention comprehends an antiviral composition containing the new compounds and at least one pharmaceutically acceptable carrier used to treat warm blooded animals infected with (or to prevent infection with) viruses and bacteria, particularly the AIDS virus known as human immunodeficiency virus (HIV).

The present invention relates to a new class of compounds containing both hydrophilic and lipophilic regions. The basic structure may be represented by the general formulae given above, where the various substituents are as defined.

In certain preferred embodiments, the "A" substituent is a quinolone or azaquinolone antibacterial moiety such as:

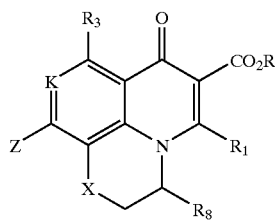

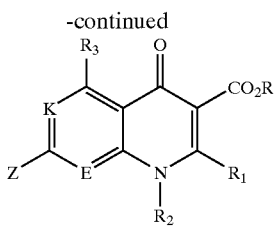

-continued

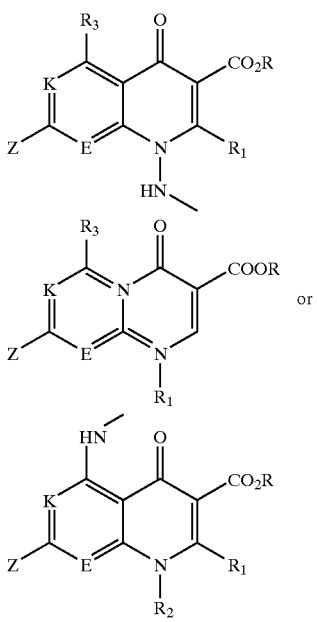

where Z is one or more heterocyclic rings containing at least one N atom
or

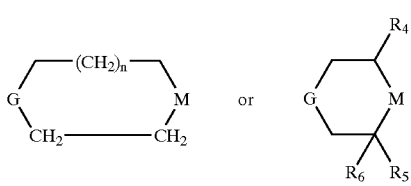

which may be attached to the structure above through any available point of attachment;

where n is 0 to 3; $R_4$, $R_5$ and $R_6$ are each independently hydrogen or lower alkyl or alkylene; G and M are independently O, S or $NR_{10}$; where $R_{10}$ is hydrogen, —C(N)—NH—CN, halogen, a single bond, or lower alkyl or alkylene;

E is nitrogen or $CR_{10}$, where $R_{10}$ is hydrogen or halogen;

K is nitrogen or $CR_7$, where $R_7$ is hydrogen, nitro, halogen, nitrile, carboxamide, carboxyl or an ester;

R is hydrogen or lower alkyl;

R$_1$ is hydrogen, a lower arylalkyl group having 1–6 carbon atoms, an alkyl group having 1–4 carbon atoms in the aliphatic part and 6 to 10 carbon atoms in the aromatic part, or an aryl group having 6 to 10 carbon atoms;

R$_2$ is an alkyl group having one to six carbon atoms; a cycloalkyl group having 3 to 7 carbon atoms optionally substituted with halogen; 2,4-difluorophenyl or 2- or 4-fluorophenyl; amino; lower alkylamino; propylamino; N-formyl-lower alkylamino or di-lower-alkylamino; a vinyl group; a 2-fluoroethyl group; a haloalkyl group or a 2-hydroxylkyl group; phenyl or substituted phenyl wherein the phenyl ring is substituted with one or two or three substituents independently selected from C$_1$ to C$_6$ alkyl, halogen, methylenedioxy and hydroxy; alkoxy or trifluoromethyl; 2-, 3-, or 4-pyridine; 2- or 3-thiophene; 2-imidazole; 2-oxazole or 2-thiazole; a pyridyl or adamantyl group; or a benzoxazine group;

R$_3$ is a hydrogen, amino, substituted amino, halogen or a lower alkyl group;

R$_8$ is hydrogen or lower alkyl; and X is methylene, O, S or NR$_9$, here R$_9$ is hydrogen or lower alkyl.

More specifically, the Z substituent may include

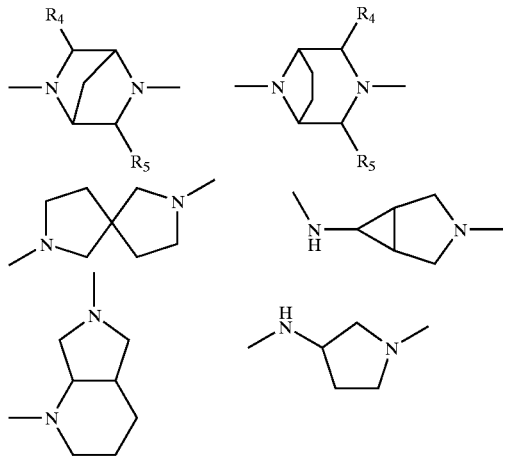

where R$_4$ and R$_5$ are independently hydrogen or lower alkyl.

It will be readily appreciated from the structures above that certain compounds of the present invention may exist as optically active forms. The pure D-isomer, pure L-isomer as well as mixtures thereof, including the racemic mixtures, are contemplated by the invention. Additional asymmetric carbon atoms may be present in a substituent such as in an alkyl group, piperazine or benzoxazine moiety. All such isomers as well as mixtures thereof are intended to be included in the invention.

The term haloalkyl group under the definition of R$_2$ above is intended to include halogen substituted straight and branched carbon chains of two to six carbon atoms. Those skilled in the art will recognize that the halogen substituent may not be present on the 2-carbon atom of the chain. Representative of such groups are β-chloroethyl, β-dichloroethyl, β-chloropropyl, β-chloro-2-propyl, α-iodobutyl, β-fluoroethyl, β-difluoroethyl, and the like the term halogen is intended to include, fluorine, chlorine, bromine and iodine unless otherwise specified.

The present invention also includes the salts of the compounds described above. Such salts may be derived from inorganic acids such as hydrochloric acid, or phosphoric acid; from organic acids such as acetic acid, lactic acid, oxalic acid, succinic acid, methane sulfonic acid, maleic acid, malonic acid or gluconic acid; from acidic amino acids such as aspartic acid or glutamic acid; metal (e.g. sodium, potassium, calcium, magnesium or zinc) salts; from organic bases such as N, N-dibenzyl ethylene diamine, dimethylamine, triethylamine, dicyclohexylamine, benzylamine or ethylene diamine, and from basic amino acids such as lysine or arginine.

The esters of the compound of the formula represented by A include not only substituted or unsubstituted aliphatic esters especially lower alkyl esters such as methyl or ethyl esters but also esters that can be at least partially converted to the compound A of structure I, II, III or IV by chemical hydrolysis or by enzymatic hydrolysis in vivo such as acetoxymethyl esters, pivaloyloxymethyl esters, ethoxycarbonyloxy ethyl esters, choline esters, aminoethyl esters (e.g. dimethylaminoethyl or 1-piperidinylethylesters), 5-indanyl esters, phthalidyl esters and hydroxyalkyl esters (e.g. hydroxyethyl or 2,3-dihydroxypropyl esters).

The term "lower" means that the groups or compounds so qualified have not more than 6, preferably not more than 4 carbon atoms. The compounds of the specific structures shown above, and esters and salts of these compounds will, therefore, be generally referred to herein as the compounds of the invention. The compounds of the invention may also exist as hydrates, clathrates, which are also included in the compounds of this invention. The compounds of the invention include those, which have asymmetric carbon atoms on the piperazine, pyrrolidine or homopiperazine ring at the 7-position or at 1,4-benzoxazine ring or at the dimeric alkyl chain interposed between the two biguanidine chains and therefore exists in optically active forms. Hence, D-isomers, L-isomers and mixtures thereof all included in the compounds of this invention. The compounds of this invention may have two asymmetric carbon atoms simultaneously and therefore can exist as stereoisomers having different configurations (cis or trans form). These stereoisomers and their mixtures are also included within the compounds of this invention.

As noted above, compounds within the present invention have antiviral and antibacterial activity and thus may be administered to patients in need thereof. For therapeutic or prophylactic treatment, the compounds of the present invention may be formulated in a pharmaceutical composition, which may include, in addition to an effective amount of active ingredient, pharmaceutically acceptable carriers, thickeners, diluents, buffers, preservatives, surface active agents and the like. Pharmaceutical compositions may also include one or more other active ingredients if necessary or desirable.

The pharmaceutical compositions of the present invention may be administered in a number of ways as will be apparent to one of ordinary skill. Administration may be done topically, orally, rectally, nasally, vaginally, by inhalation, or parenterally (including subcutaneous, intramuscular, intravenous and intradermal), for example.

Topical formulations may include ointments, lotions, creams, gels, drops, suppositories, sprays, liquids and powders. Oral formulations include powders, granules, suspensions or solutions in water or non-aqueous media, capsules or tablets, for example. Thickeners, flavorings, diluents, emulsifiers, dispersing aids or binders may be used as needed.

Parenteral formulations may include sterile aqueous solutions which may also contain buffers, diluents and other suitable additives.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved. One of ordinary skill may readily determine optimum dosages, dosing methodologies and repetition rates. In general, it is contemplated that unit dosage form compositions according to the present invention will contain from about 0.01 mg to about 500 mg of active ingredient, preferably about 0.1 mg to about 10 mg of active ingredient. Topical formulations (such as creams, lotions, solutions, etc.) may have a concentration of active ingredient of from about 0.1% to about 50%, preferably from about 0.1% to about 10%. However, final strength of the finished dosage form will depend on the factors listed above and may be readily determined by one of ordinary skill.

The compounds of the present invention may be synthesized according to the following general reaction schemes:

A. GENERAL REACTION SCHEME

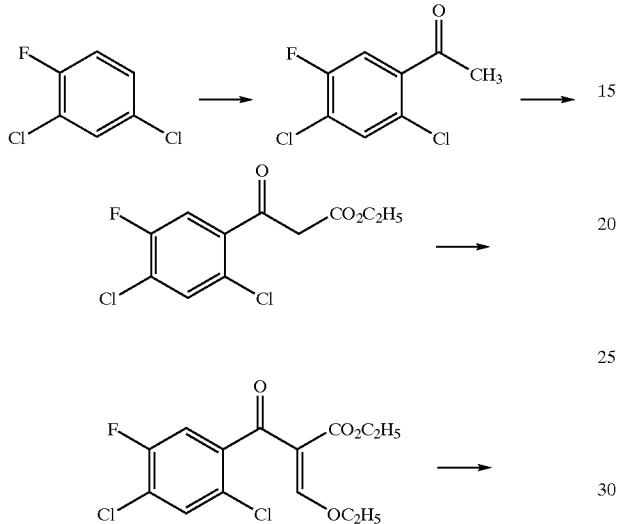

J. Med. Chem. 1985, 28, 1558–1564

B. GENERAL REACTION SCHEME

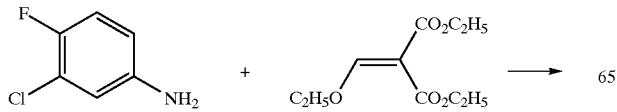

-continued

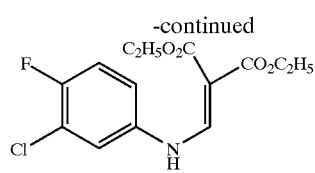

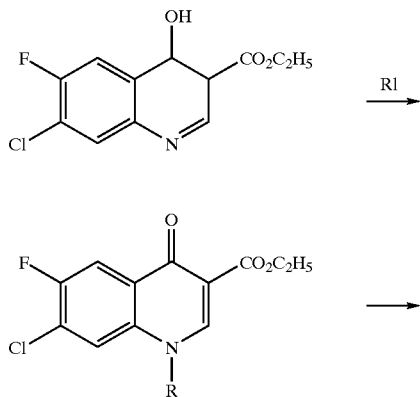

J. Med. Chem. 1985, 23, 1358

C. GENERAL REACTION SCHEME

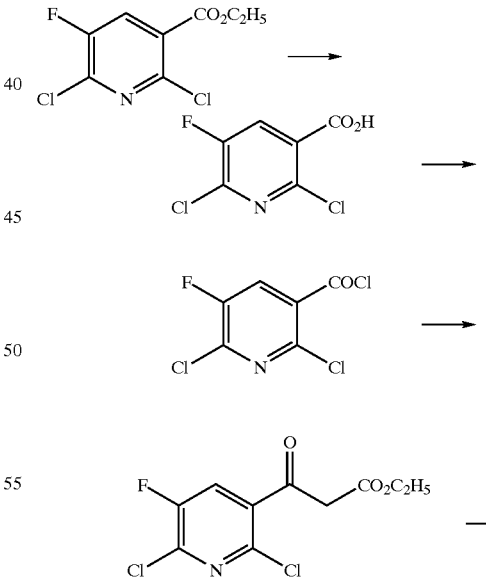

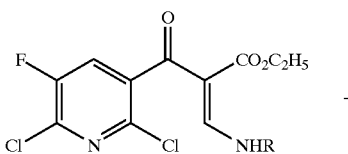

17
-continued
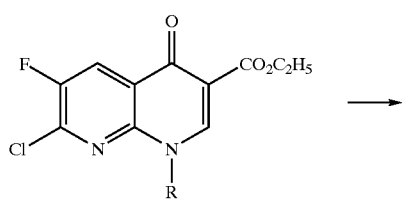
18
-continued
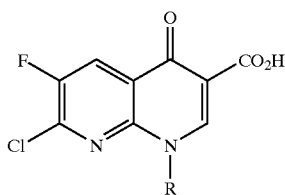
J. Med. Chem. 1986, 29, 2363–2369
D. GENERAL REACTION SCHEME
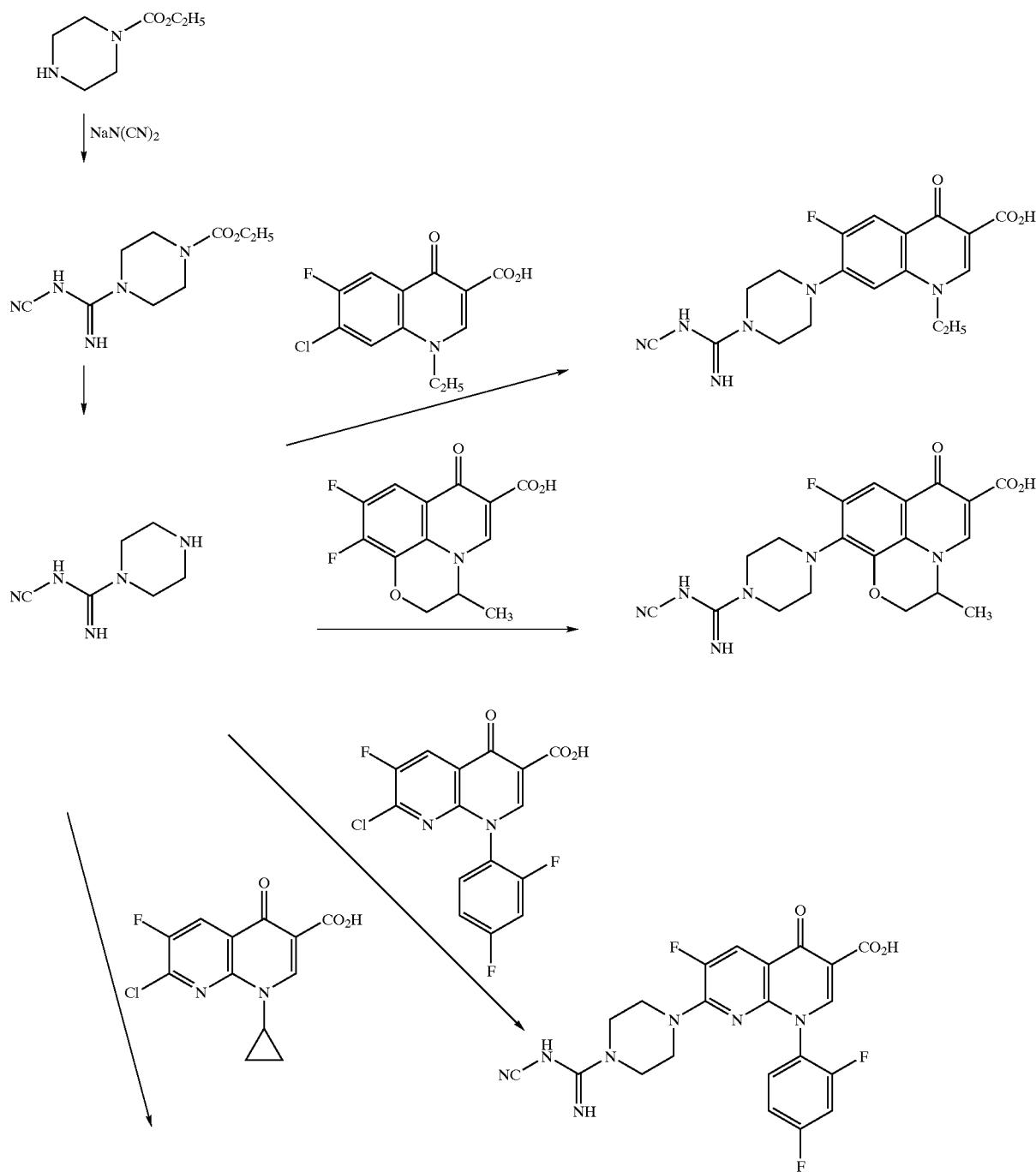

-continued
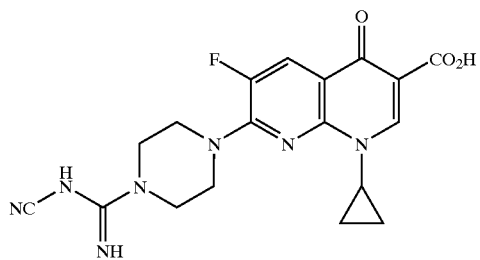
E. GENERAL REACTION SCHEME
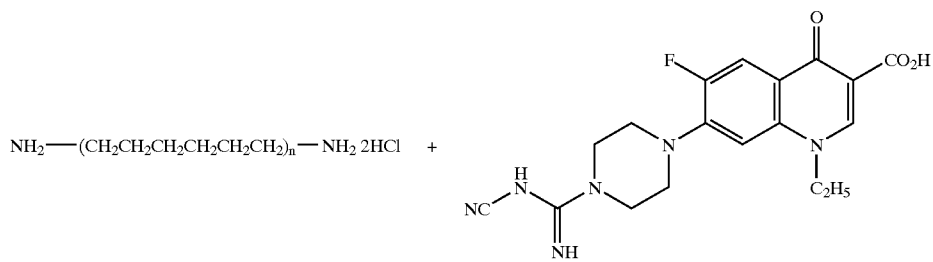
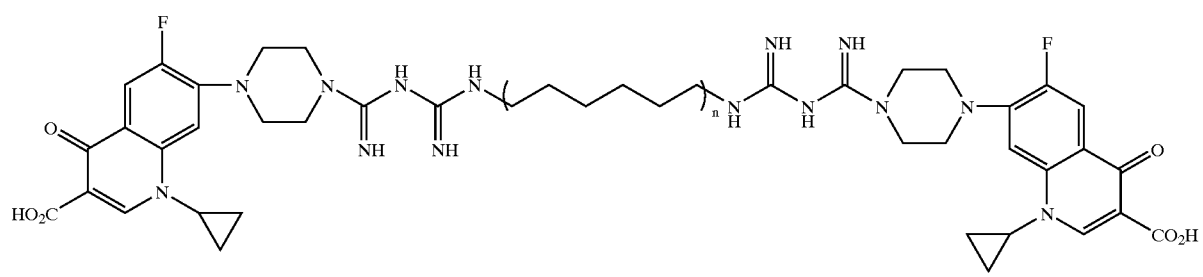
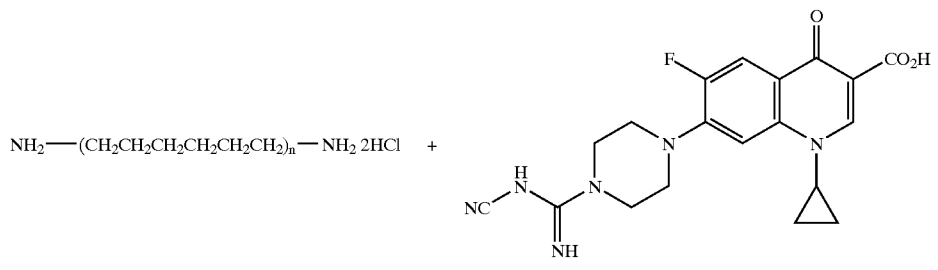
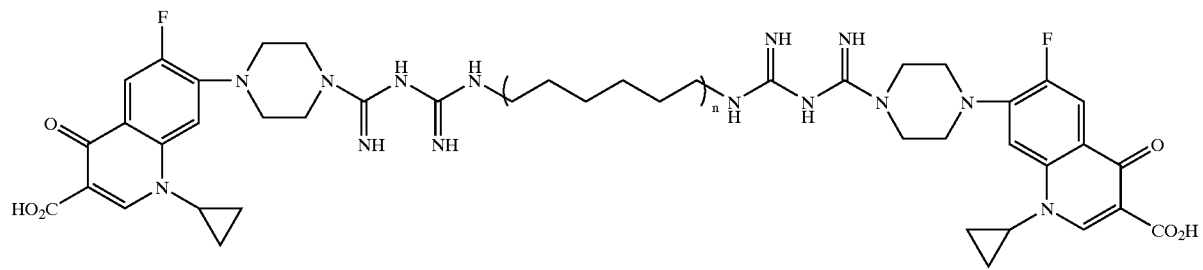

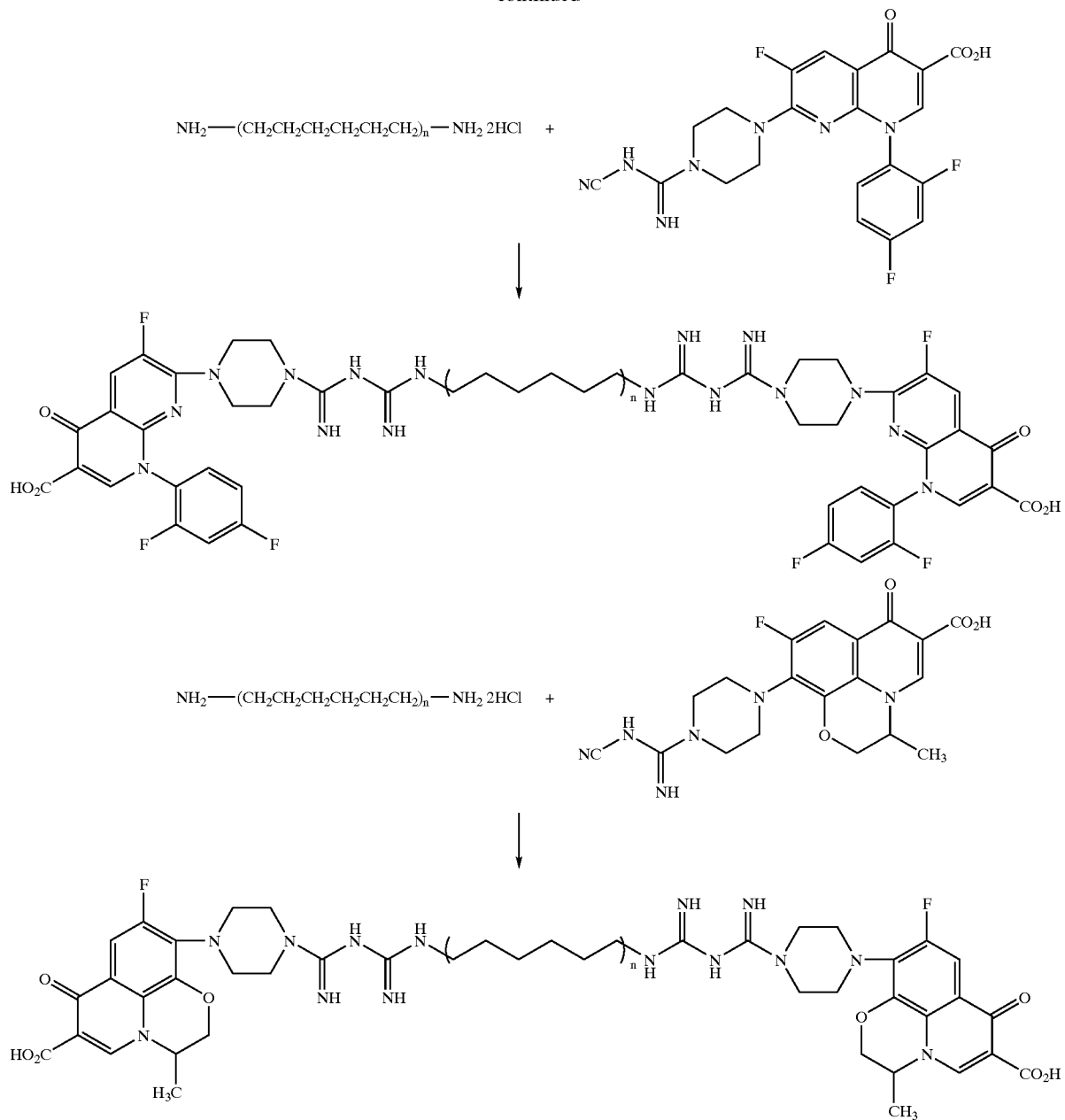
The compounds of this invention of the formula (I), (II), (III) or (IV) can be prepared by various alternative procedures. Some of the starting compounds in the reaction scheme are known in the literature. They have been noted. Following are some specific reaction schemes for their preparation.
SPECIFIC REACTION SCHEME-I
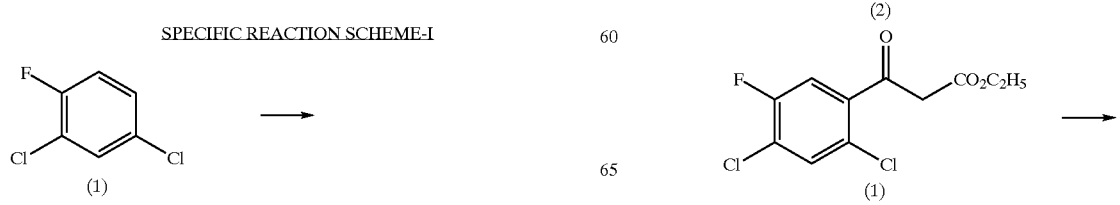

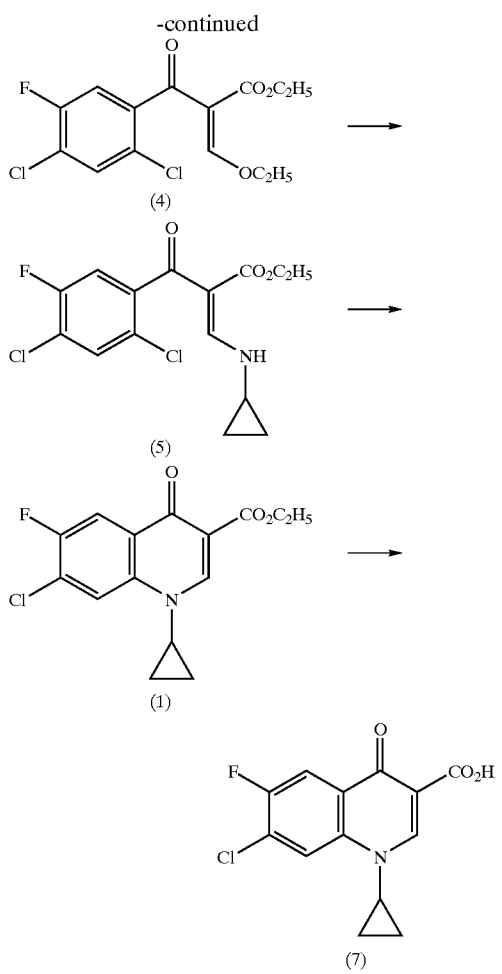

2,4-Dichloro-5-fluoroacetophenone (2)

To a warm solution of 1,3-dichloro4-fluorobenzene at 70° C. (175.0 gm), anhydrous aluminum chloride was added in small portion with stirring (260.0 g). Then acetic anhydride was added in small portion with stirring (125 mL) followed by an additional amount of aluminum chloride (159.0 g). The temperature was slowly raised to 120° C. with stirring for 25 hours. The thick reaction mixture was cooled and poured into 400 cc of concentrated hydrochloric acid containing ice. The oil was extracted with methylene chloride, washed with water, dried over anhydrous magnesium sulfate and concentrated to give 165.0 g of oil (2).

Ethyl 2,4-Dichloro-5-fluorobenzoyl acetate (3)

To a mixture of 60% sodium hydride dispersion powder (66.0 g) in tetrahydro furan (330 mL) under a blanket of nitrogen, diethyl carbonate was added (680 mL). The mixture was heated to 45° C. with stirring and a solution of 2,4-dichloro-5-fluoro acetophenone (2) (165.0 g) in diethyl carbonate (130 mL) was added to it maintaining the temperature between 50° C.–55° C. for 5 hours. It was concentrated under reduced pressure, mixed with dichloromethane (500 mL) and treated with glacial acetic acid (240 mL) in water (2.7 L). The combined methylene chloride extract was washed with sodium bicarbonate (66.0 g) in water (1 L). It was dried over anhydrous magnesium sulfate and concentrated to give 215.0 g oil (3). It was used for next step without further purification.

2,4-Dichloro-alpha(ethoxymethylene)-5-fluoro-beta-oxo-benzene propanoic acid ethyl ester (4)

A mixture of triethyl orthoformate (209 mL), acetic anhydride (350 mL) and (3) (215.0 g) was refluxed with stirring under nitrogen for 6 hours while collecting most of ethyl acetate. The solution was concentrated to give 226.0 g. of oil (4).

7-Chloro-6-fluoro-1-cyclopropyl-1,4-dihydro-4-oxo-quinoline-3-carboxylic acid (7)

To a solution of 4 (80 g) in methylene chloride (800 mL), cyclopropylamine (44.0 g) was added with cooling below 10° C. The mixture was stirred at room temperature for 1 h and evaporated to a dry mixture. To the dry mixture in dimethoxyethane (800 mL), a 60% sodium hydride-in-oil suspension (12.0 g) was added slowly with cooling and stirring. The mixture was heated at 80–85° C. for 3 h under nitrogen atmosphere. It was cooled and water (5 L) was added and the precipitate was filtered and washed with water and dried. The ester was suspended in tetrahydrofuran (800 mL). A solution of sodium hydroxide (20.0 g) in water (500 mL) was added and the mixture was refluxed for 2 h. It was cooled and acidified with acetic acid and the precipitate was filtered. The solid was washed with water and acetone. wt=19.0 g of (7). m.p.=235–240° C.

Anal. calcd. for: $C_{13}H_9NFClO_3$. Theory: C, 55.43; H, 3.22; N, 4.97; F, 6.77; Cl, 12.58. Found: C, 55.42; H, 3.26; N, 4.95; F, 5.92; Cl, 12.31.

SPECIFIC REACTION SCHEME-II

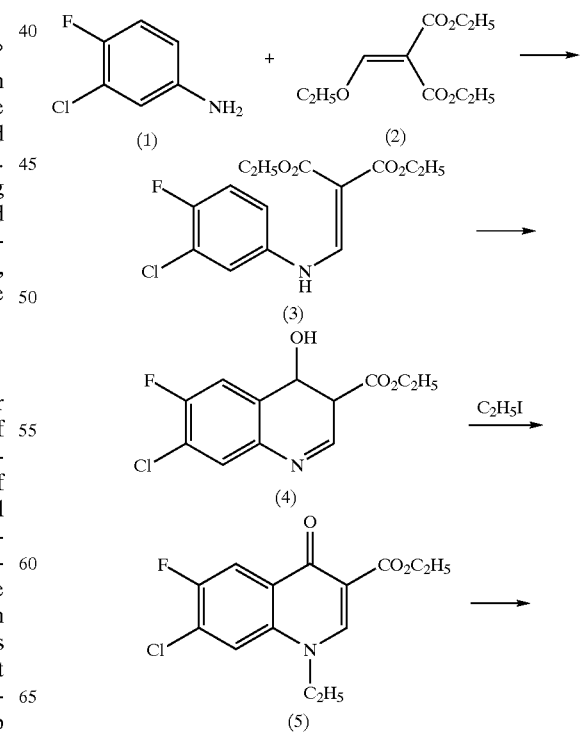

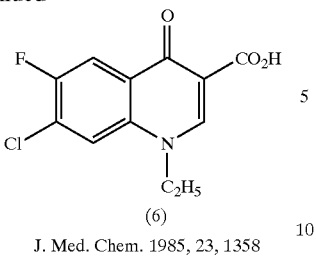

J. Med. Chem. 1985, 23, 1358

7-Chloro-6-fluoro-4-hydroxyquinoline-3-carboxylic acid ethyl ester (4)

A mixture of 3-chloro-4-fluoroaniline (1) (87.3 g) and diethyl ethoxymethylene malonate (129.7 g) and Dowtherm (700 mL) (diphenyl ether) was refluxed for 4 h. It was cooled and the resulting solid was removed by filtration. The solid was recrystallized from DMF to give 55.0 g (4). m.p.= >300° C.

Anal. Calcd for $C_{12}H_9NFClO_3$

| Theory: | C | H | N | F | Cl |
|---|---|---|---|---|---|
|  | 53.45 | 3.36 | 5.19 | 7.04 | 13.14 |
| Found: | 53.45 | 3.48 | 5.26 | 6.53 | 12.67 |

7-Chloro-1-ethyl-6-fluoro-1,4-dihydro-4-oxoquinoline-3-carboxylic acid (6)

A mixture of 7-chloro-6-fluoro-4-hydroxyquinoline-3-carboxylic acid ethyl ester (4) (55.0 g), anhydrous potassium carbonate (8.0 g) and DMF (150 mL) was heated with stirring at 125° C. for 3 h. It was cooled to 70° C. and ethyl iodide (19.0 g) was added and continued heating at 120° C. for 4 h. The mixture was evaporated to dryness, extracted, with $CH_2Cl_2$, washed with water, dried and evaporated to dryness. The crude ester was recrystallized from EtOH to yield (5) m.p.=142–143° C. wt=50.0 g. The ester (5) was mixed with 2N NaOH (700 mL) and refluxed with stirring for 2 h. It was cooled acidified with AcOH and the resulting precipitate was filtered off, washed with water and dried. The solid was recrystallized from DMF to yield (6)=18.0 g., m.p. 284–285° C.

SPECIFIC REACTION SCHEME-III

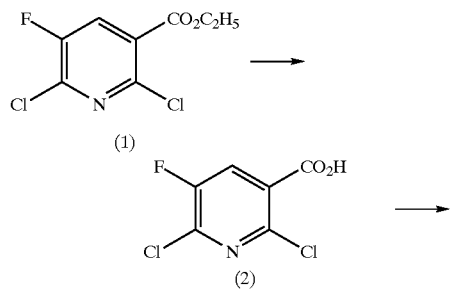

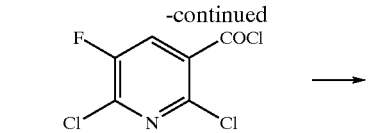

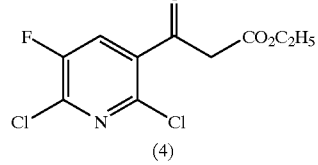

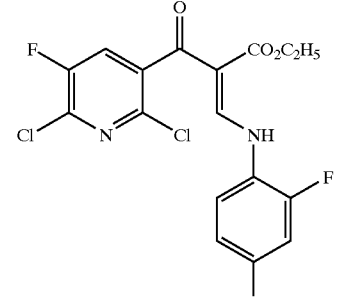

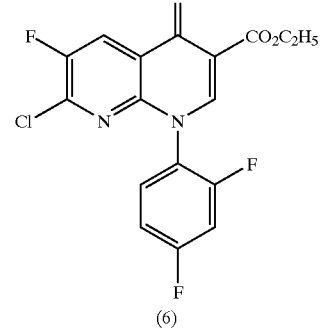

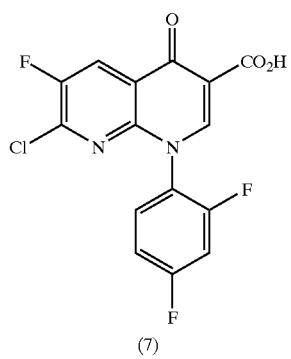

J. Med. Chem. 1986, 29, 2363–2369

2,6-Dichloro-5-fluoronicotinic acid (2)

Ethyl 2,6-dichloro-5-fluoronicotinate (1) (30.0 g) was dissolved in a mixture of 60 mL of trifluoro acetic acid and 60 mL of 7.5 N HCl. The mixture was refluxed with stirring for 26 h. It was cooled and the trifluoroacetic acid was removed under reduced pressure. The solution was mixed with 150 mL water, the resulting precipitate was filtered, washed with hexane and dried to yield 16.5 g of 2,6-dichloro-5-fluoro nicotinic acid (2). m.p.=152–156° C.

Ethyl 2,6-dichloro-5-fluoronicotinylacetate (4)

2,6-Dichloro-5-fluoronicotinic acid (2) (14 g) was dissolved in thionyl chloride (70 mL). The mixture was heated at 85° C. with stirring for 2.5 h and the thionyl chloride was removed under reduced pressure, yielding a yellowish oil, 2,6-dichloro-5-fluoronicotinyl chloride (3). Monoethyl malonate (27 g) and 6 mg of biquinoline was dissolved in 560 mL of dry THF and cooled to −30° C. A solution of 2.5 M of n-butyllithium in hexane was added until a pink color remained at −5° C. (160 mL). The suspension was then cooled to −50° C. The acid chloride obtained as described above, dissolved in 50 mL THF was then added to the suspension dropwise with stirring. The dry ice bath was removed and the reaction mixture was stirred at room temperature for 1 h. The reaction was acidified with 400 mL of 1N HCl and was extracted with ether. It was washed with aqueous sodium bicarbonate solution and water. The ether solution was dried, evaporated to dryness and washed with hexane to give 27 g of (4). m.p=63–66° C.

Ethyl-3,1-(2,4-Difluoroanilino)-2-(2,6-dichloro-5-fluoronicotinvl) acrylate (5)

A solution of ethyl 2,6-dichloro-5-fluoro nicotinylacetate (4) (8 g) in triethyl orthoformate (7 mL) and acetic anhydride (50 mL) was heated at 130° C. for 1 h with removal of ethyl acetate formed during the reaction. The solution was evaporated under reduced pressure to give mobile oil. The oil was dissolved in methylene chloride (250 mL) and 2,4-difluoroamline (5.2 g) was added to the solution. After standing for 1 h, the solution was evaporated to dryness and the residue recrystallized and washed with hexane to give 9 g of (5). m.p.=138–141° C.

Ethyl 1-(2,4-difluoroanilino)-6-fluoro-7-chloro-1,4-dihydro-4-oxo-1,8-naphthyridine-3-carboxylate (6)

A 60% sodium hydride in oil suspension (1.73 g) was slowly added with stirring to a cold solution of nicotinylacrylate (5) (16.5 g) in TBF (200 mL). The mixture was refluxed with stirring under nitrogen for 1.5 h, cooled, washed with water and dried yielding 8 g of (6). m.p.=210–212° C.

1-(2,4Difluoroanitino)-6-fluoro-7-chloro-1,4-dihydro-4-oxo-18-naphthylidine-3-carboxylic acid (7)

A suspension of (6) (10 g) in 29 mL of 12 % HCl and 26 mL of glacial acetic acid was refluxed for 7.5 h. It was cooled, filtered and recrystallized from a boiling mixture of methanol and acetone to yield 6.3 g of (7) m.p.=195–200° C.

Anal. Calcd. for: $C_{15}H_6N_2F_3ClO_3$

|  | C | H | N | F | Cl |
|---|---|---|---|---|---|
| Theory: | 50.80 | 1.70 | 7.89 | 16.06 | 9.99 |
| Found: | 51.86 | 2.64 | 7.33 | 15.31 | 9.47 |

SPECIFIC REACTION SCHEME IV

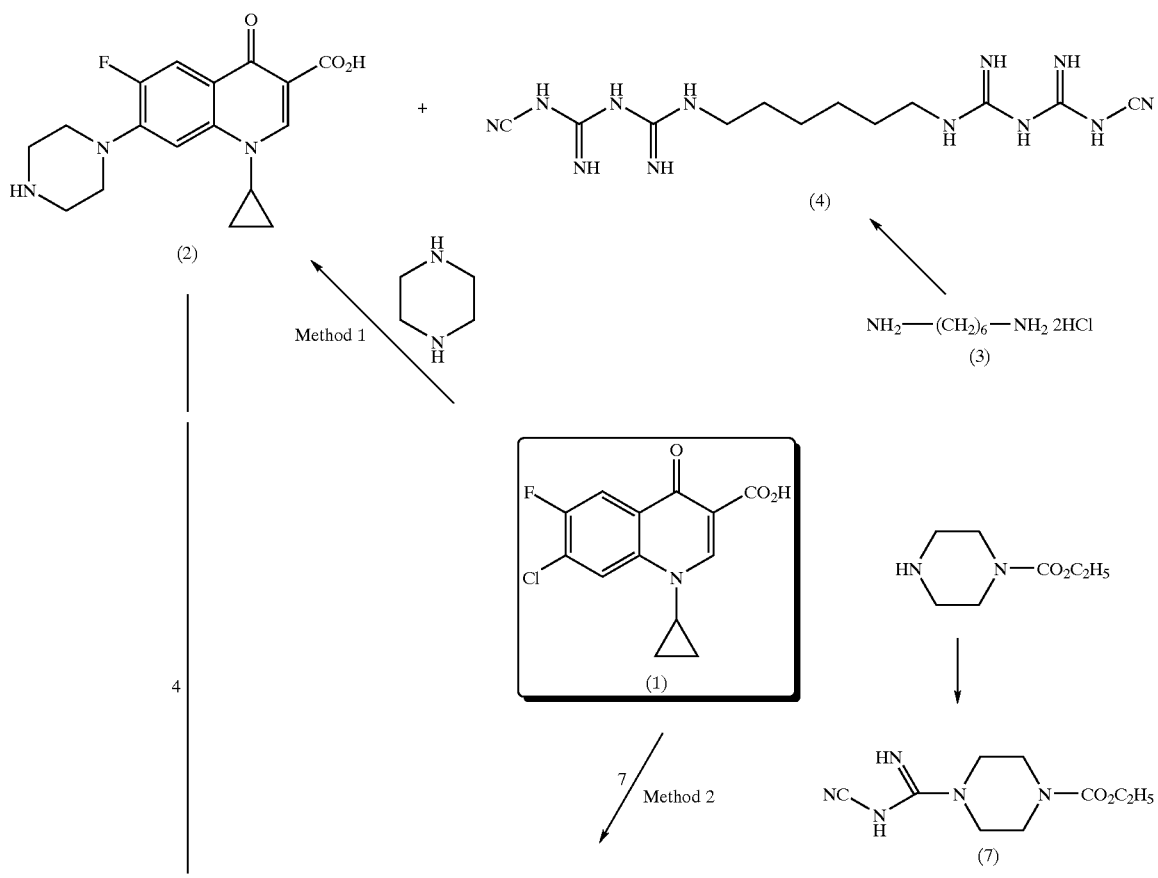

-continued

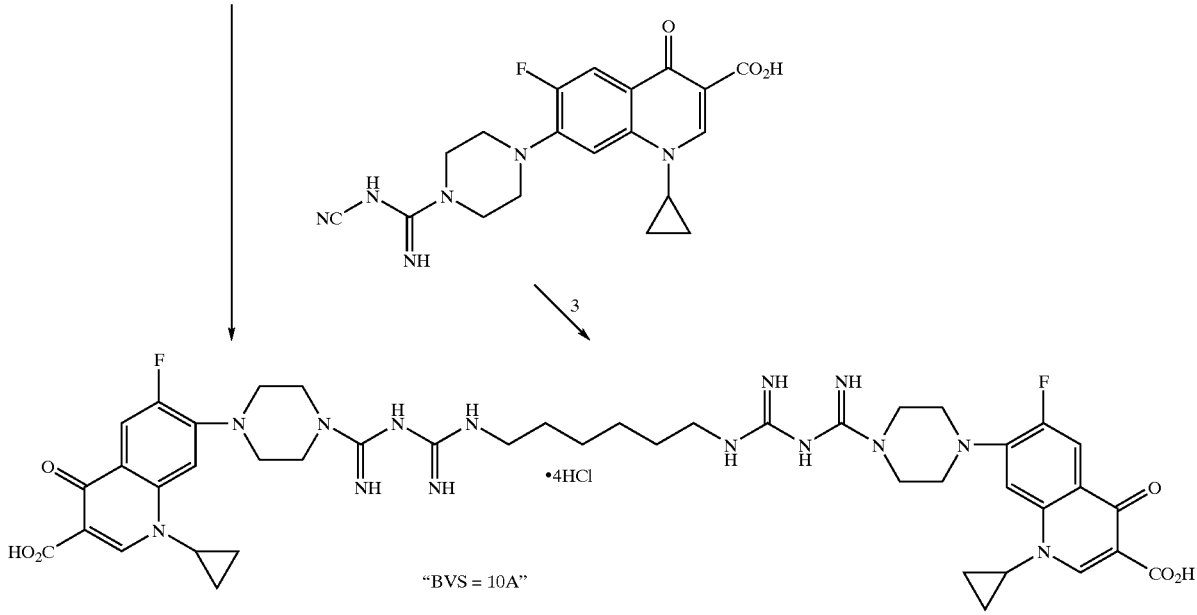

"BVS = 10A"

1-Cyclopropyl-6-fluoro-1,4-dihydro-4-oxo-7-(1-piperazinyl)-quinoline carboxylic acid monohydrochloride monohydrate (2)

Method-1

7-Chloro6-fluoro-1-cyclopropyl-1,4-dihydro-4-oxo-quinoline-3-carboxylic acid (1) (10 g) was added with stirring to melted piperazine (10 g) at 155–160° C. during 15 min. heating was continued for 0.5 h. The reaction mixture was cooled, mixed with water and filtered. The resulting solid was mixed with water and ethanol, acidified with concentrated HCl, boiled and filtered. To the clear filtrate, activated charcoal was added, boiled and filtered. It was cooled on dry ice and the solid was removed by filtration to yield 7.8 g (2). m.p. 317–321° C.

Hexamethylene bis(cyanoguanidine) (4)

1,6-Hexamethylene diamine dihydrochloride (20 g), sodium dicyandiamide (18.8 g), and 1-butanol (250 mL) were mixed and refluxed with stirring 15 h. The reaction mixture was cooled, filtered and washed with acetone. The resulting solid was mixed with water (200 mL), acidified with HCl, filtered and washed with water. It was mixed with water again, made basic NaOH, filtered, washed with water, followed by acetone and dried. Wt. 14 g (4). m. p.=195–200° C.

A mixture of (2) (5 g), (4) (1.7 g) and n-butanol (150 mL) was refluxed with stirring for 76.5 h. It was evaporated under reduced pressure. The solid was mixed with water, acidified with conc HCl, mixed with charcoal, boiled and filtered. It was cooled, precipitated with acetone, filtered and the resulting solid was recrystallized again from boiling methanol to yield 1.5 g of"BVS-10A". m.p. 100–105° C.

Anal. Calcd. for: $C_{44}H_{58}Cl_4F_2N_{14}O_6 \cdot H_2O$

| Theory: | C | H | Cl | F | N |
|---|---|---|---|---|---|
|  | 49.07 | 5.61 | 13.69 | 3.52 | 18.21 |
| Found: | 48.66 | 5.94 | 12.38 | 3.62 | 18.28 |

Anti-HIV Test Data of "BVS-10A"

Anti-HIV Test Data and the Methods Used to Test the Compound, BVS-10A.

The compound was evaluated by two test methods to establish anti-HIV (human immunodeficiency virus) activity of BVS-10A.

Method 1: CEM-SS Assay Method (SS stands for syncytium sensitive)—Description:

This is a cytoprotection assay that uses the T-lymphoblastoid tumor cell line CEM-SS and laboratory adapted strains of HIV-1. Upon infection with HIV, the CEM-SS cells form syncytia and eventually die, producing large amounts of progeny virus over the course of 4–6 days at the standard multiplicity of infection (0.01). The antiviral assay measures the ability of a given compound to inhibit the HIV-induced cell killing. In order to provide the best opportunity for the compound to demonstrate anti-HIV activity, the compound is added to uninfected cells in the microtiter plate well shortly before the addition of cell-free infectious virus. The activity of the compound is evaluated by measuring cell viability at 6 days post-infection and comparing the viability to that obtained in cell control (cells only), virus control (cells and virus only) and toxicity control (cells and compound only) wells. In general it is a very effective assay for the detection of anti-HIV activity in vitro and is predictive of anti-HIV assay in more clinically relevant assays with compound possessing a wide range of mechanism of action.

Method 2: PBMC Assay Method (Peripheral Blood Mononuclear cell)—Description

This assay addresses the issue of providing a rationale for further evaluation of the compound by providing evidence of in vitro anti-HIV activity against a low passage clinical strain of HIV-1. These fresh human peripheral blood mononuclear cell assays use fresh human cells obtained from the American Red Cross from uninfected, normal human donors. Mononuclear cells from these blood samples are isolated by centrifugation and infected with low passage clinical strains of HIV-1 which have been obtained by culture of blood cells from HIV-infected patients with uninfected PBMCs. Since the PBMCs are not killed by HIV infection, endpoint quantification is performed by measurement of virus production in each well by reverse transcriptase assay or p24 ELISA. These assays provide evidence that the test compounds will have efficacy against viruses, which will likely be encountered in patients without genetic changes, introduced by passage in cell culture.

Definitions:

Efficacy of the compound in cell culture is measured by increased cell viability in CEM-SS assays or reduction in virus production in PBMC assays. The data obtained yields a dose response curve which can be evaluated to determine doses which yield 25%, 50% and 95% protection from HIV-induced cell killing or virus production. These concentration are reported as the 1C25, 1C50 and 1C95 values. Similarly since toxicity is evaluated in parallel, the 25%, 50% and 95% toxic concentrations can be calculated based on the reduction of cell viability observed in the presence of drug alone. These concentrations are reported as the TC25, TC50 and TC95 values. The ratio of toxicity to efficacy constitutes the therapeutic index TC50/IC50.

Data:

BVS-10A was active at two concentrations and provided 100% protection at 32 and 100 μg/mL in CEM-SS cells. The calculated $IC_{50}$ was 16.6 μ/mL and the $IC_{95}$ was 30 μg/mL. The observed therapeutic index was not calculated since the compound remained nontoxic at 100 μg/mL (T1>10). BVS-10A was nontoxic at 100 μ/mL. In the microliter XTT assay, protection from HIV-induced cell killing in the CEM-SS cells is directly related to a reduction in virus load as measured by RT (reverse transcriptase) or p24 ELISA. Complete protection in this assay therefore is correlated with complete suppression of virus production.

BVS-10A was determined to be active at concentrations greater than 3.2 μg/mL in PBMCs. Toxicity was detected in PBMCs at 100 μg/mL and no toxicity was observed in CEM-SS cells at concentrations up to 100 μg/mL. The compound, BVS-10A becomes 100% active in both anti-HIV assays performed. Though virus production in CEM-SS cells is not directly measured, in general, protection from HIV-induced cell.killing usually correlates directly with reduced virus load. Thus, at points where 100% protection is observed, it is expected that little to no virus production at those concentrations. In the PBMC assays, the end point used does measure the amount of virus produced from the infected, treated cells and in this assay, 100% protection does mean complete suppression of virus production.

The compound, BVS-10A was tested against HIV using di-deoxycytosine (ddC) as a positive control drug by CEM-SS cell method. The test results are shown in Tables 1 and 2. It was also tested against HIV using AZT as a positive control by PBMC method. The test results are given in Tables 3 and 4. RT stands for reverse transcriptase.

TABLE 1

| | PLATE HAS DRUG DOC | | | | IN VITRO ANTIVIRAL RESULTS XTT ASSAY | | | | DRUG: DDC SI: >485.51 | | | |
|---|---|---|---|---|---|---|---|---|---|---|---|---|
| | 1 | 2 | 3 | 4 | 5 | 6 | 7 | 8 | 9 | 10 | 11 | 12 |
| | | | reagent background | | | | | | plastic background | | | |
| A | 0.187 | 0.179 | 0.180 | 0.178 | 0.183 | 0.184 | 0.088 | 0.086 | 0.086 | 0.086 | 0.082 | 0.083 |
| | tox | cc/vc | experimental = high concentrations | | | tox | tox | experimental = low concentrations | | | cc/vc | tox |
| B | 1.902 | 1.648 | 1.329 | 1.695 | 0.846 | 1.772 | 1.688 | 0.290 | 0.277 | 0.325 | 1.755 | 1.688 |
| C | 1.731 | 1.572 | 1.316 | 1.530 | 1.273 | 1.418 | 1.460 | 0.265 | 0.440 | 0.281 | 1.645 | 1.584 |
| D | 1.719 | 1.560 | 1.840 | 1.324 | 1.482 | 1.504 | 1.594 | 0.386 | 0.318 | 0.342 | 1.579 | 1.617 |
| E | 1.818 | 0.380 | 1.500 | 1.458 | 1.369 | 1.490 | 1.537 | 0.286 | 0.323 | 0.380 | 0.238 | 1.779 |
| F | 2.221 | 0.251 | 2.096 | 1.981 | 1.997 | 1.791 | 1.519 | 0.429 | 0.392 | 0.317 | 0.311 | 1.738 |
| G | 2.538 | 0.275 | 1.946 | 1.922 | 2.020 | 1.959 | 1.729 | 0.456 | 0.310 | 0.395 | 0.244 | 1.724 |
| | | | colorimetric background = high concentrations | | | | | | colorimetric background = low concentrations | | | |
| H | 0.185 | 0.180 | 0.185 | 0.212 | 0.184 | 0.179 | 0.177 | 0.179 | 0.182 | 0.178 | 0.176 | 0.192 | tox = cell toxicity
cc = cell control
vc = virus control
BOLD = highest drug conc
values shown are optional densities

| VIRUS | HIV1 | PASSAGE — | PROJECT # | — |
|---|---|---|---|---|
| CELLS | CEMSS | PASSAGE 15 | SPONSOR | SHETTY |
| | | OPERATOR 12S | TEST DATE | Sep. 10, 1997 |
| | | | DATE READ | Sep. 16, 1997 |

| STRN | RF | DRUG DDC | 25% | 50% | 95% |
|---|---|---|---|---|---|
| REAGENT | 0.182 | TC (CM) | >10.00 | >10.00 | >10.00 |
| VIRUS CONTROL | 0.091 | IC (CM) | 0.01 | 0.02 | 2.11 |
| CELL CONTROL | 1.445 | ANTIVIRAL INDEX (AI) | >754.29 | >485.51 | >4.73 |
| DIFFERENTIAL | 1.353 | | | | |

TABLE 1-continued

| | DRUG DDC | | ANTIVIRAL TEST VALUES | | CYTOTOXICITY TEST VALUES | | |
|---|---|---|---|---|---|---|---|
| | ROW ON PLATE | CONC. ($\mu$M) | MEAN O.D. | % RED. IN VIRAL CPE | MEAN O.D. | % CELL VIABILITY | COLORIMETRIC CONTROL |
| BASED ON | low  B | 0.00003 | 0.014 | 1% | 1.496 | 100% | 0.010 |
| VALUES OF | C | 0.0001 | 0.062 | 5% | 1.346 | 93% | −.006 |
| COLUMNS | D | 0.00032 | 0.080 | 6% | 1.428 | 99% | −.004 |
| 7 through 12 | E | 0.001 | 0.057 | 4% | 1.476 | 100% | 0.000 |
| (RIGHT SIDE | F | 0.0032 | 0.109 | 8% | 1.450 | 100% | −.003 |
| OF PLATE) | G | 0.01 | 0.119 | 9% | 1.550 | 100% | −.005 |
| BASED ON | B | 0.032 | 1.019 | 75% | 1.658 | 100% | −.003 |
| VALUES OF | C | 0.1 | 1.099 | 81% | 1.391 | 96% | 0.002 |
| COLUMNS | D | 0.32 | 1.246 | 92% | 1.400 | 97% | 0.030 |
| 1 through 6 | E | 1 | 1.166 | 86% | 1.469 | 100% | 0.003 |
| (LEFT SIDE | F | 3.2 | 1.754 | 100% | 1.826 | 100% | −.002 |
| OF PLATE) | high  G | 10 | 1.687 | 100% | 2.064 | 100% | 0.003 |

TABLE 2

| PLATE HAX DRUG BVS10A | | | | | IN VITRO ANTIVIRAL RESULTS XTT ASSAY | | | | DRUG: BVS10A SI: >6.01 | | | |
|---|---|---|---|---|---|---|---|---|---|---|---|---|
| | 1 | 2 | 3 | 4 | 5 | 6 | 7 | 8 | 9 | 10 | 11 | 12 |
| | reagent background | | | | | | plastic background | | | | | |
| A | 0.179 | 0.171 | 0.165 | 0.172 | 0.177 | 0.174 | 0.095 | 0.089 | 0.091 | 0.089 | 0.095 | 0.088 |
| | tox | cc/vc | experimental = high concentrations | | | tox | tox | experimental = low concentrations | | | cc/vc | tox |
| B | 1.547 | 1.414 | 0.232 | 0.279 | 0.353 | 1.557 | 1.509 | 0.269 | 0.238 | 0.325 | 1.438 | 1.462 |
| C | 1.667 | 1.394 | 0.282 | 0.334 | 0.391 | 1.695 | 1.499 | 0.251 | 0.326 | 0.271 | 1.383 | 1.472 |
| D | 1.806 | 1.347 | 0.233 | 0.282 | 0.267 | 1.633 | 1.450 | 0.252 | 0.258 | 0.229 | 1.332 | 1.498 |
| E | 1.826 | 0.287 | 0.335 | 0.307 | 0.426 | 2.108 | 1.504 | 0.281 | 0.296 | 0.263 | 0.251 | 1.560 |
| F | 2.634 | 0.226 | 1.520 | 1.786 | 1.936 | 2.470 | 1.522 | 0.314 | 0.330 | 0.322 | 0.248 | 1.493 |
| G | 1.877 | 0.232 | 1.868 | 2.814 | 2.038 | 2.674 | 1.543 | 0.250 | 0.259 | 0.276 | 0.236 | 1.533 |
| | colorimetric background = high concentrations | | | | | | colorimetric background = low concentrations | | | | | |
| H | 0.179 | 0.162 | 0.163 | 0.165 | 0.169 | 0.167 | 0.170 | 0.169 | 0.168 | 0.167 | 0.163 | 0.169 | tox = cell toxicity
cc = cell control
vc = virus control
BOLD = highest drug conc
values shown are optional densities

| VIRUS | HIV1 | PASSAGE — | PROJECT # | — |
|---|---|---|---|---|
| CELLS | CEMSS | PASSAGE 15 | SPONSOR | SHETTY |
| | | OPERATOR 12S | TEST DATE | Sep. 10, 1997 |
| | | | DATE READ | Sep. 16, 1997 |

| STRN | RF | DRUG BVS 10A | 25% | 50% | 95% |
|---|---|---|---|---|---|
| REAGENT | 0.173 | TC (UG/mL) | >100.00 | >100.00 | >100.00 |
| VIRUS CONTROL | 0.070 | IC (UG/mL) | 12.00 | 16.60 | 30.00 |
| CELL CONTROL | 1.212 | ANTIVIRAL INDEX (AI) | >8.33 | >6.01 | >3.34 |
| DIFFERENTIAL | 1.141 | | | | |

| | DRUG BVS10A | | ANTIVIRAL TEST VALUES | | CYTOTOXICITY TEST VALUES | | |
|---|---|---|---|---|---|---|---|
| | ROW ON PLATE | CONC. (uG/mL) | MEAN O.D. | % RED. IN VIRAL CPE | MEAN O.D. | % CELL VIABILITY | COLORIMETRIC CONTROL |
| BASED ON | low  B | 0.00032 | 0.038 | 3% | 1.317 | 100% | −.004 |
| VALUES OF | C | 0.001 | 0.049 | 4% | 1.323 | 100% | −.010 |
| COLUMNS | D | 0.0032 | 0.009 | 1% | 1.307 | 100% | −.006 |
| 7 through 12 | E | 0.01 | 0.042 | 4% | 1.364 | 100% | −.005 |
| (RIGHT SIDE | F | 0.032 | 0.083 | 7% | 1.339 | 100% | −.004 |
| OF PLATE) | G | 0.1 | 0.021 | 2% | 1.369 | 100% | −.003 |
| BASED ON | B | 0.32 | 0.051 | 4% | 1.385 | 100% | −.006 |
| VALUES OF | C | 1 | 0.103 | 9% | 1.512 | 100% | −.004 |
| COLUMNS | D | 3.2 | 0.025 | 2% | 1.556 | 100% | −.008 |
| 1 through 6 | E | 10 | 0.123 | 11% | 1.804 | 100% | −.010 |

TABLE 2-continued

| (LEFT SIDE | | F | 32 | 1.515 | 100% | 2.390 | 100% | −.011 |
|---|---|---|---|---|---|---|---|---|
| OF PLATE) | high | G | 100 | 1.717 | 100% | 1.797 | 100% | 0.006 |

TABLE 3

AZT VS. ROJO IN PBMC

| CONC (μM) | 4 | 1.3 | 0.4 | 0.13 | 0.04 | 0.013 | 0.004 | 0.0013 | 0.004 | 0 |
|---|---|---|---|---|---|---|---|---|---|---|
| RT ACTIVITY (cpm) | | | | | | | | | | |
| SAMPLE 1 | 48.0 | 68.0 | 100.0 | 2679.0 | 5362.0 | 4391.0 | 4974.0 | 7727.0 | 5701.0 | 7197.8 |
| SAMPLE 2 | 52.0 | 48.0 | 602.0 | 2866.0 | 5778.0 | 7692.0 | 5443.0 | 7459.0 | 6457.0 | 7197.8 |
| SAMPLE 3 | 48.0 | 88.0 | 120.0 | 1448.0 | 5512.0 | 6218.0 | 6540.0 | 7408.0 | 5440.0 | 7197.8 |
| MEAN | 48.3 | 88.0 | 274.0 | 2397.0 | 5880.0 | 5566.3 | 5666.7 | 7531.7 | 5888.0 | 7197.8 |
| % VC | 0.7 | 8.8 | 3.8 | 32.3 | 81.7 | 77.3 | 77.6 | 104.6 | 81.5 | 100.0 |
| TOXICITY VALUES (XTT — O.D. @ 450/650 nm) | | | | | | | | | | |
| SAMPLE 1 | 2.964 | 2.954 | 2.897 | 3.239 | 3.260 | 3.165 | 2.952 | 2.908 | 3.099 | 3.151 |
| SAMPLE 2 | 2.607 | 3.085 | 3.101 | 2.984 | 2.716 | 2.933 | 3.026 | 2.704 | 2.682 | 3.151 |
| SAMPLE 3 | 2.588 | 2.945 | 3.224 | 3.158 | 2.740 | 3.291 | 2.772 | 2.908 | 3.093 | 3.151 |
| MEAN | 2.718 | 2.968 | 3.107 | 3.120 | 2.902 | 3.130 | 2.917 | 2.840 | 2.958 | 3.151 |
| % CC | 86.2 | 84.8 | 98.8 | 89.0 | 92.1 | 99.3 | 92.6 | 90.1 | 93.9 | 100.0 |

IC50 (μM) = 0.10
TC50 (μM) = >4
TI = >40.0

TABLE 4

BVS 10A VS. ROJO IN PBMC

| CONC (μg/ml) | 100 | 32 | 10 | 3.2 | 1 | 0.32 | 0.1 | 0.032 | 0.01 | 0 |
|---|---|---|---|---|---|---|---|---|---|---|
| RT ACTIVITY (cpm) | | | | | | | | | | |
| SAMPLE 1 | 48.0 | 68.0 | 100.0 | 2679.0 | 6352.0 | 4391.0 | 4974.0 | 7727.0 | 6701.0 | 7197.8 |
| SAMPLE 2 | 52.0 | 48.0 | 602.0 | 2856.0 | 6776.0 | 7092.0 | 6443.0 | 7459.0 | 6457.0 | 7197.8 |
| SAMPLE 3 | 48.0 | 88.0 | 120.0 | 1446.0 | 6512.0 | 6216.0 | 6340.0 | 7409.0 | 6440.0 | 7197.8 |
| MEAN | 49.3 | 68.0 | 274.0 | 2327.0 | 6546.7 | 5899.7 | 5919.0 | 7531.7 | 6532.7 | 7197.8 |
| % VC | 0.7 | 0.9 | 3.8 | 32.3 | 91.0 | 82.0 | 82.2 | 104.6 | 90.8 | 100.0 |
| TOXICITY VALUES (XTT — O.D. @ 450/650 nm) | | | | | | | | | | |
| SAMPLE 1 | 1.874 | 3.468 | 3.855 | 3.710 | 3.465 | 3.641 | 3.351 | 3.631 | 3.699 | 3.308 |
| SAMPLE 2 | 1.838 | 3.470 | 3.856 | 3.383 | 3.378 | 3.009 | 3.587 | 3.795 | 3.504 | 3.308 |
| SAMPLE 3 | 1.573 | 2.721 | 3.238 | 3.178 | 2.699 | 3.368 | 2.703 | 2.853 | 3.042 | 3.308 |
| MEAN | 1.695 | 3.220 | 3.583 | 3.424 | 3.181 | 3.339 | 3.214 | 3.426 | 3.415 | 3.308 |
| % CC | 51.2 | 97.3 | 108.3 | 103.5 | 96.2 | 100.9 | 97.1 | 103.6 | 103.2 | 100.0 |

IC50 (μg/ml) = 2.54
TC50 (μg/ml) = >100
TI = >39.4

Explanation of the results: The two assays measure the ability of a test compound to inhibit HIV replication. In PBMCs, virus replication occurs without any evidence of cytopathic effect or cell killing. In CEM-SS cells, virus replication results in significant cytopathic effect and cell killing.

Thus, PBMCs assay measures the amount of virus released from the infected cells into the tissue culture supernatant. The activity of the test compound is measured by its ability to reduce the level of virus production relative to the virus controls (cells+virus with no added compound). In PBMC culture we use reverse transcriptase activity in the supernatant to quantify the amount of virus production from the infected cells. Endpoint quantification is performed at 6 days post-infection. Toxicity of the compound to the target cells is measured by the incorporation of tritiated thymidine or by use of the tetrazolium dye XTT.

CEM-SS cells assay measures the ability of the compound to inhibit HIV induced cell killing. The cells are stained at 6 days post-infection with the tetrazolium dye XTT which is converted to a colored formazan product by the mitochondria of viable cells. Protection from cell killing afforded by the test compound is measured by comparison to both cell controls and virus controls. Cell killing in this system is directly related to the amount of virus produced by the infected cells and XTT-formazan production is proportional to the number of viable cells in each well. Toxicity of the compound to the target cells is measured in parallel.

Interpretation of the results: The results in both assay systems indicate that BVS-10A was able to inhibit the replication of HIV-1. In both assays a high test compound concentration of 100 µg/mL was used. In PBMCs, 50% inhibition of virus replication was achieved at 2.5 µg/mL. In CEM-SS cells, 50% inhibition of cell killing was achieved at 12.0 µg/mL. Toxicity was observed in the PBMC cultures with 50% inhibition of cell growth at approximately 100 µg/mL. No toxicity at the high test concentration was observed in CEM-SS cells. AZT and ddC were used as positive anti-HIV controls in order to be sure the assay system worked as expected. The results obtained with these control compounds indicate that each of these antiviral assays of BVS-10A represent good antiviral evaluations. Significance of the results: These assays suggest that BVS-10A is an effective inhibitor of HIV-1 replication in both established and fresh human cell systems. BVS-10A exhibits a therapeutic index of approximately 50 in PBMCs and >10 in CEM-SS cells.

Detailed descriptions of both the CEM-SS cell method and the PBMC method are given below.

CEM-SS Cells Assay

Microtiter Antiviral XTT Assay

Cell Preparation:

CEM-SS cells (or other established human cell line used in these experiments) were passaged in T-150 flasks for use in the assay. On the day preceding the assay, the cells were split 1:2 to assure they would be in an exponential growth phase at time of infection. On the day of assay the cells were washed twice with tissue culture medium and resuspended in fresh tissue culture medium. Total cell and viability counting was performed using hemacytometer and trypan blue dye exclusion. Cell viability was greater than 95% for the cells to be utilized in the assay. The cells were pelleted and resuspended at $2.5 \times 10^4$ cells per ml in tissue culture medium. Cells were added to the drug-containing plates in a volume of 50 µl.

Virus Preparation:

A pretitered aliquot of virus was removed from the freezer (−80° C.) and allowed to thaw slowly to room temperature in a biological safety cabinet. The virus was resuspended and diluted into tissue culture medium such that the amount of virus added to each well in a volume of 50 µl will be the amount determined to give complete cell killing at 6 days post-infection. In general the virus pools produced with the IIIB isolate of HIV required the addition of 5 µl of virus per well. Pools of RF virus were five to ten fold more potent, requiring 0.5–1 µl per well. $TCID_{50}$ calculation by endpoint titration in CEM-SS cells indicated that the multiplicity of infection of these assays ranged from 0.005–2.5.

Plate format:

The format of the test plate has been standardized by Southern Research Institute. Each plate contained cell control wells (cells only), virus control wells (cells plus virus), drug toxicity control wells (cells plus drug only), drug colorimetric control wells (drug only) as well as experimental wells (drug plus cells plus virus).

XTT Staining of Screening Plates:

After 6 days of incubation at 37° C. in a 5% $CO_2$ incubator the test plates were analyzed by staining with the tetrazolium dye XTT. XTT-tetrazolium is metabolized by the mitochondrial enzymes of metabolically active cells to a soluble formazan product, allowing the rapid quantitative analysis of the inhibition of HIV-induced cell killing by anti-HIV test substances. On day 6 post-infection plates were removed from the incubator and observed. The use of round bottom microtiter plates allows rapid macroscopic analysis of the activity of a given test compound by the evaluation of pellet size. The results of the macroscopic observations were confirmed and enhanced by further microscopic analysis.

XTT solution was prepared daily as a stock of 1 mg/ml in PBS. Phenazine methosulfate (PMS) solution was prepared at 15 mg/ml in PBS and stored in the dark at −20° C.

CEM-SS Cells Assay

XTT-PMS stock was prepared immediately before use by diluting the PMS 1:100 into PBS and adding 40 ul per ml of XTT solution. Fifty microliters of XTT/PMS was added to each well of the plate and the plate was reincubated for 4 hours at 37° C. Adhesive plate sealers were used in place of the lids, the sealed plate was inverted several times to mix the soluble formazan product and the plate was read spectrophotometrically at 450 nm with a Molecular Devices Vmax plate reader. Using an in-house computer program %CPE Reduction, %Cell Viability, $IC_{25, 50 \& 95}$, $TC_{25, 50 \& 95}$ and other indices were calculated and the graphic results summary was displayed.

PBMC Assay

Anti-HIV Activity in Fresh Human Cells: Assay in Fresh Human T-lymnhocvtes

Fresh human peripheral blood lymphocytes (PBL) are isolated from voluntary Red Cross donors, seronegative for HIV and HBV. Leukophoresed blood is diluted 1:1 with Dulbecco's phosphate buffered saline (PBS), layered over 14 mL of Ficoll-Hypaque density gradient in a 50 mL centrifuge tube. Tubes are then centrifuged for 30 minutes at 600×g. Banded PBLs are gently aspirated from the resulting interface and subsequently washed 2× with PBS by low speed centrifugation. After final wash, cells are enumerated by trypan blue exclusion and resuspended at 1×10E7/mL in RPMI 1640 with 15% Fetal Bovine Serum (FBS), 2 mM L-glutamine, 4 µg/mL PHA-P and allowed to incubate for 48–72 hours at 37° C. After incubation, PBLs are centrifuged and reset in RPMI 1640 with 15% FBS, 2 mM L-glutamine, 100 U/mL. penicillin, 100 ug/mL streptomycin, 10 ug/mL gentamycin, and 20 U/mL recombinant human IL-2. PBLs are maintained in this medium at a concentration of 1–2×10E6/mL with bi-weekly medium changes, until use in assay protocol. For the PBL assay, PHA-P stimulated cells from at least two normal donors are pooled, set in fresh medium at 2×10E6/mL and plated in the interior wells of a 96 well round bottom microplate at 50 µL/well. Test drug dilutions are prepared at a 2× concentration in microtiter tubes and 100 µL of each concentration is placed in appropriate wells in a standard format. 50 µL of a predetermined dilution of virus stock is placed in each test well. Wells with cells and virus alone are used for virus control. Separate plates are identically set without virus for drug cytotoxicity studies using an XTT assay system.

In the standard PBL assay (MOI: 0.2), the assay was ended on day 7 following collection of cell free supernatant samples for reverse transcriptase activity assay. In the low MOI PBL assay (MOI: 0.02), supernatant samples were collected on day 6, day 11, and day 14 post-infection and analyzed for RT activity. Tritiated thymidine triphosphate (NEN) (TTP) was resuspended in distilled $H_2O$ at 5 Ci/ml. Poly rA and oligo dT were prepared as a stock solution which was kept at −20° C. The RT reaction buffer was prepared fresh on a daily basis and consists of 125 μL IM EGTA, 125 μL $dH_2O$, 110 μL 10% SDS, 50 μL 1M Tris (pH 7.4), 50 μL 1M DTT, and 40 μL 1M $MgCl_2$. These three solutions were mixed together in a ratio of 2 parts TTP, 1 part poly rA:oligo dT, and 1 part reaction buffer. Ten microliters of this reaction mixture was placed in a round bottom microtiter plate and 15 μL of virus containing supernatant was added and mixed. The plate was incubated at 37° C. in a water bath with a solid support to prevent submersion of the plate and incubated for 60 minutes. Following reaction, the reaction volume was spotted onto pieces of DE81 paper, washed 5 times for 5 minutes each in a 5% sodium phosphate buffer, 2 times for 1 minute each in distilled water, 2 times for 1 minute each in 70% ethanol, and then dried. Opti-Fluor O was added to each sample and incorporated radioactivity was quantitated utilizing a Wallac 1450 Microbetaplus liquid scintillation counter.

Tritiated thymidine incorporation was measured in parallel cultures at day 7. Each well was pulsed with 1 μCi of tritiated thymidine and the cells were harvested 18 hours later with a Skatron cell harvester onto glass fiber filter papers. The filters were dried, placed in a scintillation vial with 1 ml of scintillation cocktail and incorporated radioactivity was quantitated on a Packard Tri-Carb 1900 TR liquid scintillation counter.

Antibacterial Test Data of "BVS-10A"

Antibacterial Test Data and Assay Method Used to Evaluate "BVS-10" Compound

Test Results:

The compound BVS-10A was screened against several bacteria and the yeast, *Candida albicans*. The compound showed broad antibacterial activity, inhibiting the growth of all of the bacterial strains. The compound was the most active overall with minimum inhibitory concentrations (MIC) of in the range of <0.128 to 12.8 μg/mL except for C. albicans. Trimethoprim was used as a positive control drug.

The organisms are listed in Table 5 and test results are listed in Table 6.

TABLE 5

| Strain | Abbreviation | Source |
| --- | --- | --- |
| Staphylococcus aureus | Sa | ATCC 6538 |
| Staphylococcus epidermidis | Se | ATCC 35984 |
| Streptococcus pneumoniae | Sp | ATCC 6303 |
| Escherichia coli | Ec | ATCC 11229 |
| Klebsiella pneumoniae | Kp | ATCC 4352 |
| Pseudomonas aeruginosa | Pa | ATCC 15442 |
| Proteus mirabilis | Pm | ATCC 9921 |

TABLE 6

| | MIC (μg/ml) | | | | | | |
| --- | --- | --- | --- | --- | --- | --- | --- |
| Compound | Sa | Se | Sp | Ec | Kp | Pa | Pm |
| BVS10A | <0.128 | <0.128 | >1.28 ≤ 12.8 | >0.128 ≤ 1.28 | <0.128 | >1.28 ≤ 12.8 | >0.128 ≤ 1.28 |
| TMP | >0.064 ≤ 0.64 | >64 | >0.64 ≤ 6.4 | >0.064 ≤ 0.64 | >0.064 ≤ 0.64 | >64 | >0.64 ≤ 6.4 |

Antibacterial Assay

Test organisms. The test organisms are listed in Table 5 along with their source. Prior to assay, overnight bacterial slant cultures were used to inoculate Mueller Hinton broth followed by incubation for 5–7 hr. Each culture was then standardized turbidimetrically to a viable count of about $10^6$ colony forming units/ml and used to inoculate the mirotiter assay plates. The viable count after addition to the plates was about $5 \times 10^5$ CFU/ml.

Experimental design. The MIC of the test compounds for the bacterial strains was determined with a microdilution broth assay in 96 well microtiter plates. The test compounds were dissolved in DMSO and then diluted 10-fold in assay medium (Mueller Hinton broth) to obtain final concentrations of 0.128, 1.28, 12.8, and 128 μg/ml. A viability control containing DMSO, diluted in the same manner as the test compounds, was used to confirm that the DMSO was not inhibitory by itself. Trimethoprim (TMP) was used as a positive drug control. The assay plates were incubated at 37° C. for about 17 hr and each assay well observed visually for growth. The MIC was determined at the lowest concentration of drug which inhibited growth.

SPECIFIC REACTION SCHEME-V
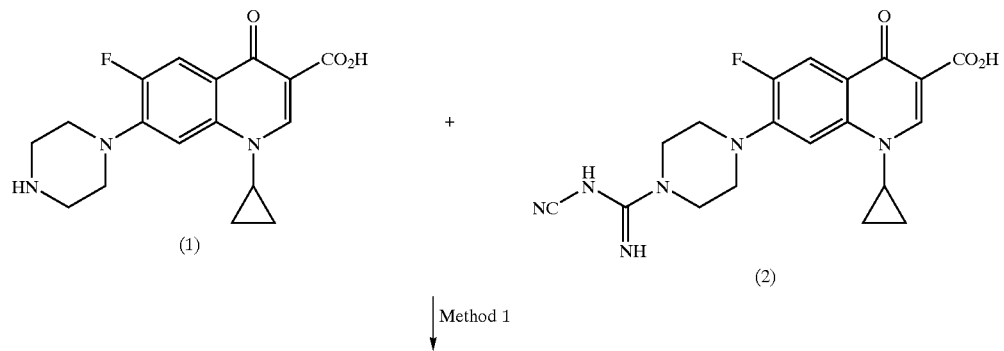
(1) + (2)
↓ Method 1
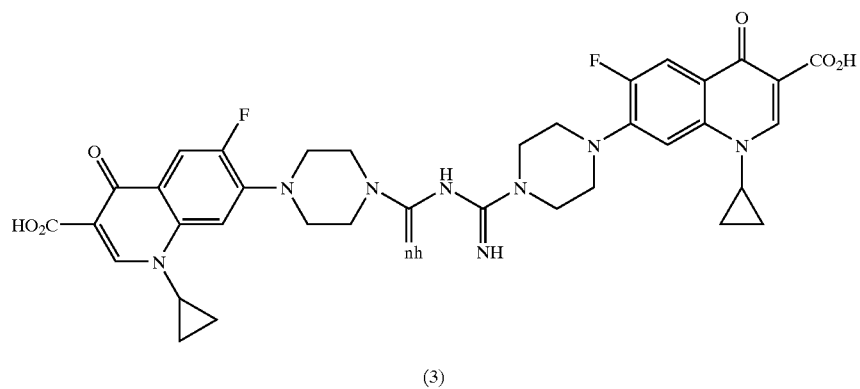
(3)
↑
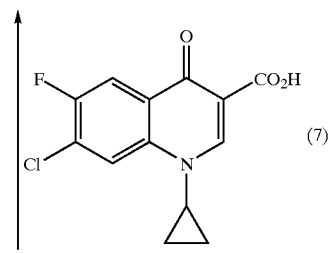
(7)
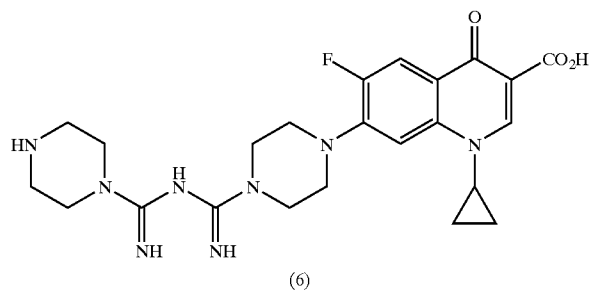
(6)

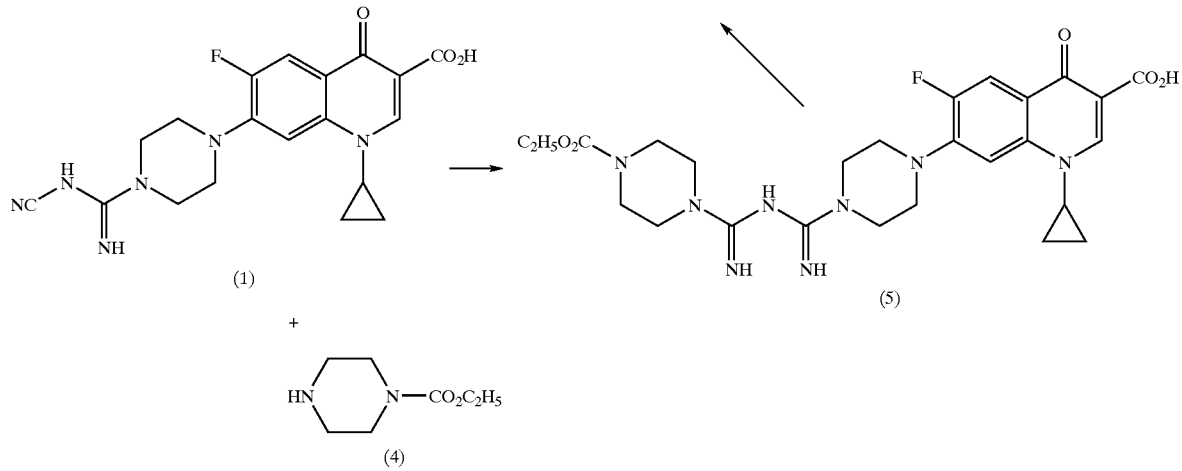

Method-1.

A mixture of 1-cyclopropyl-6-fluoro-1,4-dihydro-4-oxo-7-(1-piperazinyl)-quinoline carboxylic acid hydrochloride (1) (2.5 g), 1-cyclopropyl-6-fluoro-1,4dihydro-4-oxo-7-(4-cyanoguanidine-1-piperazinyl)quinoline carboxylic acid (2) (3 g) and a few drops of HCl was finely ground and heated at 285–290° C. for 1 hr. Thecrude solid was mixed with methanol, acidified with HCl, heated to boiling, decolorized with charcoal, filtered, concentrated to a small volume under reduced pressure, cooled on dry ice and the resulting solid was removed by filtration. The process was repeated two more times. wt. 0.7 g (3) m.p. 300–305° C. Anal. Calcd for: $C_{36}H_{41}N_9F_2Cl_4O_6 \cdot H_2O$

| Theory: | C | H | N | F | Cl |
|---|---|---|---|---|---|
|  | 48.36 | 4.85 | 14.10 | 4.25 | 15.86 |
| Found: | 48.44 | 4.96 | 14.85 | 3.18 | 14.01 |

SPECIFIC REACTION SCHEME-IV

Method 1

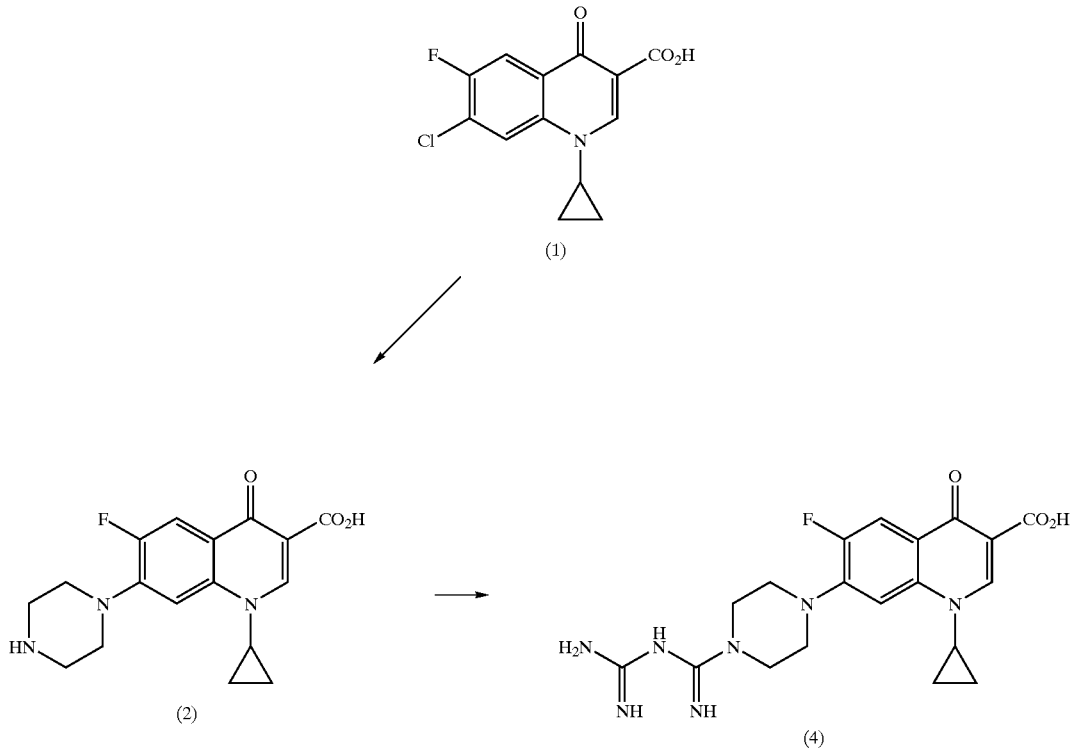

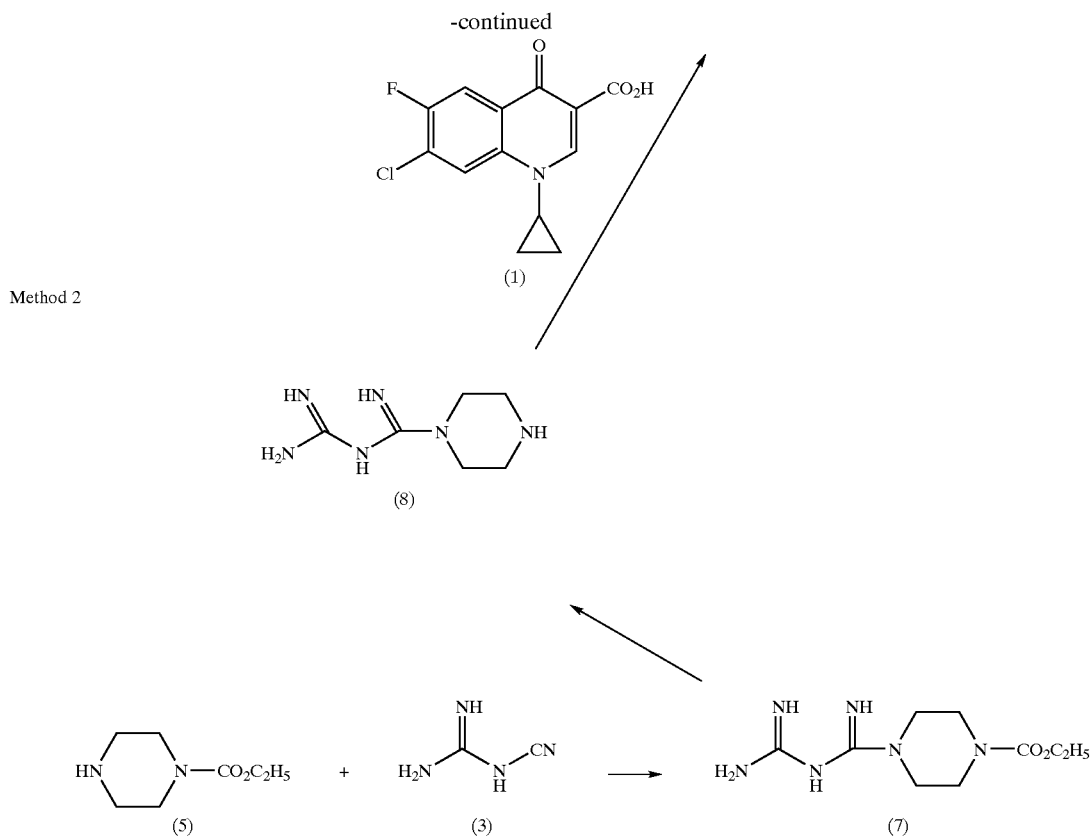

Method 2

1-Cyclopropyl-6-fluoro-1,4-dihydro-4-oxo-7-(1-piperazinyl-4-(3-amino biguanidine)-quinoline carboxylic acid dihydrochloride (4)

Method-1

A mixture of 1-cyclopropyl-6-fluoro-1,4-dihydro-4-oxo-7-(1-piperazinyl)-quinoline carboxylic acid hydrochloride (2) (5 g), n-butanol (100 mL) and dicyandiamide (1.5 g) was refluxed with stirring for 23 hours. It was evaporated to dryness under reduced pressure. The crude solid was mixed with water, filtered and washed with water. The resulting solid was mixed with ethanol, acidified with HCl, evaporated to dryness, dissolved in water, filtered, concentrated to a small volume, cooled and filtered to yield 1.3 g (4). m.p.=168–172° C. Anal. Calcd. for: $C_{19}H_{24}N_7FCl_2O_3$

|         | C     | H    | N     | F    | Cl    |
|---------|-------|------|-------|------|-------|
| Theory: | 46.73 | 4.95 | 20.06 | 3.89 | 14.72 |
| Found:  | 45.77 | 5.13 | 19.38 | 3.68 | 14.60 |

SPECIFIC REACTION SCHEME-VII

Method 1

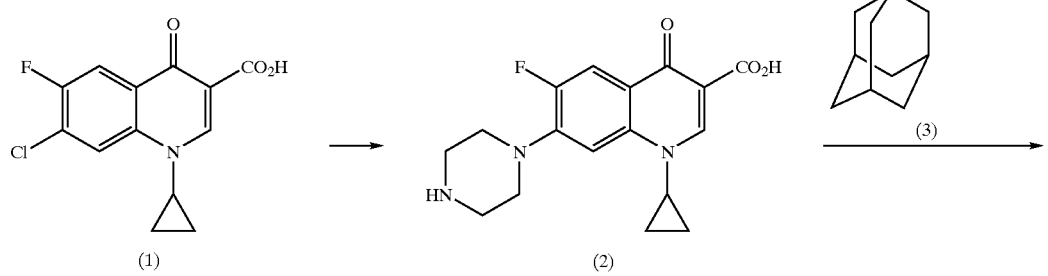

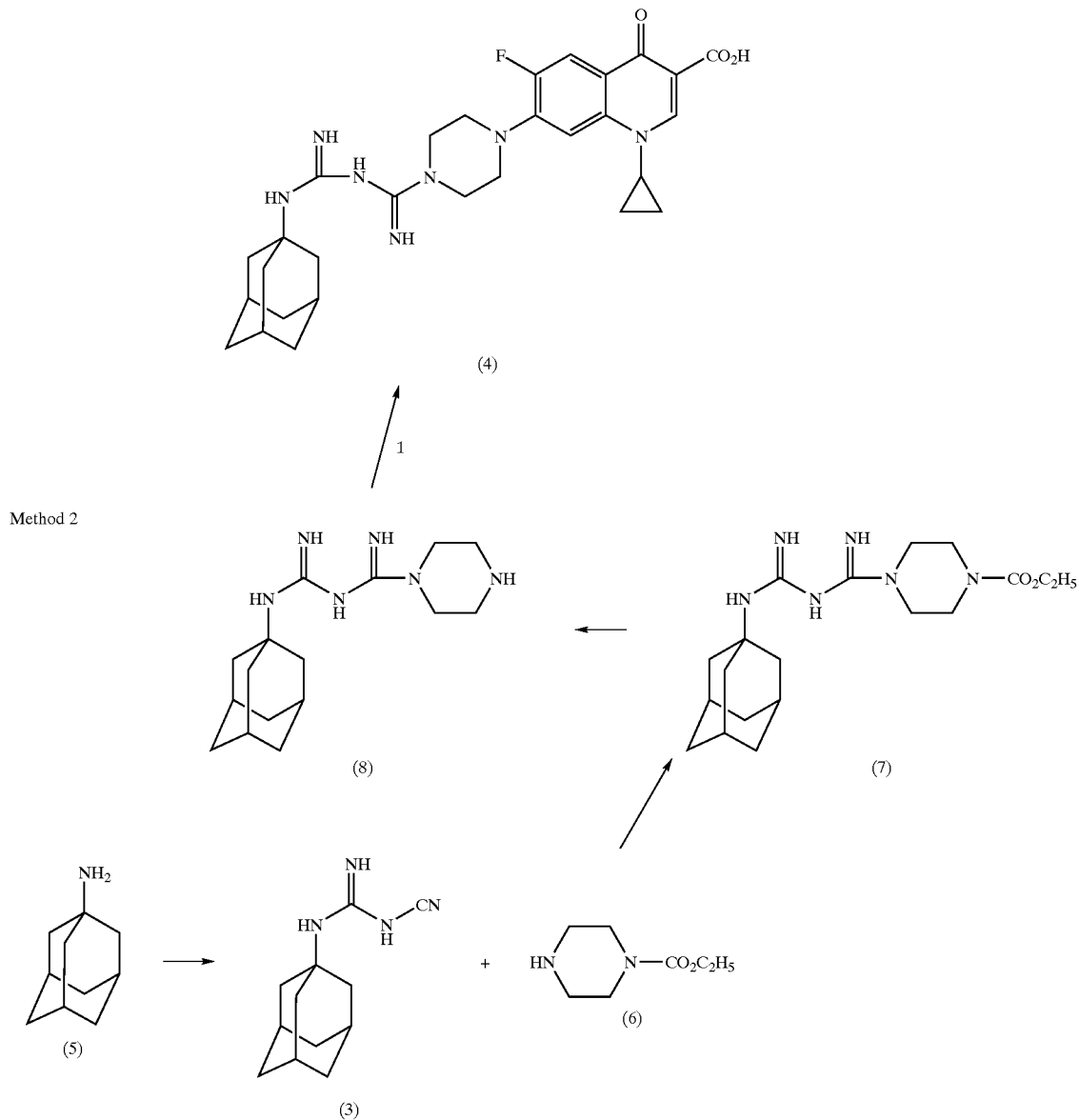

1-Cyano guanidino adamantanamine (3)

Method-1

A mixture of 1-adamantanamine hydrochloride (100 g), sodium dicyanamide (55 g), n-butanol (1L) and water (84 mL) was refluxed with stirring for 27 h. It was evaporated to dryness, mixed with water, made alkaline with NaOH, filtered, washed with water and acetone. The resulting crude solid was recrystallized from an equal mixture of boiling methanol and ethanol to yield 40 g of (3) m.p.=295–300° C.

Anal. Calcd. for: $C_{12}H_{18}N_4$

1-Cyclopropyl-6-fluoro-1,4-dihydro-4-oxo-7-(1-piperazinyl-4-(3-(1-adamantanamino) biguanidine) quinoline carboxylic acid hydrochloride (4)

A mixture of 1-cyclopropyl-6-fluoro-1,4-dihydro-4-oxo-7-(1-piperazinyl)-quinoline carboxylic hydrochloride (2) (5 g), 1-cyanoguanidine adamantanamine (3) (2.9 g) and n-butanol (200 mL) was refluxed with stirring for 174 h. It was evaporated to dryness under reduced pressure. The resulting crude solid was recrystallized twice from a mixture of boiling THF and water to give 1.5 g of (4) m.p.=260° C.–265° C.

Anal. Calcd. for: $C_{29}H_{37}N_7FClO_3$

| Theory: | C | H | N |
|---------|-------|------|-------|
|         | 66.02 | 8.31 | 25.66 |
| Found:  | 65.95 | 8.34 | 25.58 |

| Theory: | C | H | N | F | Cl |
|---------|-------|------|-------|------|------|
|         | 59.43 | 6.36 | 16.72 | 3.24 | 6.04 |
| Found:  | 58.06 | 6.77 | 16.11 | 2.75 | 5.70 |

SPECIFIC REACTION SCHEME-VIII

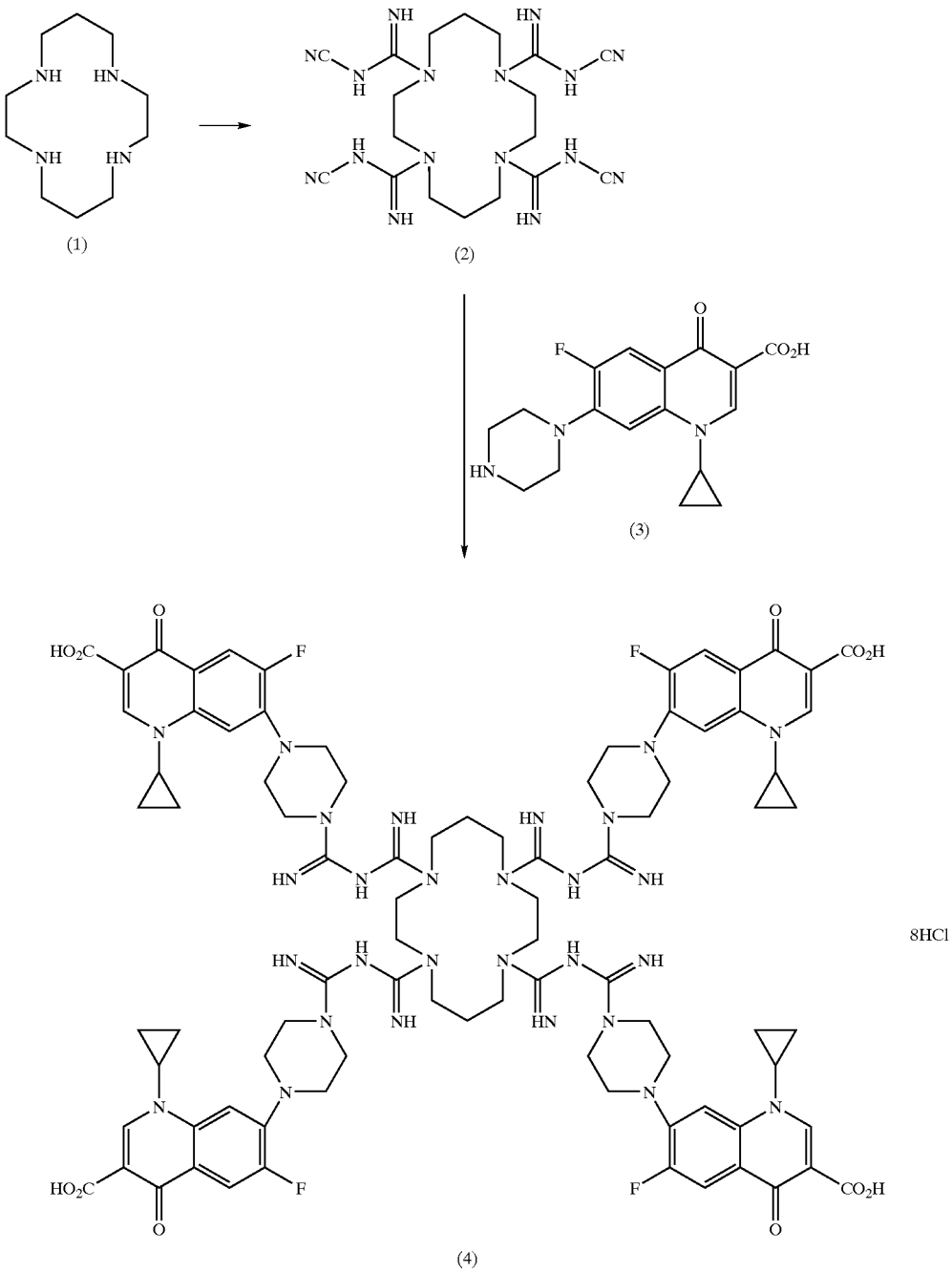

1,4,8,11-Tetraazacvclo-(1,4,8,11-tetra cyanoguanidino)-tetradecane (2)

1,4,8,11-tetraazacyclotetradecane (cyclam) (1) (5 g), sodium dicyandianide (8.8 g), n-butanol (150 mL) and water (12 mL) were mixed with 1 mL of HCl. The mixture was refluxed with stirring for 25 h. It was evaporated under reduced pressure and the residue was mixed with water, acidified with HCl, filtered, washed with water and acetone. The waxy solid mixed with water again, basified with NaOH, filtered, washed with water and acetone to give 1.3 g of (2). m.p.=>300° C.

Anal. Calcd. for: $C_{18}H_{28}N_6$

| Theory: | C | H | N |
|---|---|---|---|
| | 46.14 | 6.02 | 47.83 |
| Found: | 45.60 | 5.80 | 46.95 |

A mixture of (2) (1.3 g) and (3) (3.6 g) with a few drops of HCl was fused at 330–35° C. for 1 h. It was cooled, dissolved in boiling methanol (400 mL), decolorized with activated charcoal, filtered and evaporated under reduced pressure. The process was repeated again twice to yield 0.1 g of (4). m.p.=>300° C. Anal. Calcd. for: $C_{86}H_{108}N_{28}F_4Cl_8O_{12}$

| Theory: | C | H | N | F | Cl |
|---|---|---|---|---|---|
|  | 49.52 | 5.21 | 18.80 | 3.64 | 13.59 |
| Found: | 49.54 | 5.44 | 18.04 | 3.16 | 11.50 |

(5) (+)-9-fluoro-2,3-dihydro-3-methyl-10-(1-piperazinyl)-7-oxo-7H-pyrido[1,2,3-de]-1,4-benzoxazine-6-carboxylic acid hydrochloride (5). wt.=11 g. m.p.>300° C.

Anal. Calcd. for: $C_{17}H_{19}N_3FClO_4$

| Theory: | C | H | N | F | Cl |
|---|---|---|---|---|---|
|  | 53.19 | 4.98 | 10.94 | 4.95 | 9.23 |
| Found: | 52.76 | 5.41 | 10.57 | 4.31 | 8.65 |

SPECIFIC REACTION SCHEME-IX

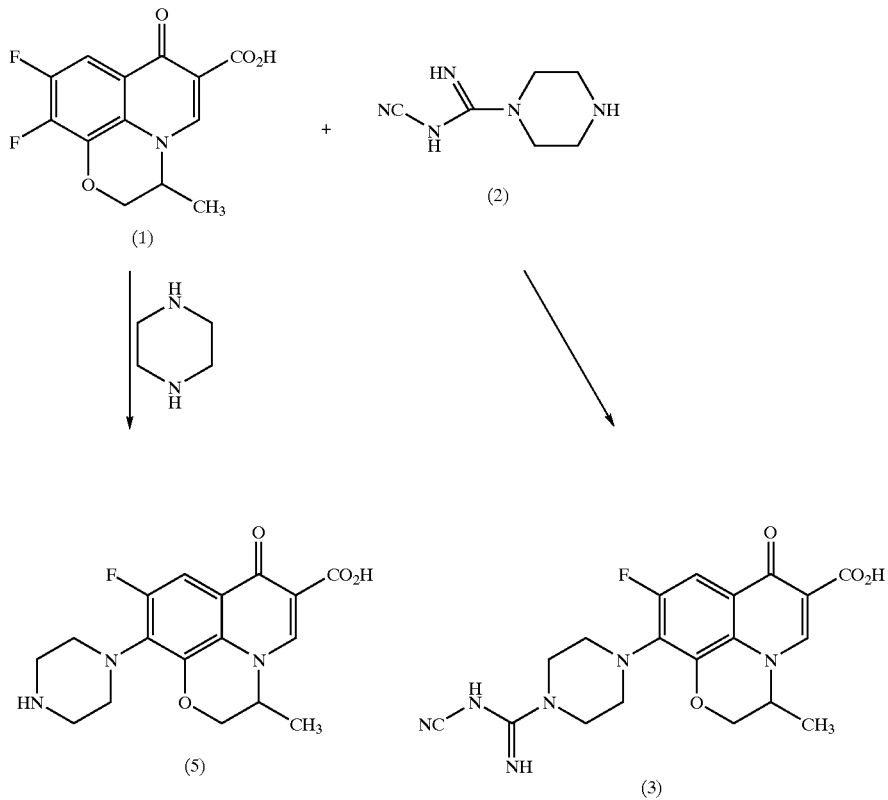

Chem. And Pharm. Bull. 32, 4907–13 (1984)

(±)-9-fluoro-2,3-dihydro-3-methyl-10-(1-piperazinyl)-7-oxo-7H-pyrido[1,2,3-de]-1,4-benzoxazine-6-carboxylic acid hydrochloride (5) Method-2

A mixture of 9,10-difluoro-3-methyl-7-oxo-2,3-dihydro-7H-pyrido-(1,2,3-de)-(1,4)benzoxazine-6-carboxylic acid (20 g) (1), anhydrous piperazine (22.96 g) and pyridine (220 mL) was refluxed with stirring for 7 h. It was evaporated to dryness, mixed with water, filtered and dried. The crude solid was mixed with methanol and water, acidified with HCl, heated to boiling, filtered and cooled to yield 16 g. of (±)-9-Fluoro-2,3-dihydro-3-methyl-10-(4-cyanoguanidino-1-piperazinyl)-7-oxo-7H-pyrido[1,2,3-de]-1,4-benzoxazine-6-carboxylic acid (3)

A mixture of (5) (10 g), sodium dicyandiamide (3,5 g), n-butanol (250 mL), water (20 mL) and a few drops of HCl was refluxed with stirring for 25 h. It was evaporated to dryness, mixed with water (250 mL), filtered and washed with acetone. The solid was mixed with water again, made basic with NaOH, filtered, washed with water and acetone to yield (3). wt=4.3 g; m.p.=298–300° C.

Anal. Calcd for: $C_{19}H_{19}N_6FO_4$

| Theory: | C | H | N | F |
|---|---|---|---|---|
| | 55.07 | 4.62 | 20.28 | 4.58 |
| Found: | 54.19 | 4.73 | 19.84 | 4.17 |

4-Cyanoguanidino-1-morpholine (3)

A solution of morpholine (50 mL) and 1-butanol (400 mL) was cooled and acidified with HCl and sodium dicyanamide (51.4 g) was added to it. The mixture was refluxed with stirring for 27 h and evaporated to dryness. The solid was mixed with water, made basic with sodium hydroxide,

SPECIFIC REACTION SCHEME-X

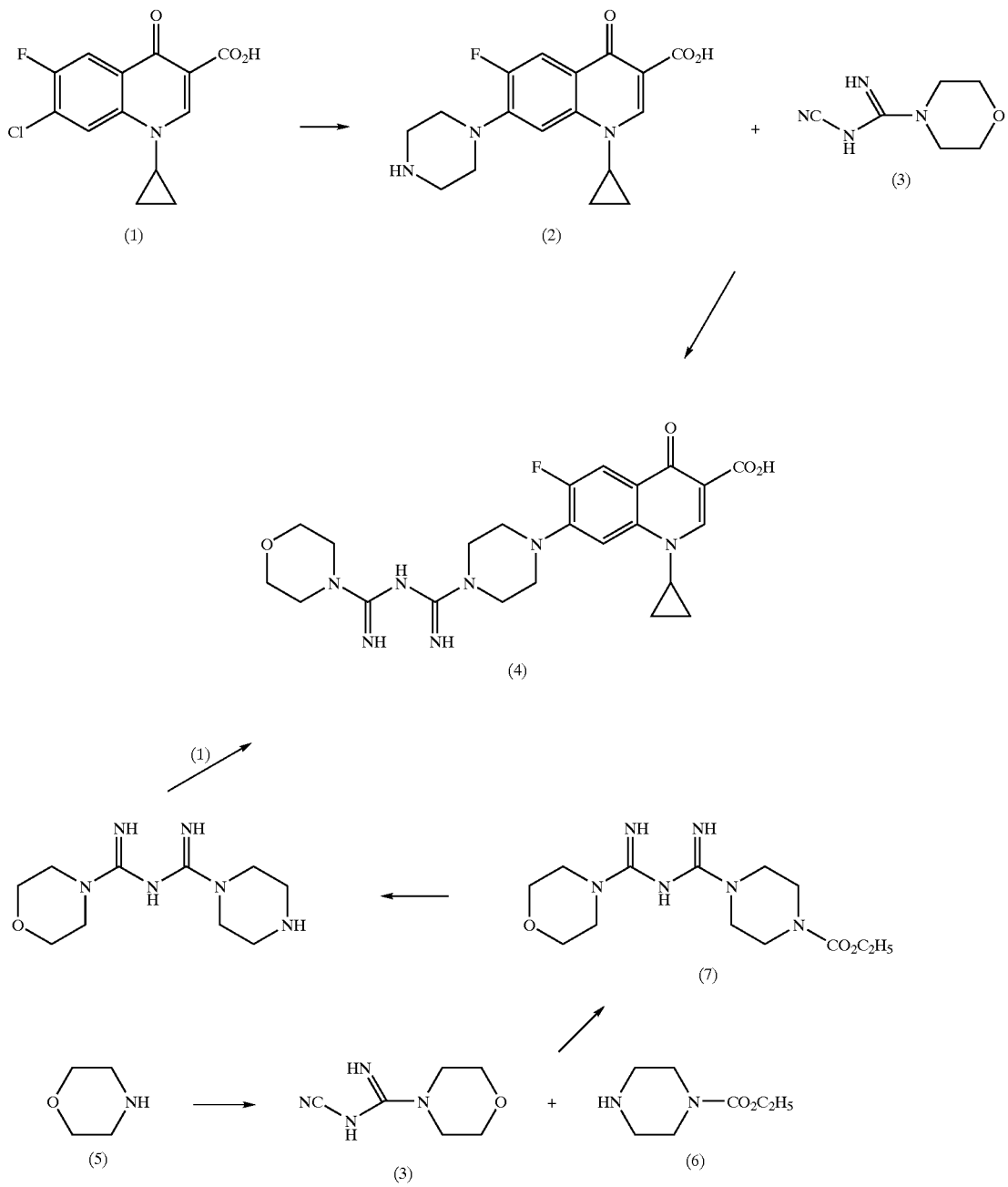

filtered, washed with water and recrystallized from boiling methanol to yield 37.8 g of (3). m.p.=225° C.–228° C.

Anal. Calcd. for: $C_6H_{10}N_4O$

| Theory: | C | H | N |
|---|---|---|---|
|  | 46.74 | 6.53 | 36.33 |
| Found: | 46.79 | 6.54 | 36.30 |

1-Cyclopropyl-6-fluoro-1,4-dihydro-4-oxo-7-(1-piperazinyl)-4-guanidino-4'-morpholine)-quinoline carboxylic acid dihydrochloride (4)

A mixture of 1-cyclopropyl-6-fluoro-1,4-dihydro-4-oxo-7-(1-piperazinyl)-quinoline carboxylic acid (2) (2 g), 4-cyanoguanidine-1-morpholine (3) (0.93 g) and a few drops of HCl was triturated and fused at 235–240° C. for 2 h. It was cooled, dissolved in boiling methanol, acidified with HCl, decolorized with charcoal, filtered cooled and made turbid with acetone. It was filtered to yield 0.6 g of (4). m.p.=250–255° C.

Anal. Calcd. for: $C_{23}H_{30}N_7FClO_2O_4$

| Theory: | C | H | N | F | Cl |
|---|---|---|---|---|---|
|  | 49.47 | 5.40 | 17.55 | 3.40 | 12.69 |
| Found: | 49.23 | 5.65 | 16.96 | 2.96 | 11.72 |

SPECIFIC REACTION SCHEME-XI

Method 1

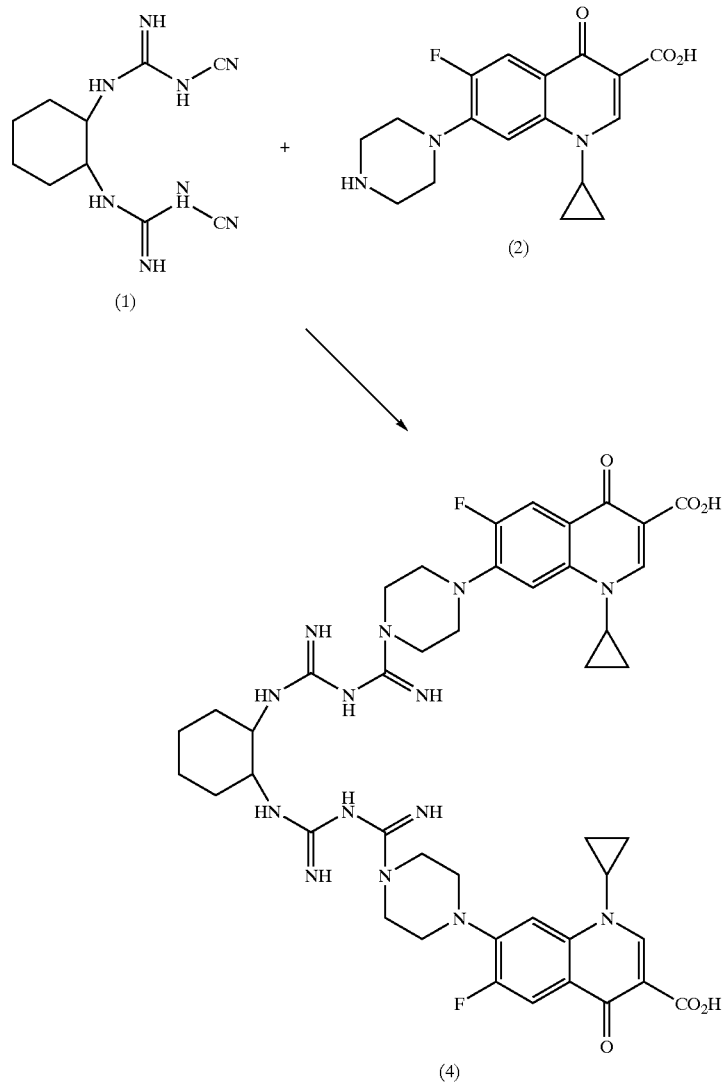

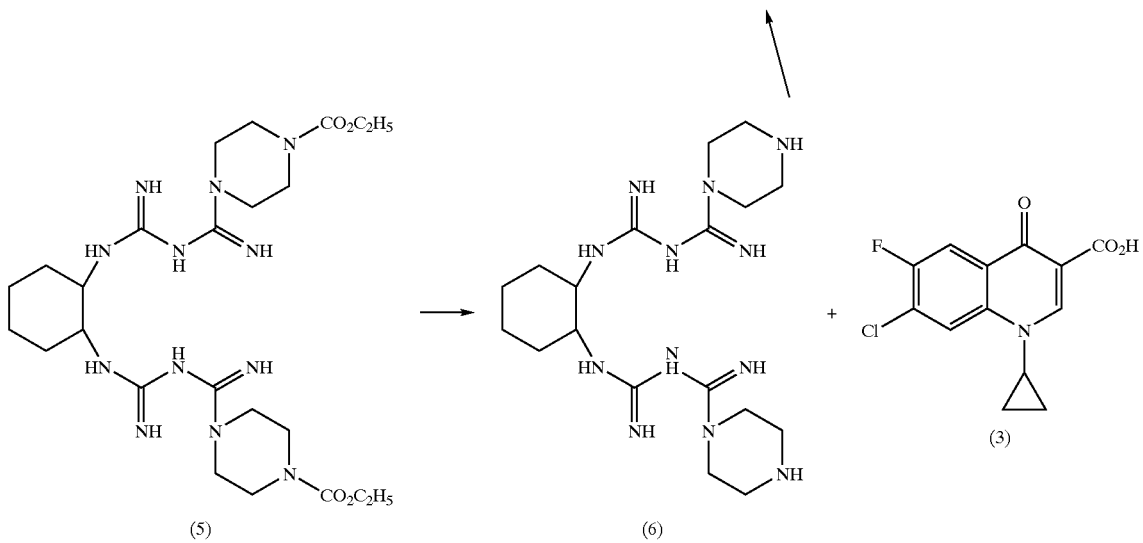

1,2-Dicyanodiguanidino cyclohexane (1)

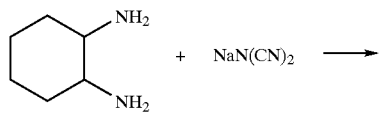

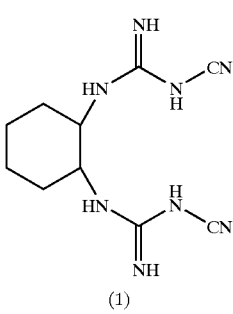

Method-1

A mixture of 1,2-diaminocyclohexane (30.0 g), sodium dicyanamide (46.7 g), n-butanol (400 mL) and concentrated hydrochloric acid (5 mL) was refluxed with stirring for 28 hours. It was cooled, filtered and washed with acetone. The solid was mixed with about 250 cc water, acidified with conc-HCl, filtered, washed with water and acetone. Again the solid was mixed with about 300 cc water, made basic with 10% sodium hydroxide solution, filtered, washed with water and acetone. The process was repeated twice more and dried at room temperature. It was recrystallized from boiling DMF (450 mL) and water to give 13.5 g (1). m.p.=290–292° C.

Anal. Calcd. for: $C_{10}H_{16}N_8$

| Theory: | C | H | N |
|---|---|---|---|
|  | 48.37 | 6.49 | 45.13 |
| Found: | 48.12 | 6.80 | 44.85 |

A mixture of 1,2-dicyanoguanidine cyclohexane (1.25 g) (1), 1-cyclopropyl-6-fluoro-1,4-dihydro-4-oxo-7-(1-piperazinyl)-3-quinolinecarboxylic acid (3.7 g) (2) and a few drops of conc. hydrochloric acid were mixed and fused with stirring at 285–290° C. for one hour. It was recrystallized from boiling ethanol and again from methanol and acetone. m.p.=285–290° C. wt.=0.5 g (4).

Anal. Calcd. for: $C_{44}H_{56}N_{14}F_2Cl_4O_6 \cdot H_2O$

|  | C | H | N | F | Cl |
|---|---|---|---|---|---|
| Theory: | 49.16 | 5.49 | 18.24 | 3.53 | 13.00 |
| Found: | 49.56 | 5.96 | 18.12 | 2.58 | 12.90 |

SPECIFIC REACTION SCHEME XII

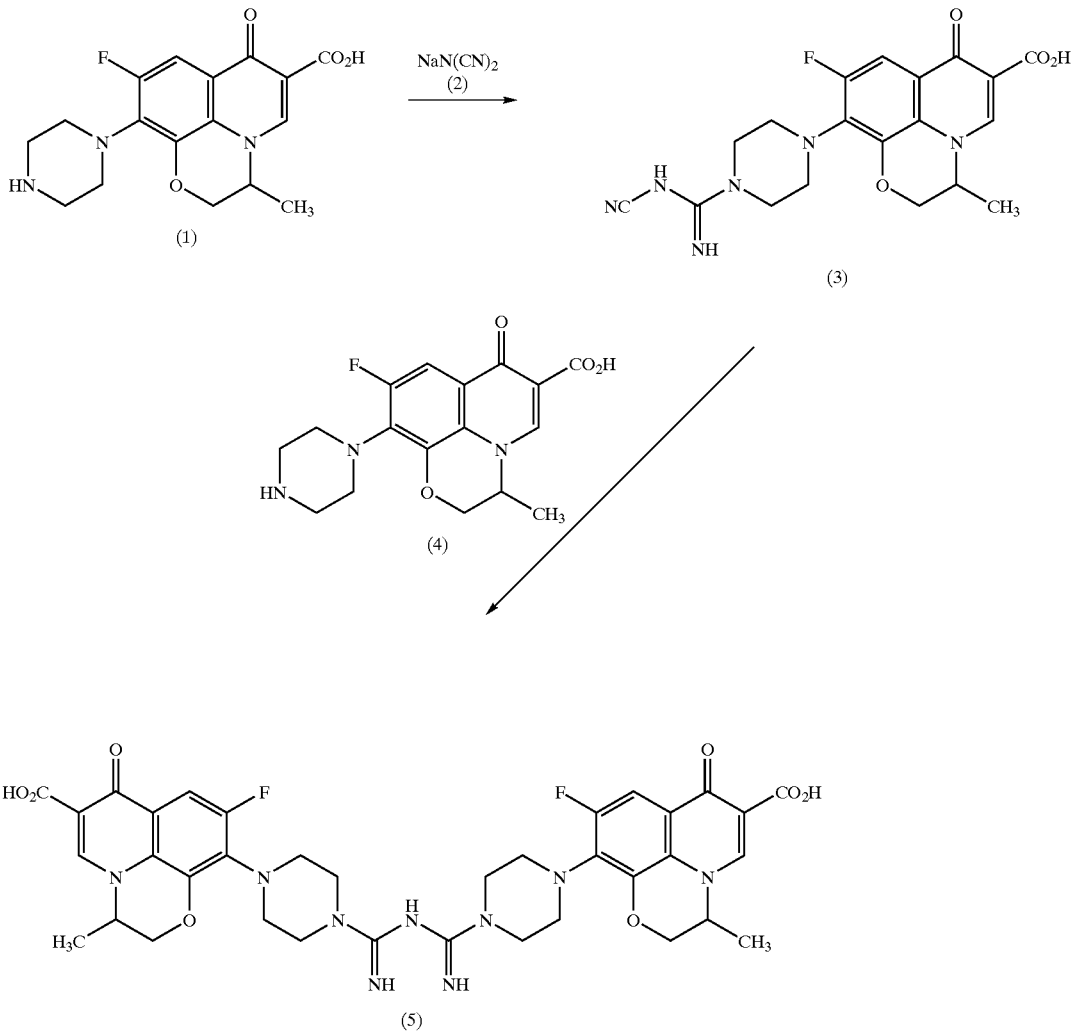

Method-1

A mixture of (±)-9-fluoro-2,3-dihydro-3-methyl-10-(1-piperazinyl)-7-oxo-7H-pyrido[1,2,3-de]-1,4-benzoxazine-6-carboxylic acid (10 g) (1), sodium dicyanamid (2.3 g) (2), n-butanol (250 mL), water (20 mL) and conc HCl (1 mL) was refluxed with stirring 25 hours. The suspension was cooled and filtered. The resulting solid was mixed with water, made basic with sodium carbonate solution, filtered, washed with water and acetone. It was recrystallized from a boiling mixture of methanol and water.

wt. 4.3 g (3), m.p. 290–293° C. Anal. Calcd. for: $C_{19}H_{19}N_6FO_4$

Method-2

A mixture of (±)-9-fluoro-2,3-dihydro-3-methyl-10-(1-piperazinyl4-cyanoguanidine)-7-oxo-7H-pyrido-[1,2,3-de]-1,4-benzoxazine-6-carboxylic acid (1.0 g) (3), (±)-9-fluoro-2,3-dihydro-3-methyl-10-(1-piperazinyl)-7-oxo-7H-pyrido [1,2,3-de]-1,4-benzoxazine-6-carboxylic acid (0.92 g) (1), n-butanol (100 mL) and a few drops of conc HCl was refluxed with stirring for 96 hours. The solvent was removed under reduced pressure and the resulting sold was dissolved in a boiling mixture of methanol and water, decolorized with charcoal, filtered, cooled and the solid was removed by filtration to give 0.04 g of (5).

m.p.>300° C. Anal. Calcd. for: $C_{36}H_{39}N_9F_2Cl_2O_9$

|  | C | H | N | F |
|---|---|---|---|---|
| Theory: | 55.07 | 4.62 | 20.28 | 4.58 |
| Found: | 54.09 | 4.73 | 19.84 | 4.17 |

|  | C | H | N | F | Cl |
|---|---|---|---|---|---|
| Theory: | 51.80 | 4.70 | 15.10 | 4.55 | 8.49 |
| Found: | 51.04 | 5.47 | 11.03 | 4.17 | 8.56 |

SPECIFIC REACTION SCHEME-XIII

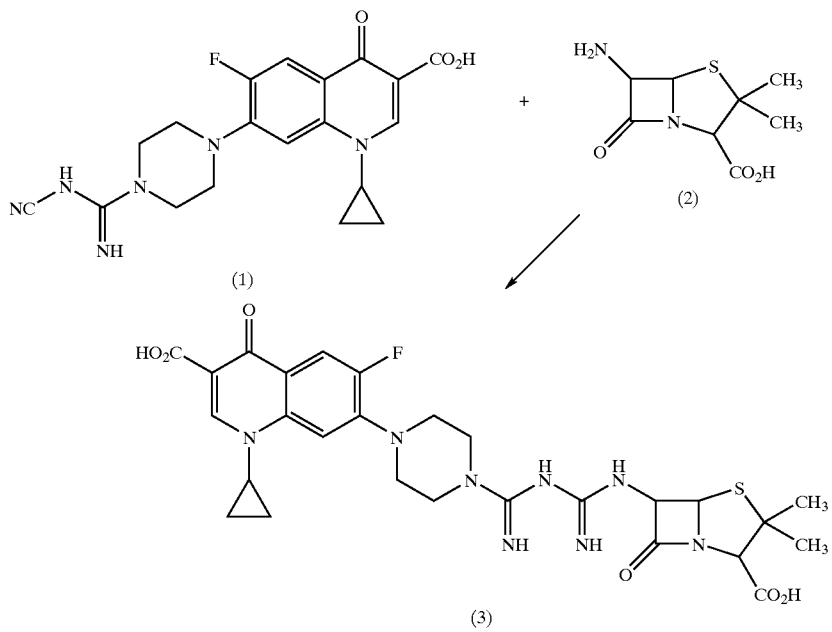

Method-1

A mixture of 1-cyclopropyl-6-fluoro-1,4-dihydro-4-oxo-7-(1-piperazinyl-4-cyanoguanidine)-3-quinolinecarboxylic acid (5 g) (1), 6-aminopenicilanic acid (2.7 g) (2), n-butanol (200 mL) and conc. HCl (1 mL) was refluxed with stirring for 24 hr. The solvent was removed under reduced pressure and the resulting solid was recrystallized twice from boiling methanol and decolorized with charcoal to yield 0.5 g of (3). Mp 290–293° C.

Anal. Calcd. for: $C_{27}H_{33}N_8FCl_2SO_6$

|  | C | H | N |
|---|---|---|---|
| Theory: | 47.17 | 4.83 | 16.29 |
| Found: | 47.28 | 5.73 | 15.16 |

SPECIFIC REACTION SCHEME XIV

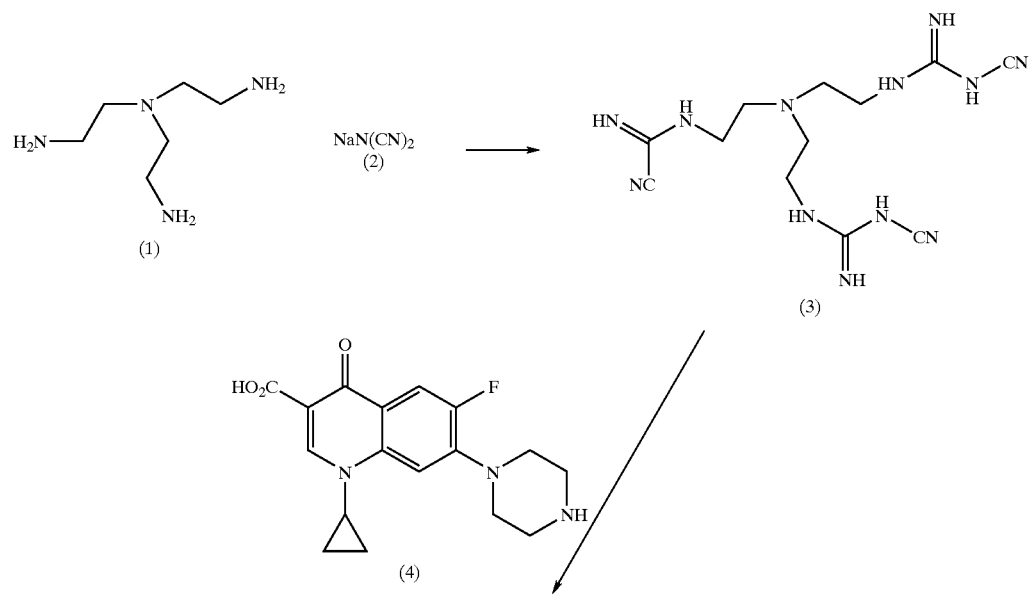

-continued

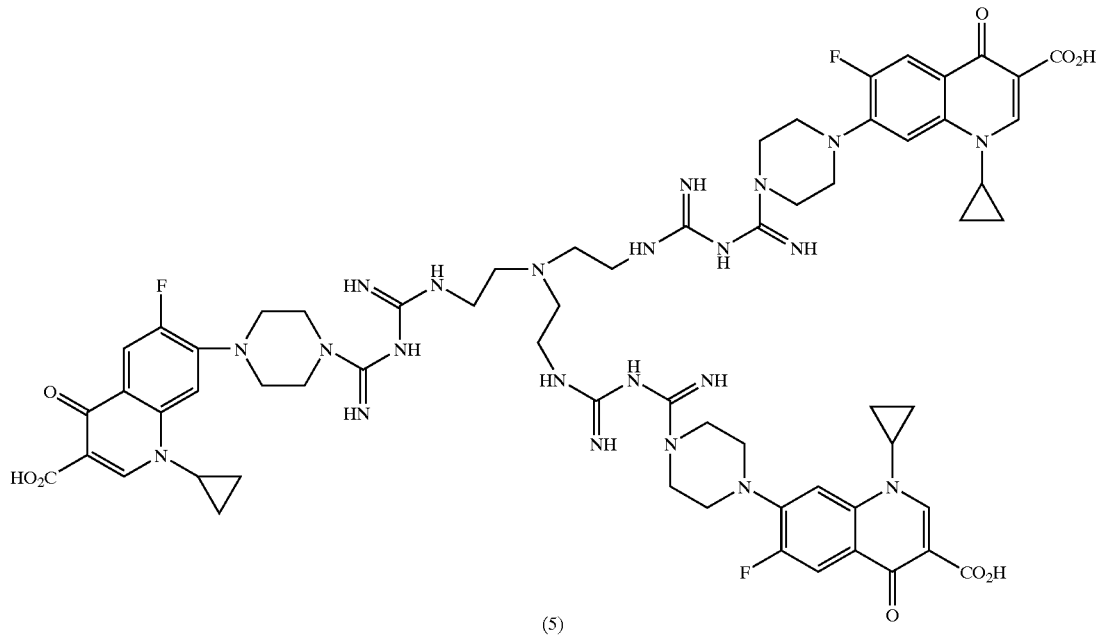

(5)

Method-1

A mixture of Tris (2-amninoethyl)amine (10 g) (1) acidified with conc HCl and sodium dicyanamide (18.16 g) was heated at 195–200° C. for 0.5 hr. It was cooled, mixed with water, acidified with conc HCl, filtered and washed with water. The resulting sticky solid was mixed with water again, basified with 10% NaoH solution, filtered, and washed with water. The sticky mass was mixed and washed with ether repeatedly when it became solid. wt. 17.7 g (3) mp. 265–270° C.

Anal. Calcd. for: $C_{12}H_{21}N_{13}$

Method-2

A thoroughly ground mixture of Tris (2-cyanoguanidinoamino ethyl) (1 g) (3), 1-cyclopropyl-6-fluoro-1,4-dihydro-4-oxo-7-(1-piperazinyl) (4) quinolinecarboxylic acid (3.16 g) (4) and a few drops of conc HCl was fused at 290–295° C. for 0.5 hr. It was cooled, dissolved in water, decolorized with activated charcoal, filtered, basified with 10% sodium carbonate solution and the precipitate was removed by filtration. The solid base was dissolved in water by acidifying with conc HCl, decolorized with charcoal again, filtered cooled and made turbid with acetone. The solid was removed by filtration to give 0.1 gm of (5). mp>300° C.

Anal. Calcd. for: $C_{63}H_{81}N_{22}F_3Cl_6O_9$

|  | C | H |
|---|---|---|
| Theory: | 41.49 | 6.09 |
| Found: | 41.56 | 6.20 |

|  | C | H | N | F | Cl |
|---|---|---|---|---|---|
| Theory: | 48.50 | 5.23 | 19.75 | 3.65 | 13.63 |
| Found: | 49.95 | 5.69 | 20.91 | 2.65 | 12.34 |

SPECIFIC REACTION SCHEME XV

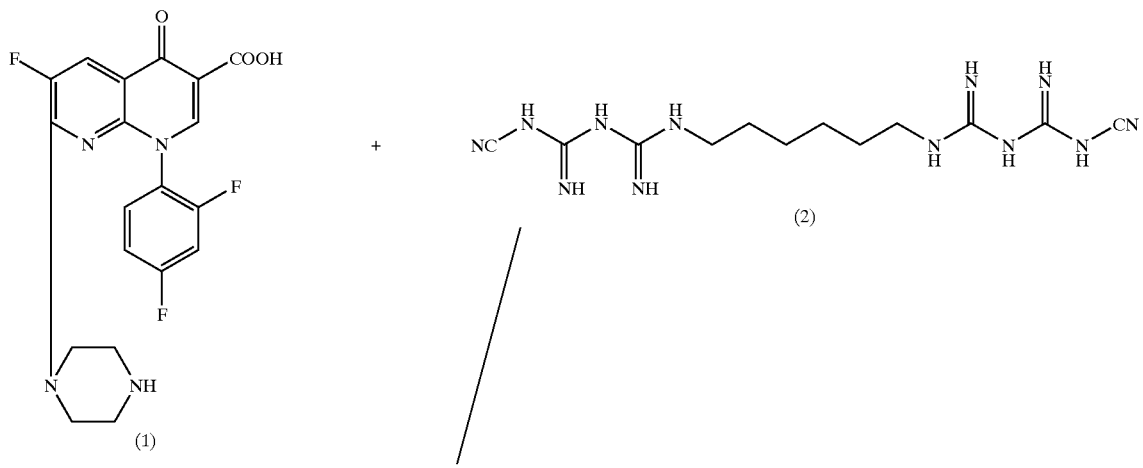

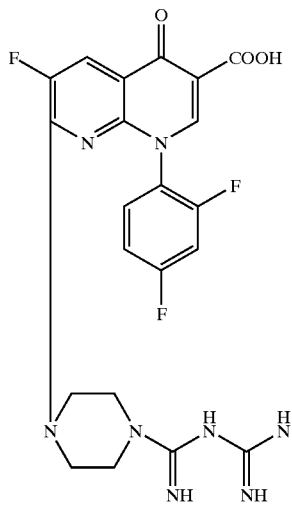
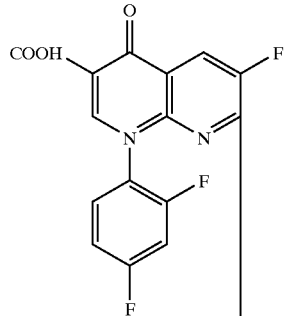

(3)
·4 HCl

Method-1

A mixture of (3.5 g.) (1), (1.08 g.) (2), n-butanol (150 mL), water (7 mL) and conc. HCL (2 mL) was refluxed with stirring for 106 hours, then evaporated to dryness. The resulting solid was washed with acetone and recrystallized twice from boiling methanol and decolorized with charcoal to yield 0.3 g. of (3).

Anal. Calcd. For :$C_{48}H_{52}N_{16}F_6Cl_4O_6$

|  | C | H | N | Cl |
|---|---|---|---|---|
| Theory: | 47.85 | 4.34 | 18.60 | 11.77 |
| Found: | 47.92 | 4.65 | 16.7 | 10.07 |

SPECIFIC REACTION SCHEME XVI

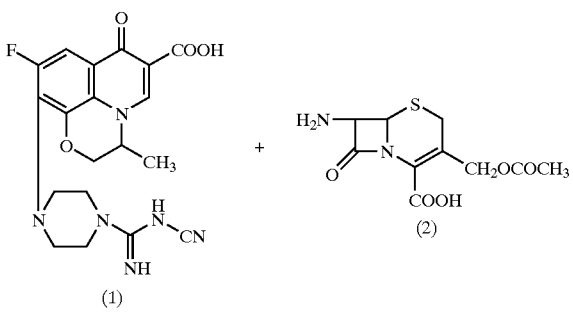

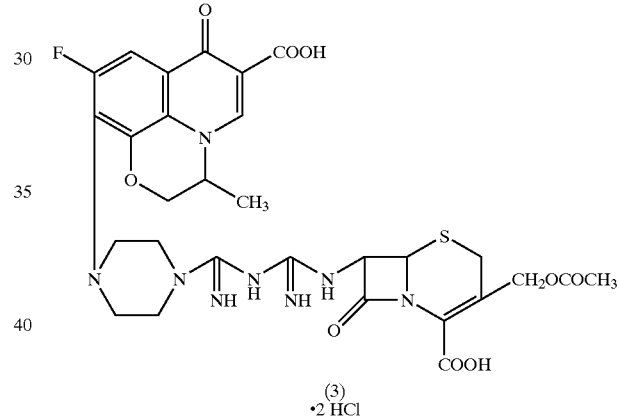

(3)
·2 HCl

Method-1

A mixture of (±)-9-Fluoro-2,3-dihydro-3-methyl-10(4-cyanoguanidino-1-piperazinyl)-7-oxo-7H-pyrido 1,2,3-de-1,4-benzoxazine-6-carboxylic acid (1.5 g)(1), 7-amino cephalosporanic acid (1 g.) (2), n-butanol (100 mL) and conc. HCl (0.5 mL) was refluxed with stirring for 29 hr. It was cooled on ice and the solid was removed by filtration. It was washed with acetone and the resulting solid was recrystallized twice from boiling methanol and decolorized with charcoal to give 0.08 g. of (3).

Anal. Calcd. for :$C_{29}H_{33}N_8FCl_2SO_9$

|  | C | H | N | F |
|---|---|---|---|---|
| Theory: | 45.55 | 4.35 | 14.65 | 2.48 |
| Found: | 46.84 | 5.26 | 14.62 | 3.87 |

Tables I–IV below list additional preferred cyclam and bicyclam derivatives within the scope of the present invention. In the tables, the "structure" column refers to the numbered structures depicted following the tables.

TABLE I

| Structure | n | X | Y | R | |
|---|---|---|---|---|---|
| 1, 2, 3, 4, 5, 6, 7, 8, 14<br>9, 10, 12, 15<br>11, 13, 16 | 1–6 | N, CH,<br>C-CH₃,<br>C-OCH₃,<br>C—F | H,<br>Br, Cl<br>F, NO₂<br>Alkyl | | |
| 1, 2, 3, 4, 5, 6, 7, 8, 14<br>9, 10, 12, 15<br>11, 13, 16 | 1–6 | N, CH,<br>C-CH₃,<br>C-OCH₃,<br>C—F | H,<br>Br, Cl<br>F, NO₂<br>Alkyl | | |
| 1, 2, 3, 4, 5, 6, 7, 8, 14<br>9, 10, 12, 15<br>11, 13, 16 | 1–6 | N, CH,<br>C-CH₃,<br>C-OCH₃,<br>C—F | H,<br>Br, Cl<br>F, NO₂<br>Alkyl | | |
| 1, 2, 3, 4, 5, 6, 7, 8, 14<br>9, 10, 12, 15<br>11, 13, 16 | 1–6 | | H,<br>Br, Cl<br>F, NO₂<br>Alkyl | | |

TABLE II

| Structure | n | X | Y | R |
|---|---|---|---|---|
| 1, 2, 3, 4, 5, 6, 7, 8, 14 9, 10, 12, 15 11, 13, 16 | 1–6 | N, CH, C-CH$_3$, C-OCH$_3$, C—F | H, Br, Cl F, NO$_2$ Alkyl | |
| 1, 2, 3, 4, 5, 6, 7, 8, 14 9, 10, 12, 15 11, 13, 16 | 1–6 | N, CH, C-CH$_3$, C-OCH$_3$, C—F | H, Br, Cl F, NO$_2$ Alkyl | |
| 1, 2, 3, 4, 5, 6, 7, 8, 14 9, 10, 12, 15 11, 13, 16 | 1–6 | N, CH, C-CH$_3$, C-OCH$_3$, C—F | H, Br, Cl F, NO$_2$ Alkyl | |

TABLE III

| Structure | n | X | Y | R |
|---|---|---|---|---|
| 1, 2, 3, 4, 5, 6, 7, 8, 14 9, 10, 12, 15 11, 13, 16 | 1–6 | N, CH, C-CH$_3$, C-OCH$_3$, C—F | H, Br, Cl F, NO$_2$ Alkyl | |

TABLE III-continued

| Structure | n | X | Y | R |
|---|---|---|---|---|
| 1, 2, 3, 4, 5, 6, 7, 8, 14 9, 10, 12, 15 11, 13, 16 | 1–6 | | Br, Cl F, NO$_2$ Alkyl | |
| 1, 2, 3, 4, 5, 6, 7, 8 9, 10, 12, 15 11, 13, 16 | 1–6 | N, CH, C-CH$_3$, C-OCH$_3$, C—F | Br, Cl F, NO$_2$ Alkyl | |
| 1, 2, 3, 4, 5, 6, 7, 8, 14 9, 10, 12, 15 11, 13, 16 | 1–6 | | Br, Cl F, NO$_2$ Alkyl | |

TABLE IV

| Structure | n | X | Y | R |
|---|---|---|---|---|
| 1, 2, 3, 4, 5, 6, 7, 8, 14 9, 10, 12, 15 11, 13, 16 | 1–6 | N, CH, C-CH$_3$, C-OCH$_3$, C—F | H, I, Br, Cl F, NO$_2$ alkyl | |

TABLE IV-continued
| Structure | n | X | Y | R |
|---|---|---|---|---|
| 1, 2, 3, 4, 5, 6, 7, 8, 14<br>9, 10, 12, 15<br>11, 13, 16 | 1–6 | N, CH,<br>C-CH$_3$,<br>C-OCH$_3$,<br>C—F | Br, Cl<br>F, NO$_2$<br>alkyl<br>I | 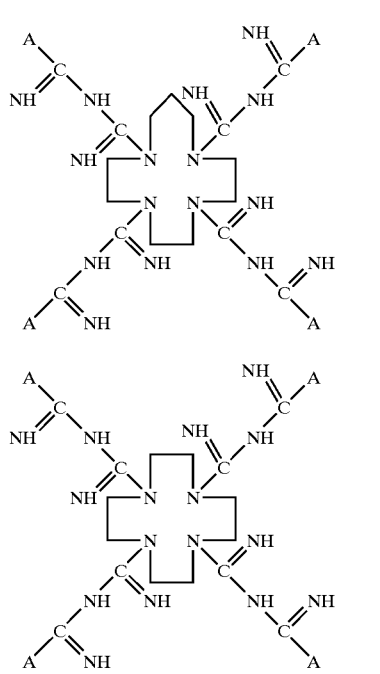 |
| | | N, CH,<br>C-CH$_3$,<br>C-OCH$_3$,<br>C—F | Br, Cl,<br>F, NO$_2$,<br>I, alkyl | 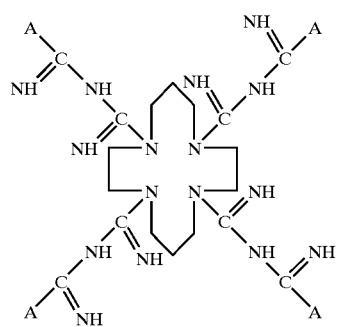 |
| | | | Br, Cl<br>F, NO$_2$,<br>I, alkyl | 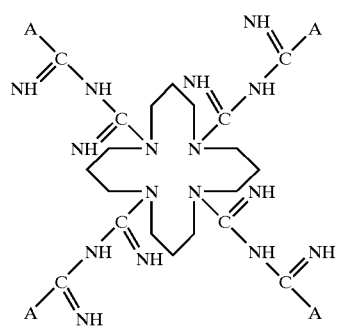 |
STRUCTURE 1
STRUCTURE 2
STRUCTURE 3
STRUCTURE 4

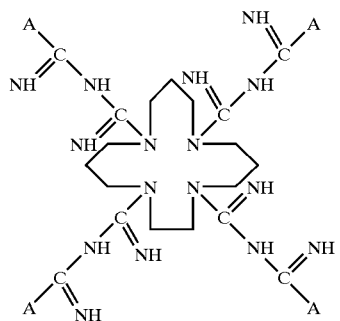
STRUCTURE 5
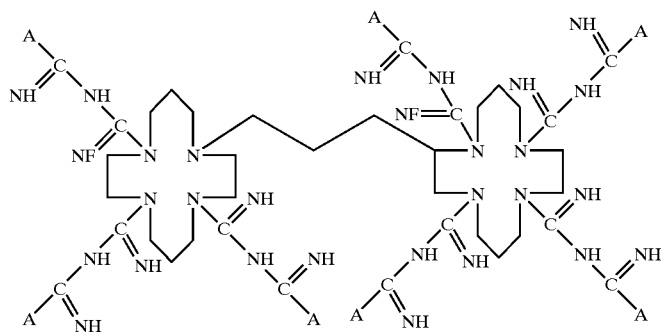
STRUCTURE 6
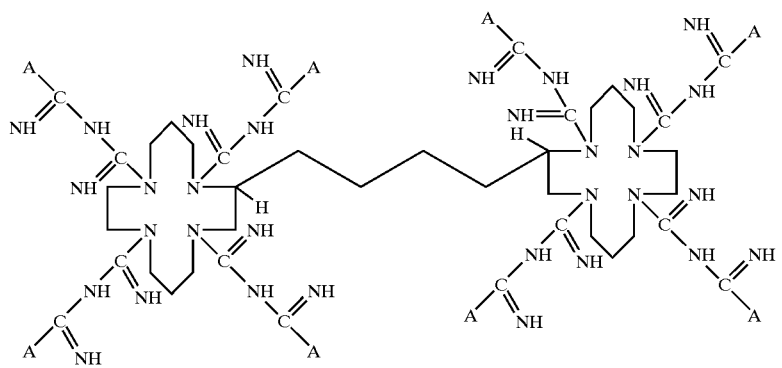
STRUCTURE 7
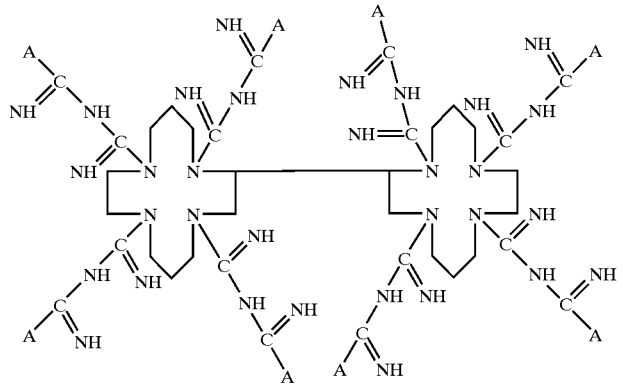
STRUCTURE 8

-continued
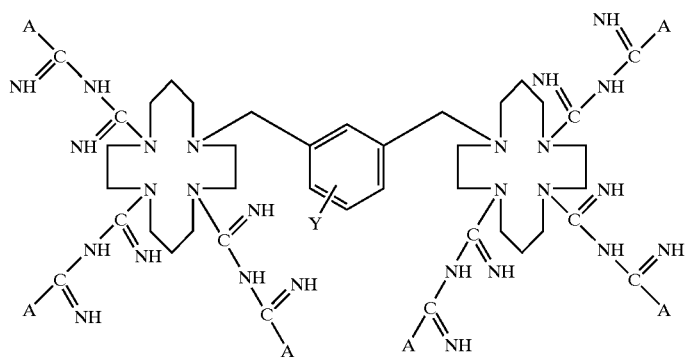
STRUCTURE 9
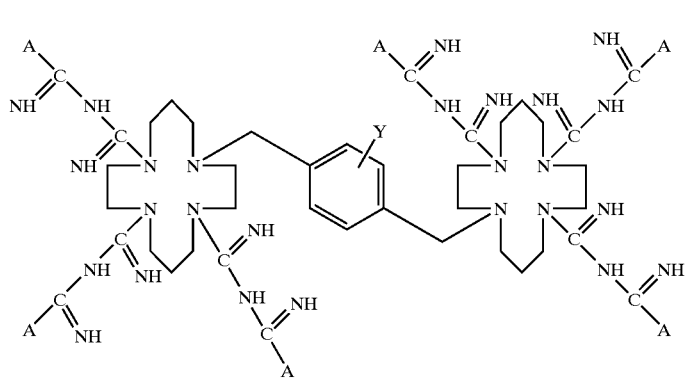
STRUCTURE 10
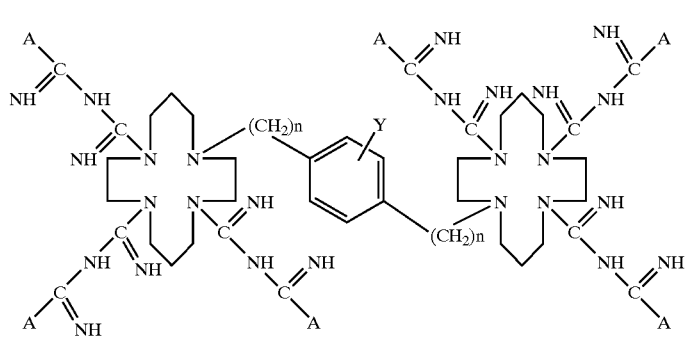
STRUCTURE 11
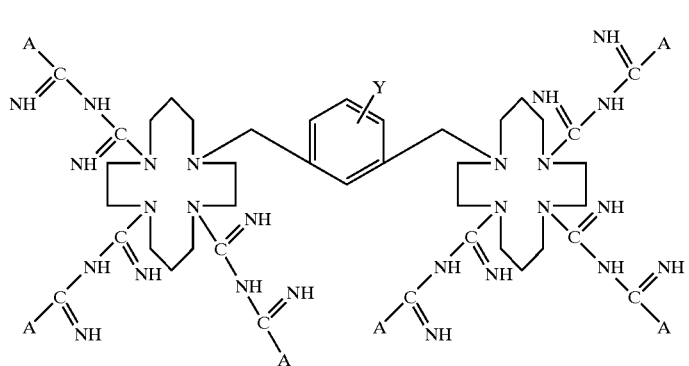
STRUCTURE 12

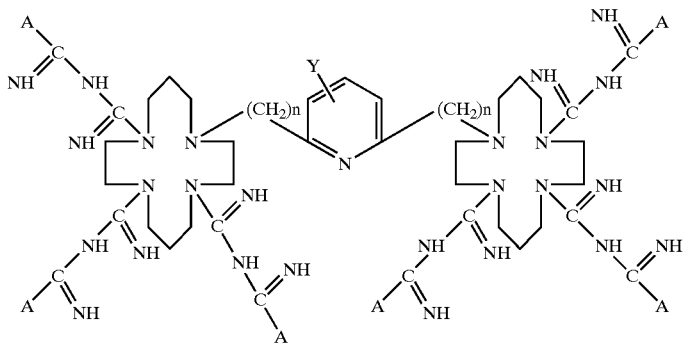
STRUCTURE 13
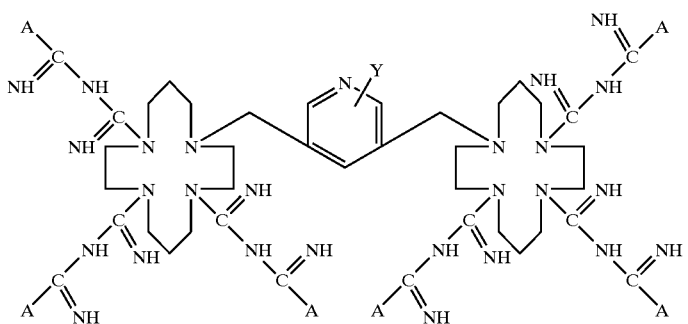
STRUCTURE 14
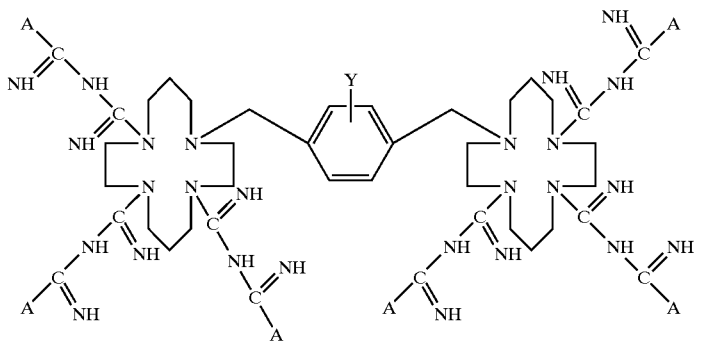
STRUCTURE 15
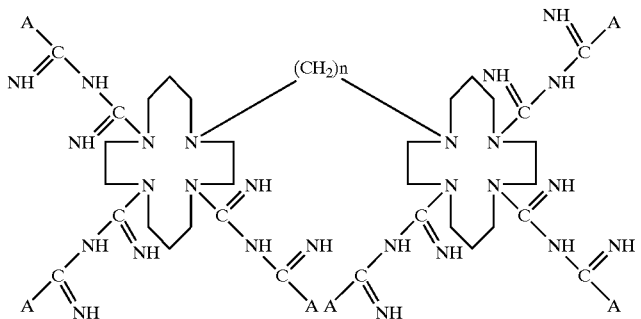
STRUCTURE 16

-continued

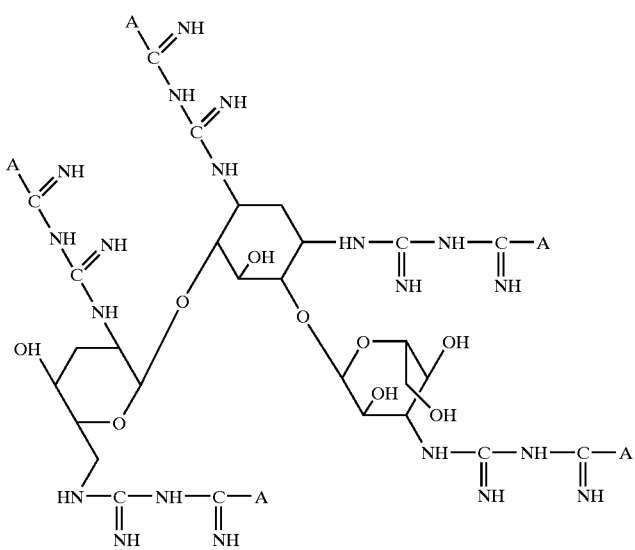

(VII)

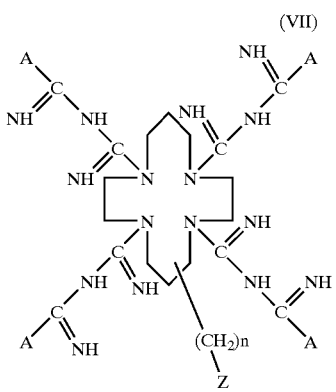

STRUCTURE 17

STRUCTURE 18

Compounds of the general structure (VIII) depicted above may be synthesized, for example, by reacting a suitable cyclam starting material with sodium dicyandiamide to form an intermediate, then reacting the intermediate with the desired antibacterial group(s) to form the final product. The reaction scheme below is an example of such a synthesis:

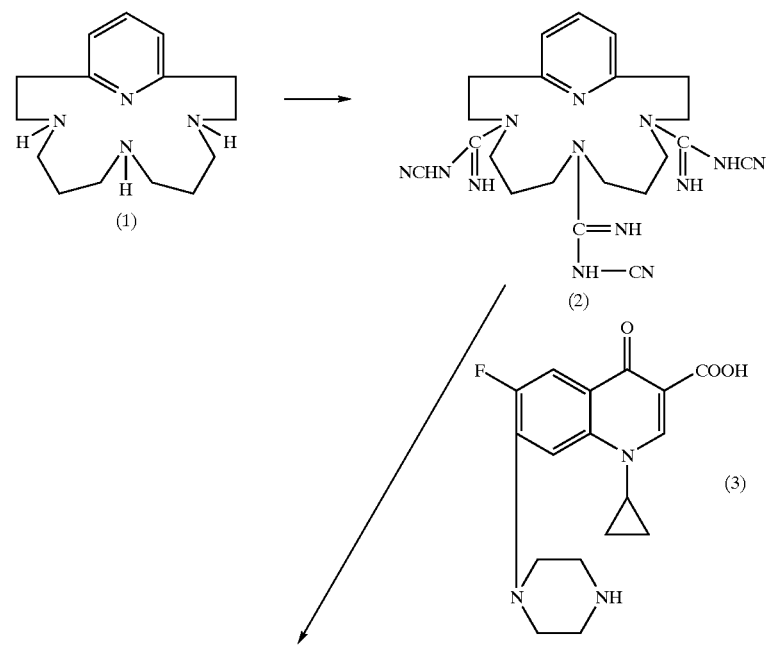

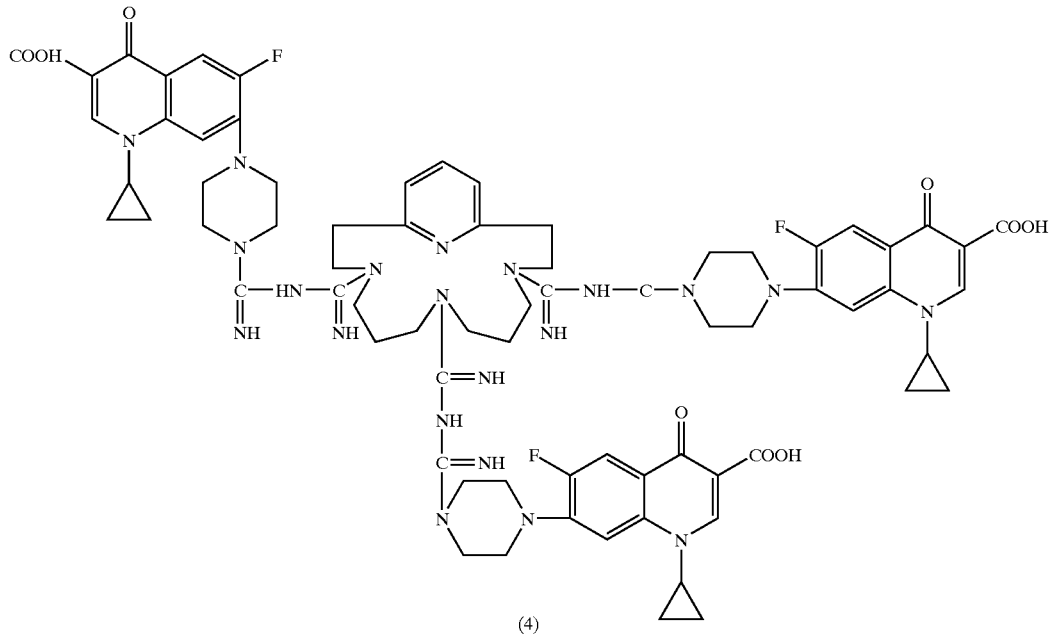
(4)
Compounds of the general structure (IX) depicted above may be synthesized in similar fashion using the appropriate bicyclam starting material. An example is depicted below.
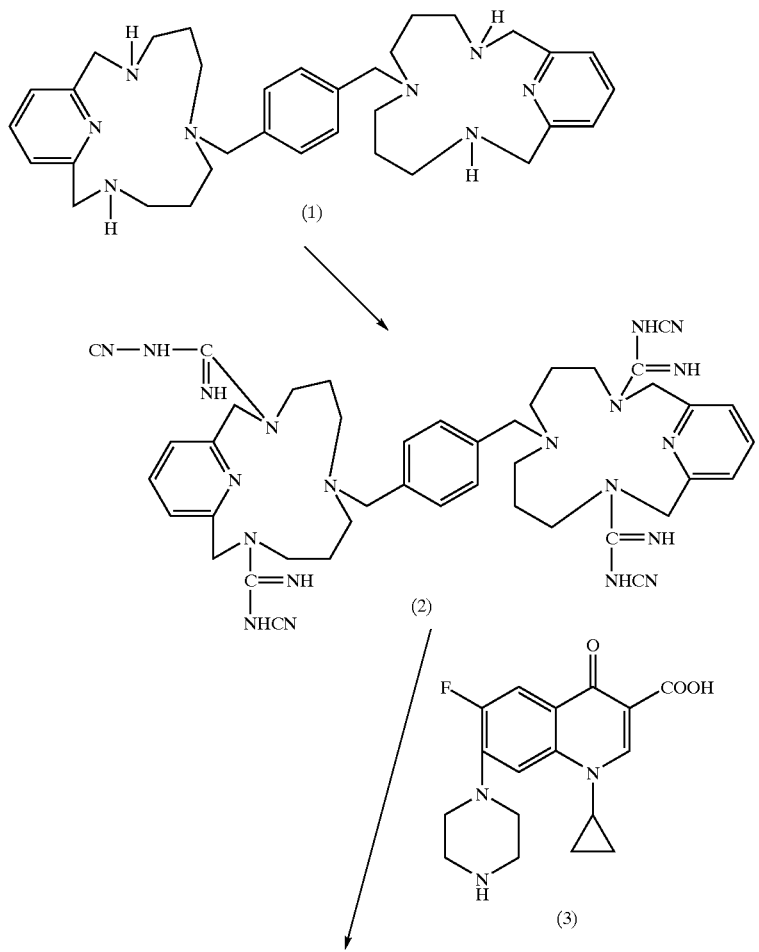

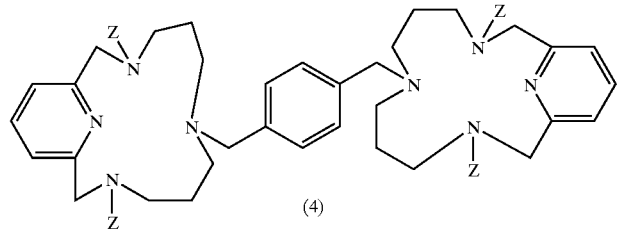

(4)

where each Z is

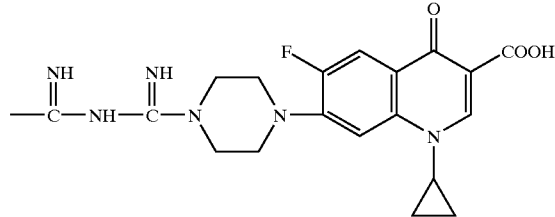

Compounds of the general structure (VII) depicted above may be synthesized in similar fashion using, for example, tobramycin as a starting material, which may be reacted with sodium dicyandiamide to give an intermediate product, which may then be reacted with the desired "A" group to form the final product.

Other specific compounds according to the present invention include:

1.

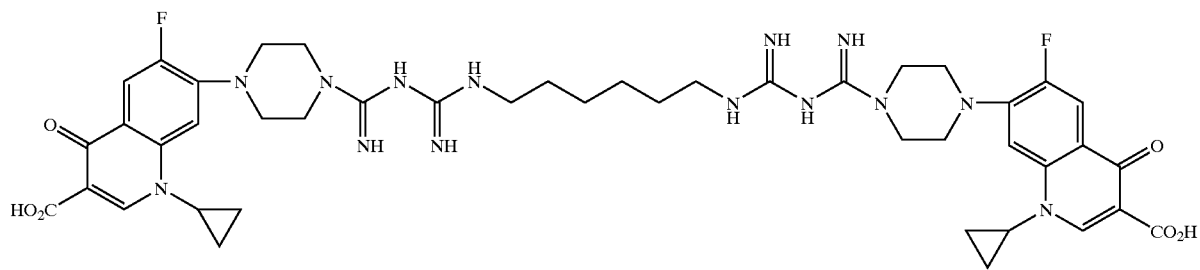

BVS-10A

2.

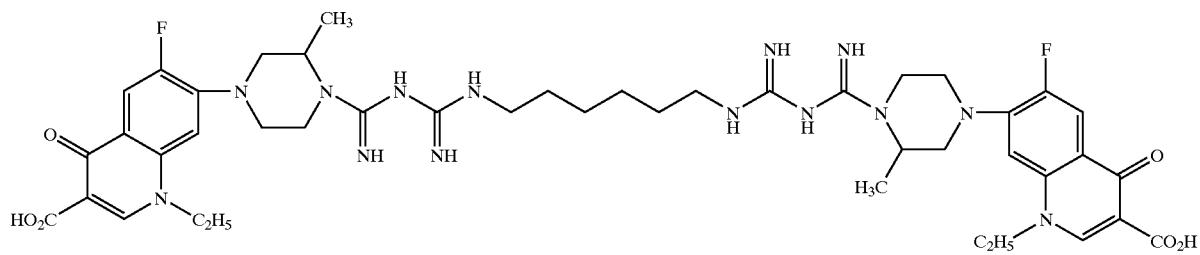

3.

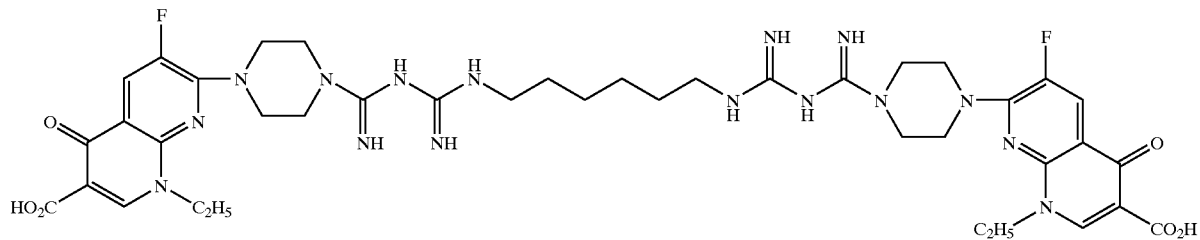

-continued
4. 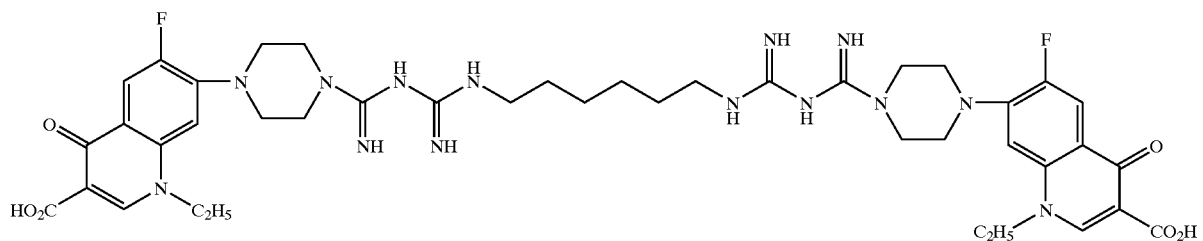
5. 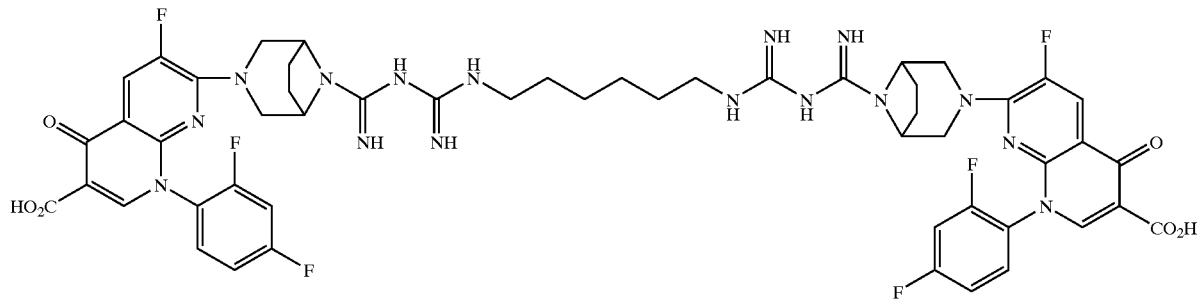
6. 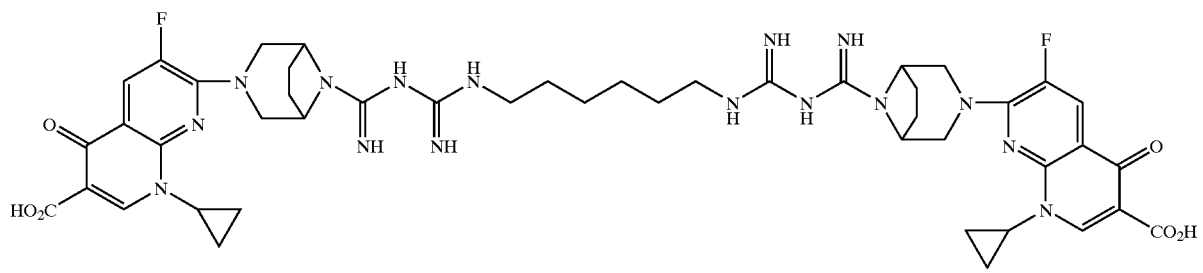
7. 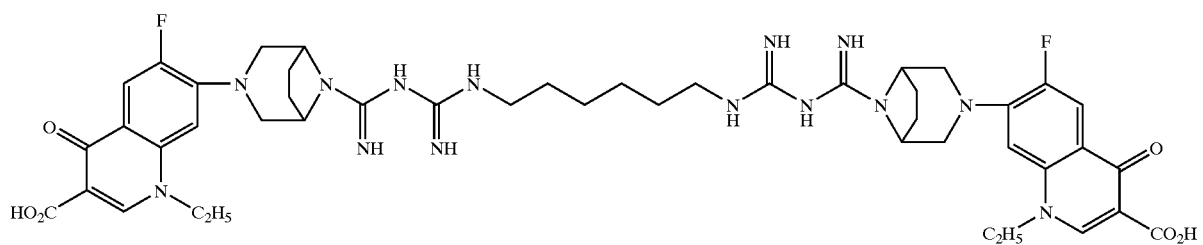
8. 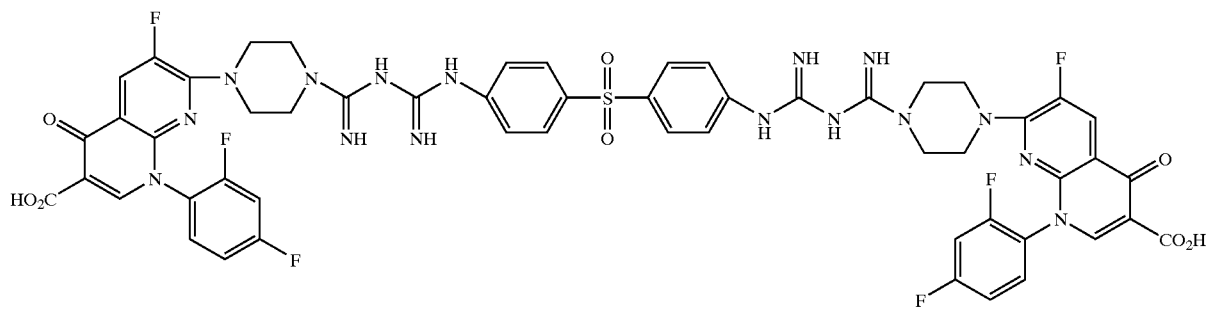

-continued
9.
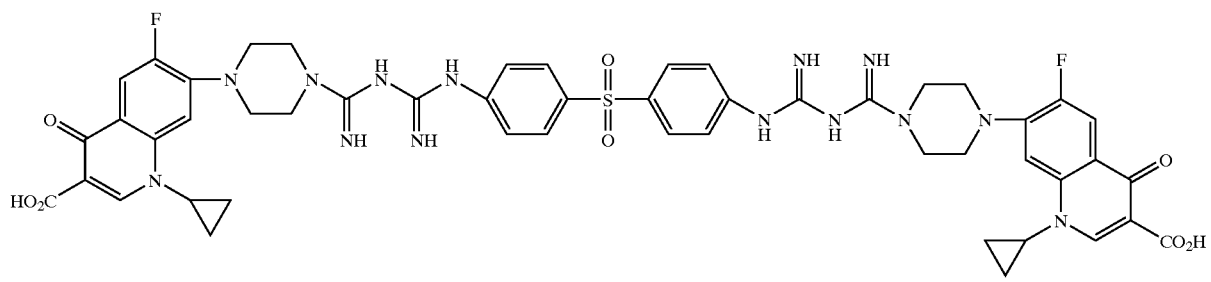
10.
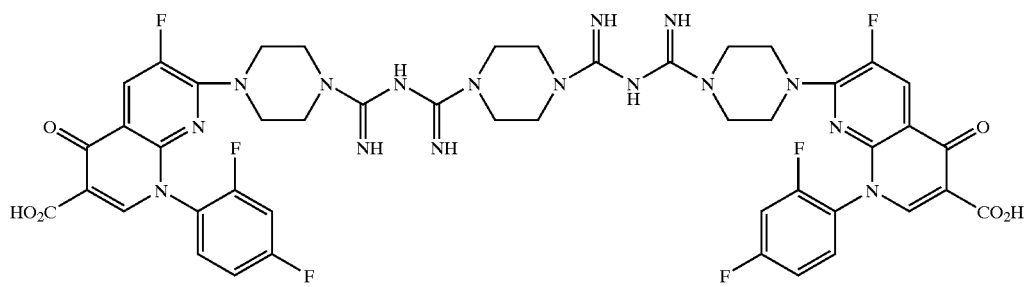
11.
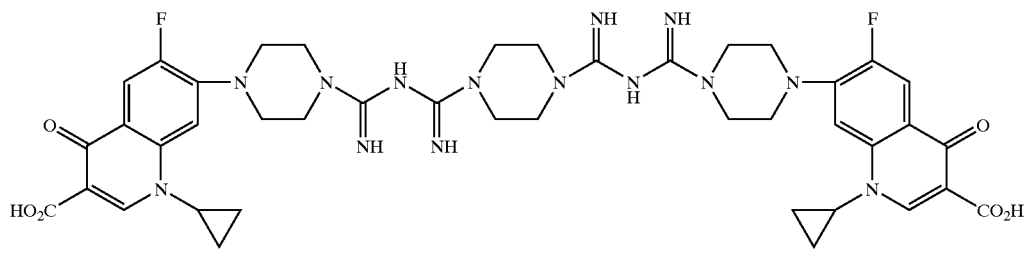
12.
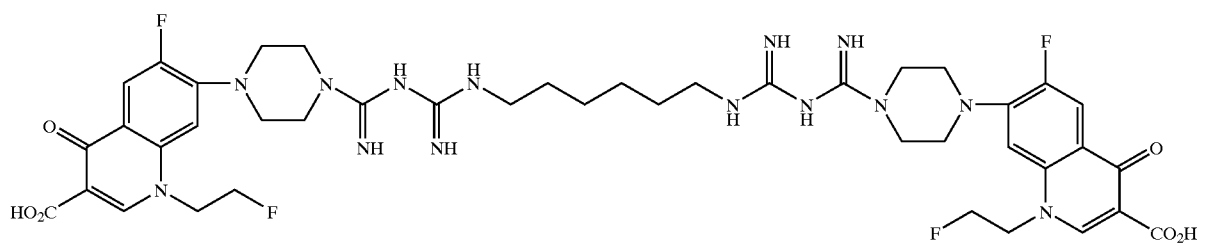
13.
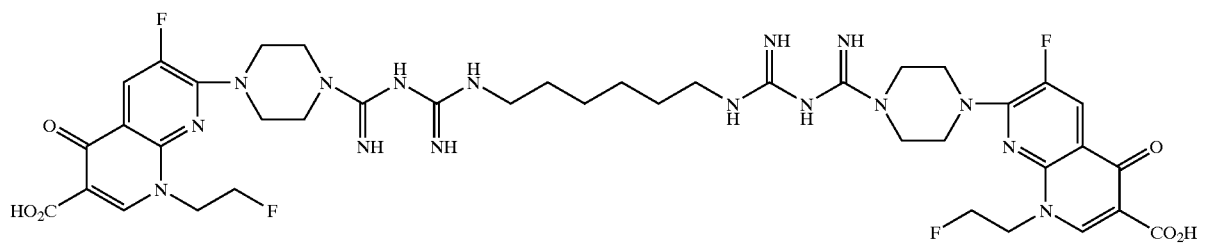

14.
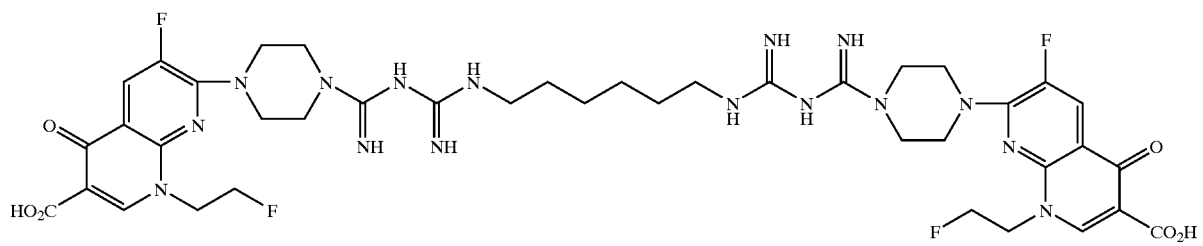
15.
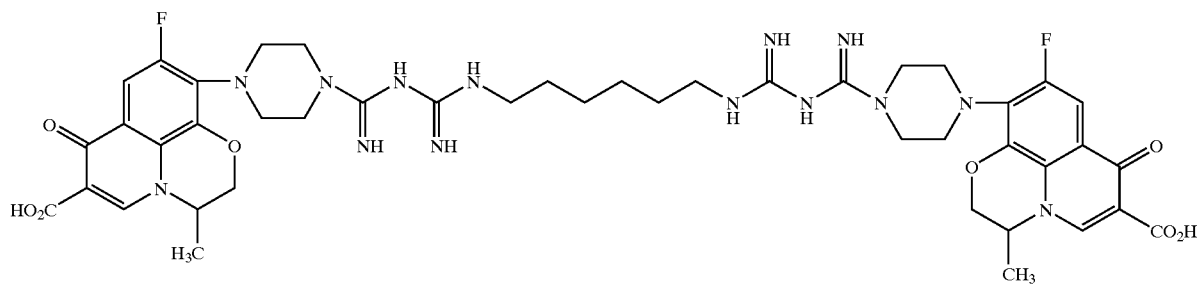
16.
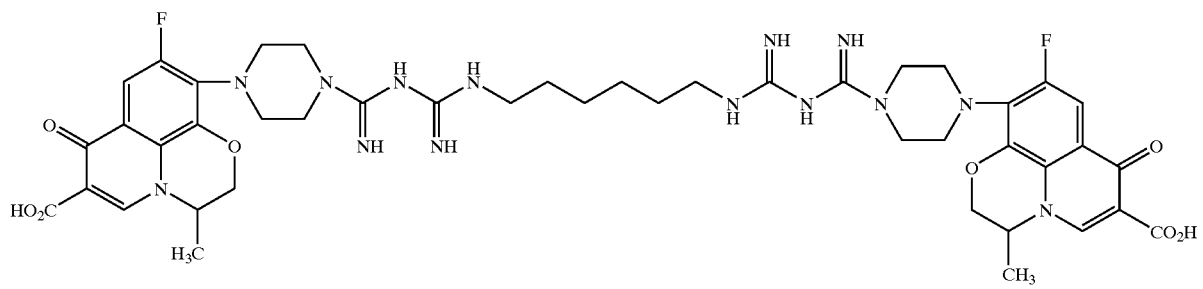
17.
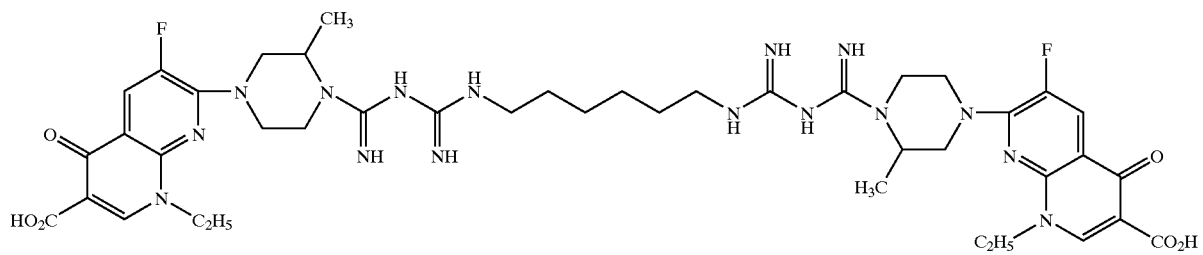
18.
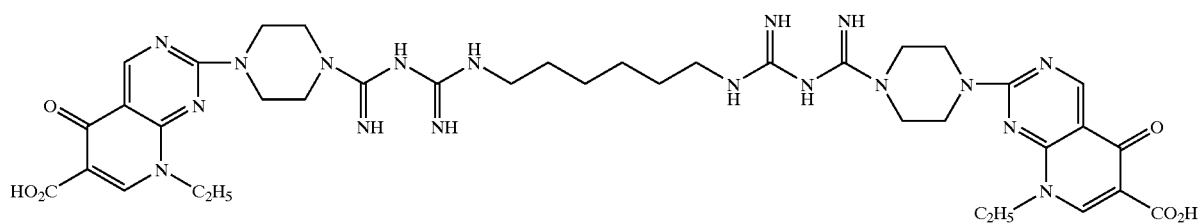

19.
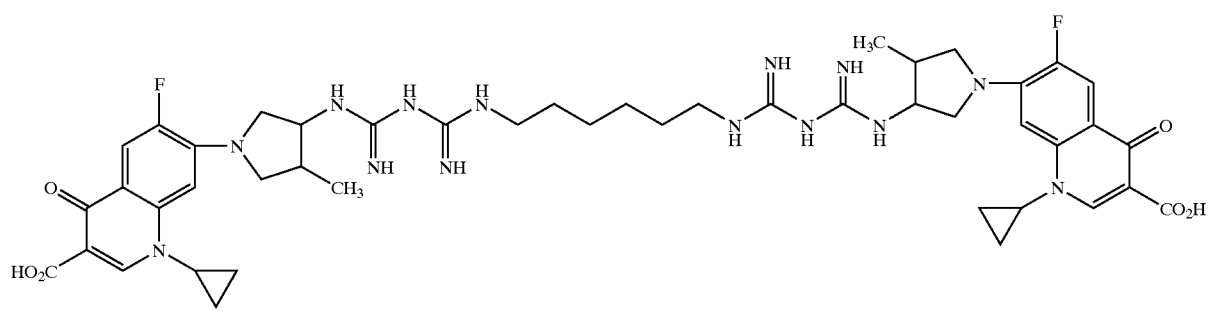
20.
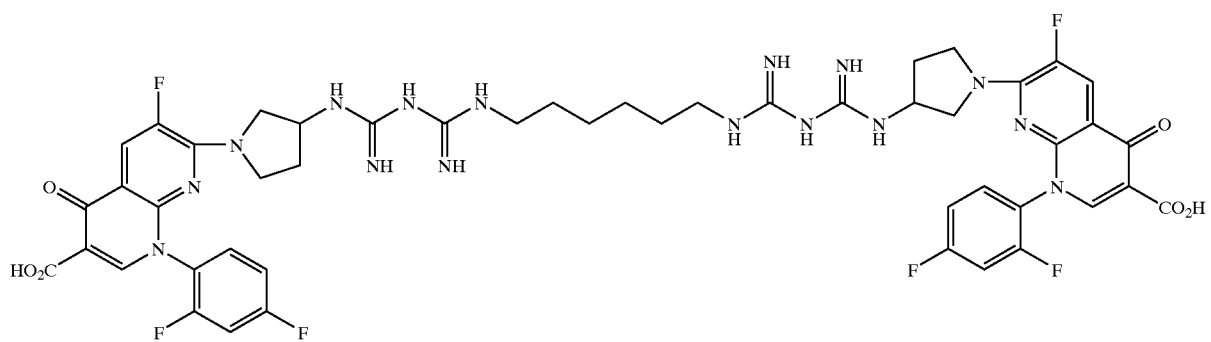
21.
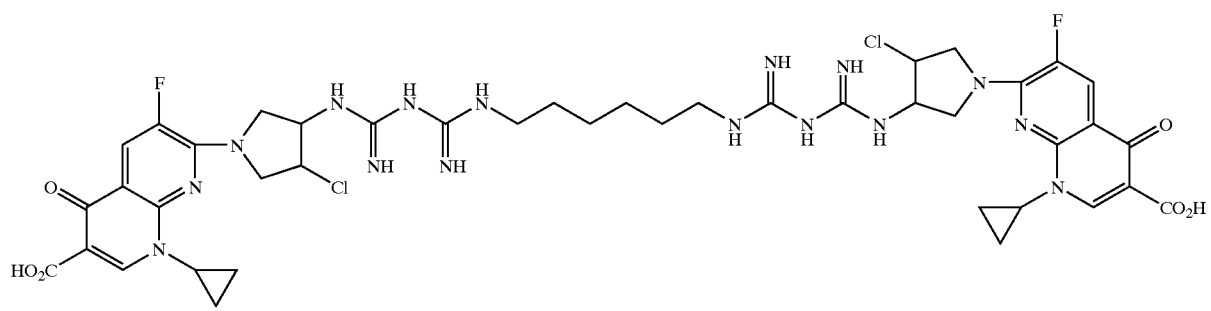
22.
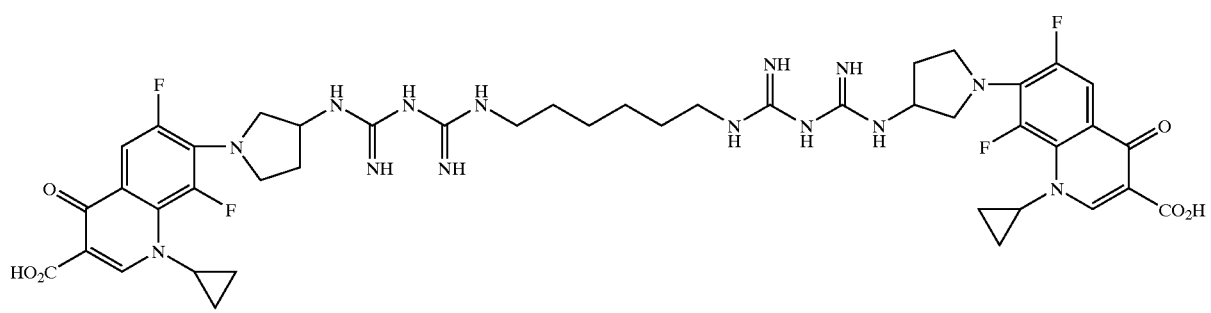
23.
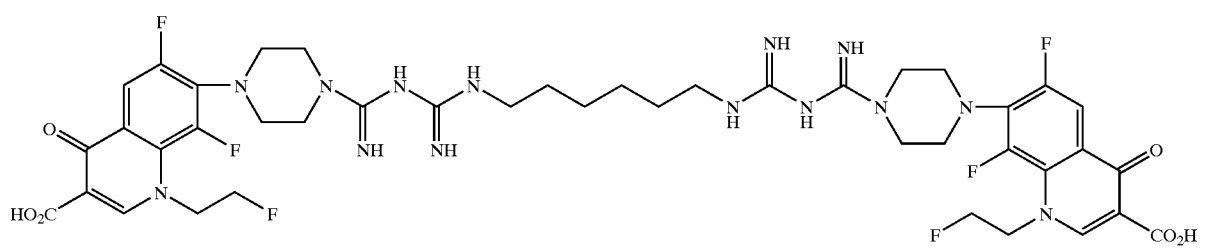

24.
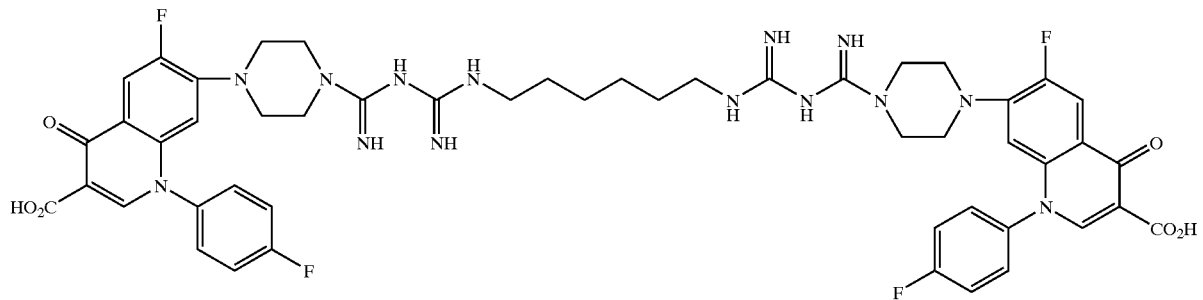
25.
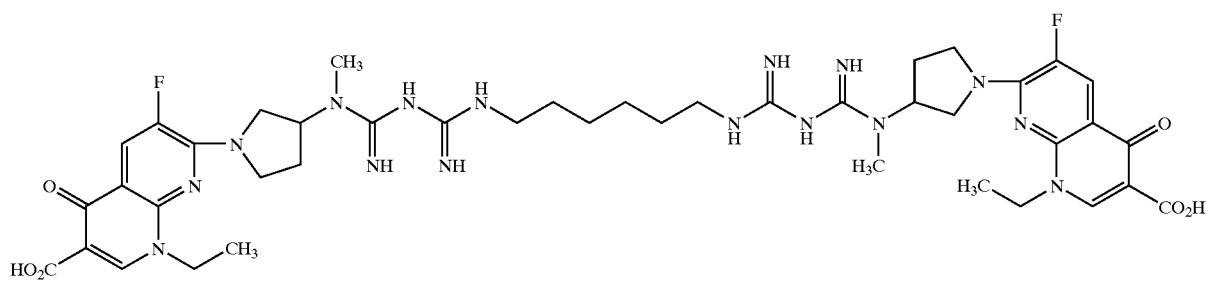
26.
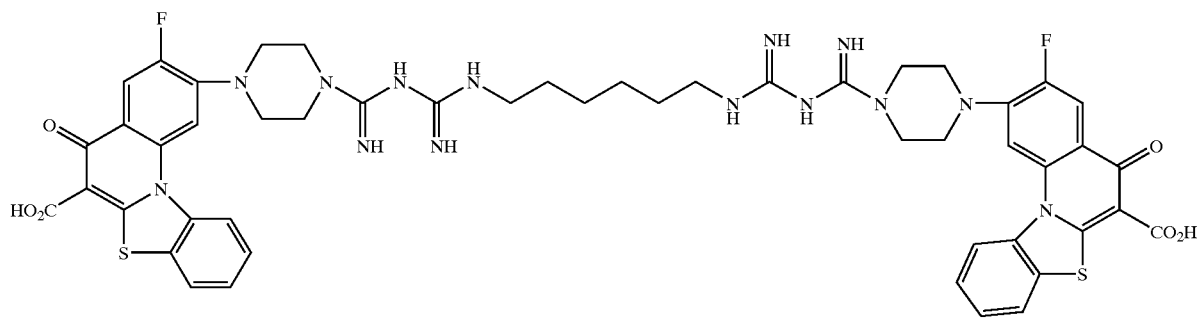
27.
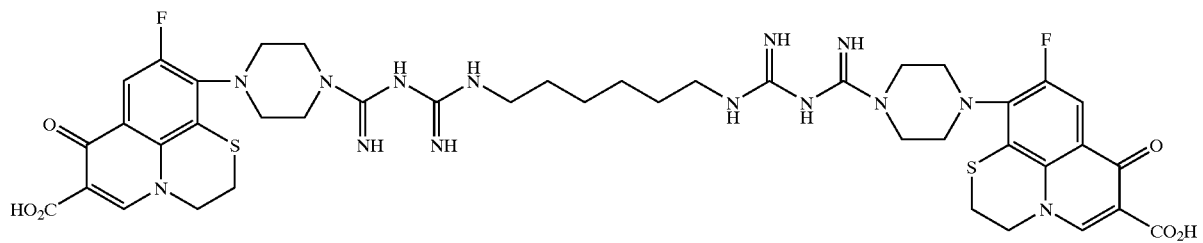
28.
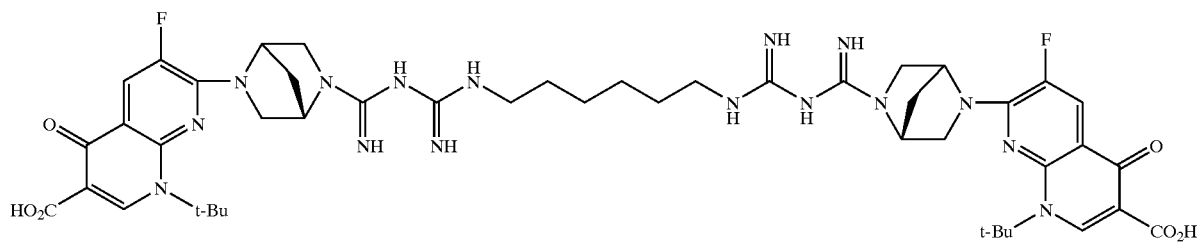

-continued
29.
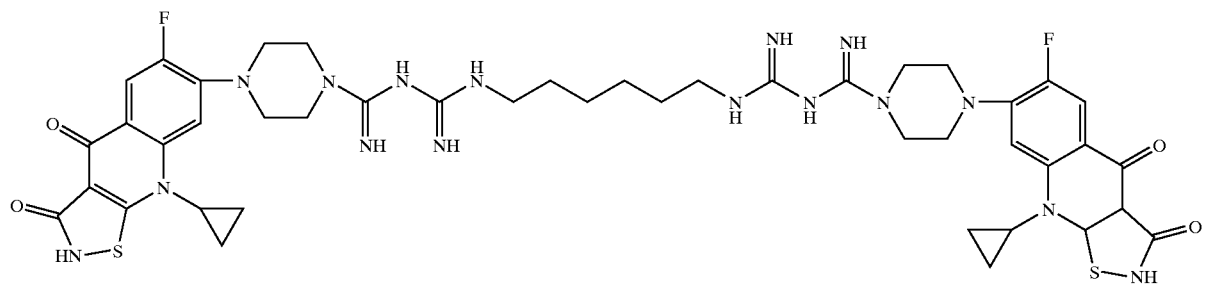
30.
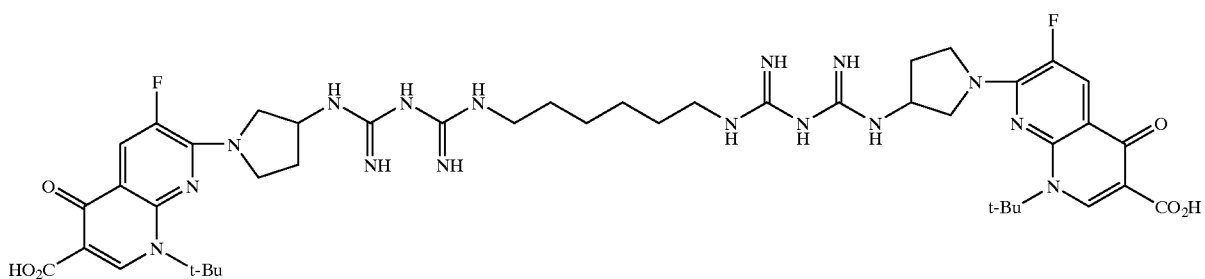
31.
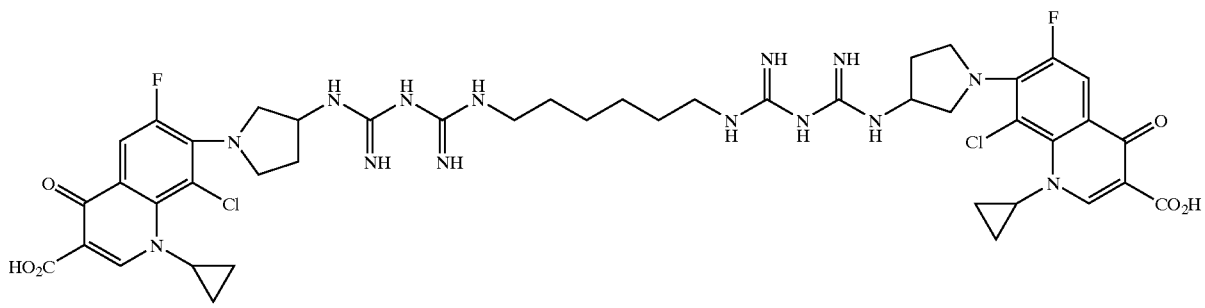
32.
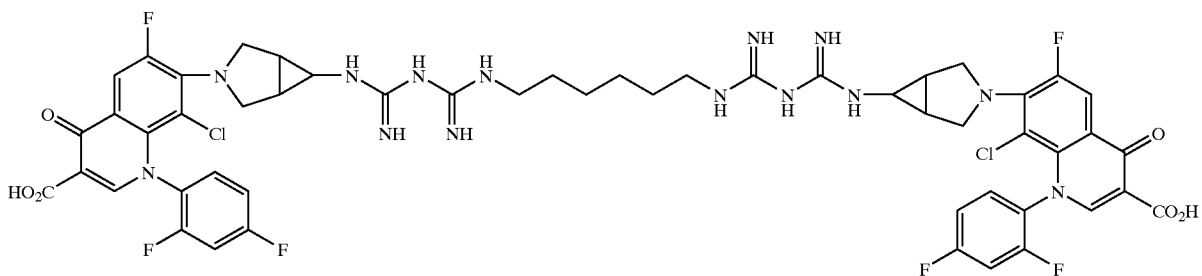
33.
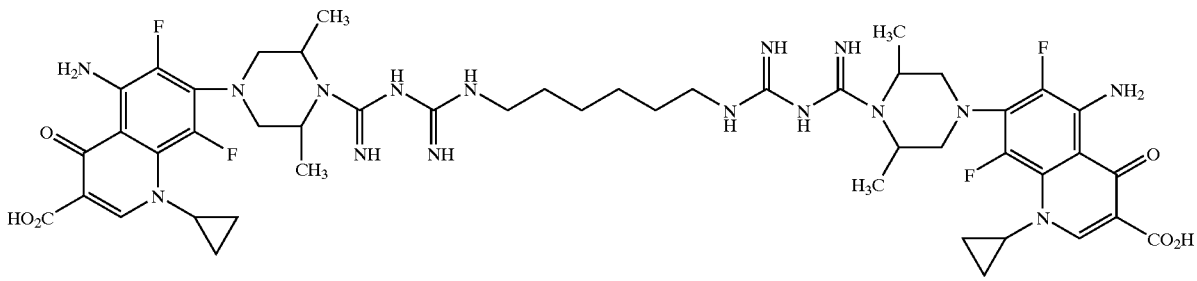

34.
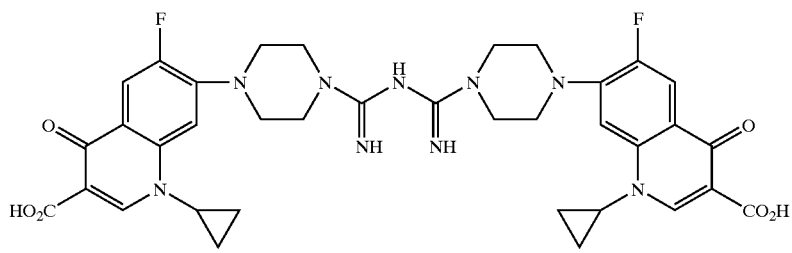
35.
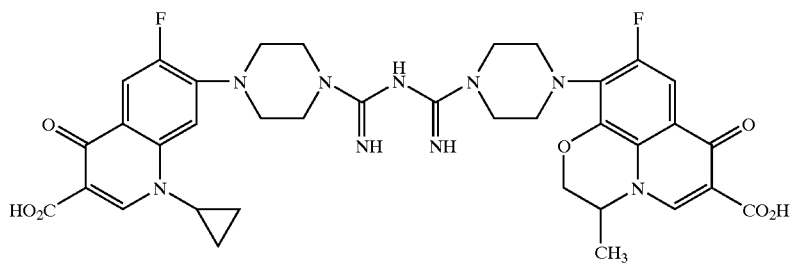
36.
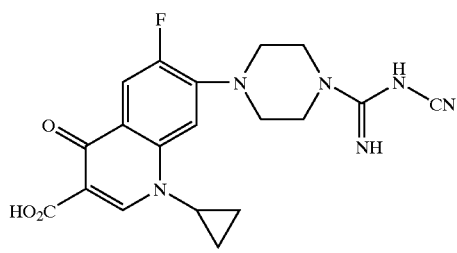
37.
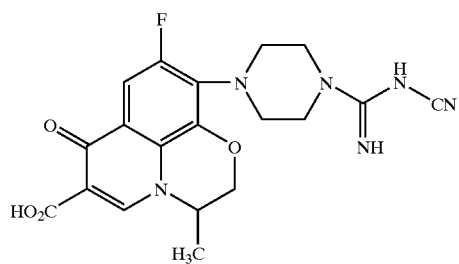
38.
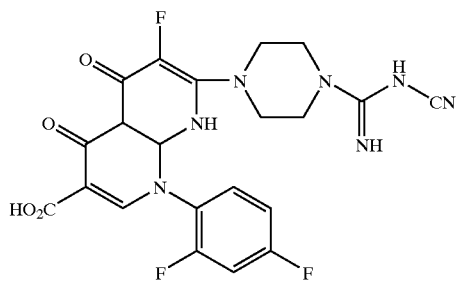
39.
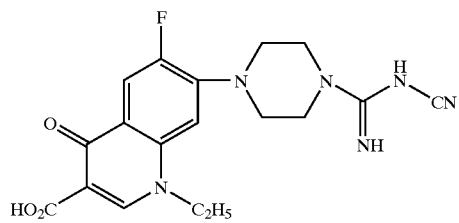

40.
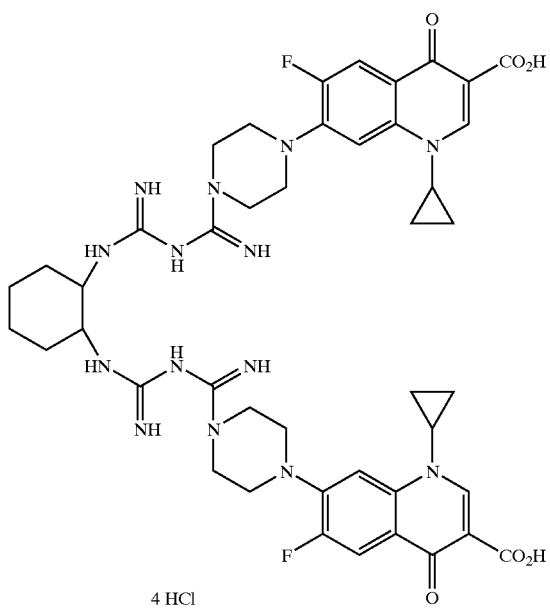
4 HCl
41.
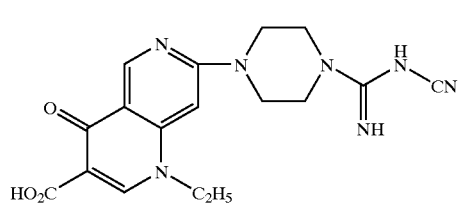
42.
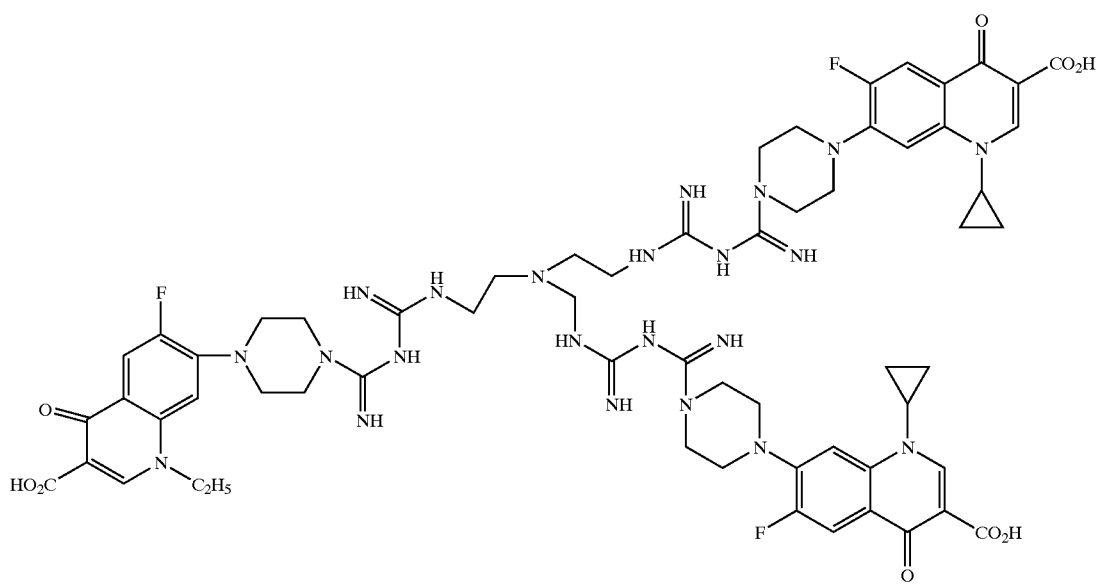
43.
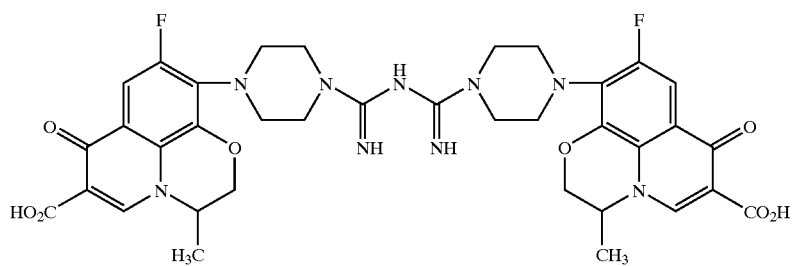

44.
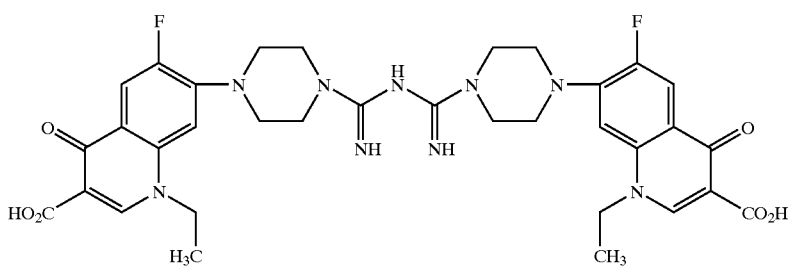
45.
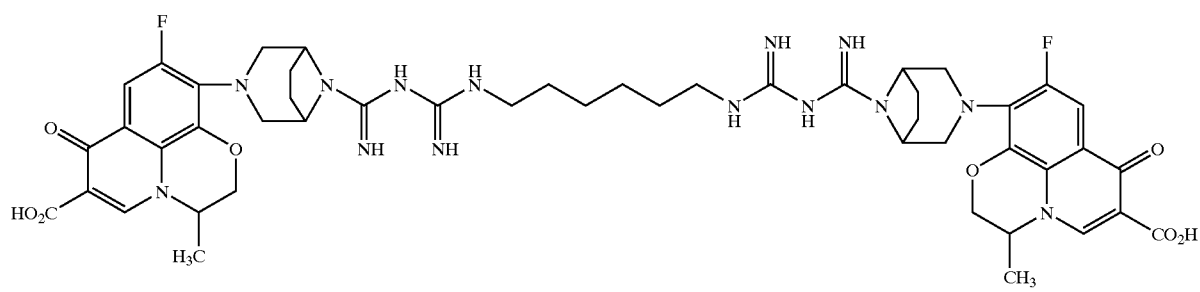
46.
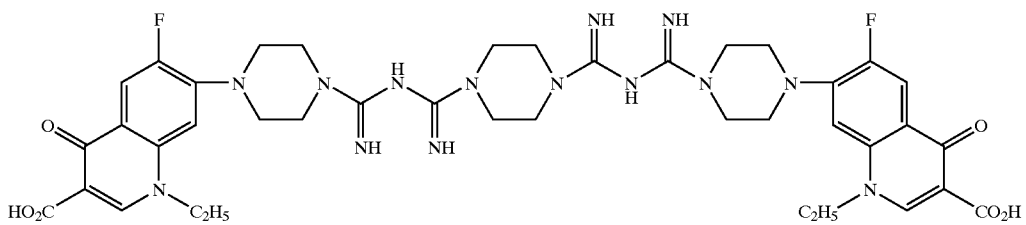
47.
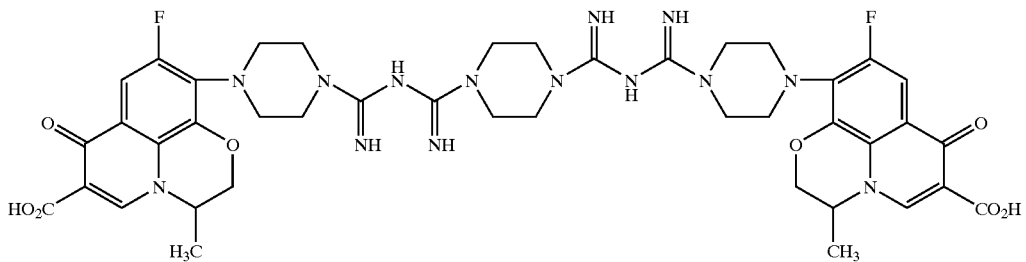
48.
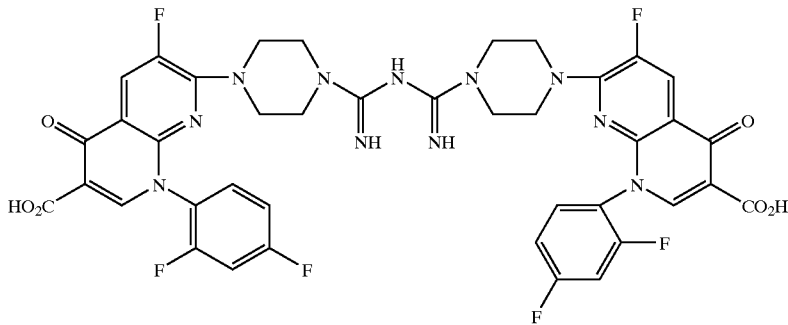

-continued
49.
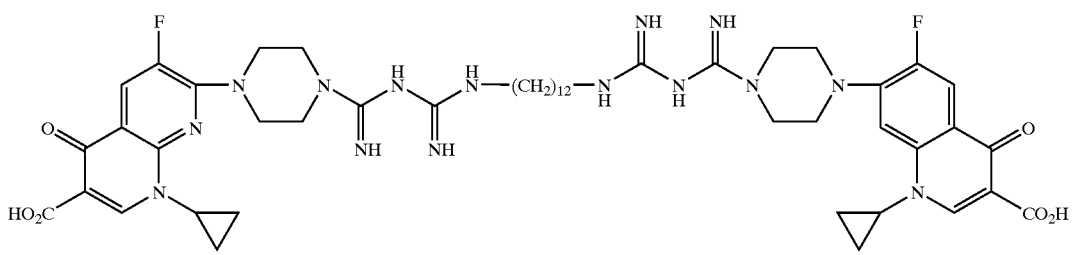
50.
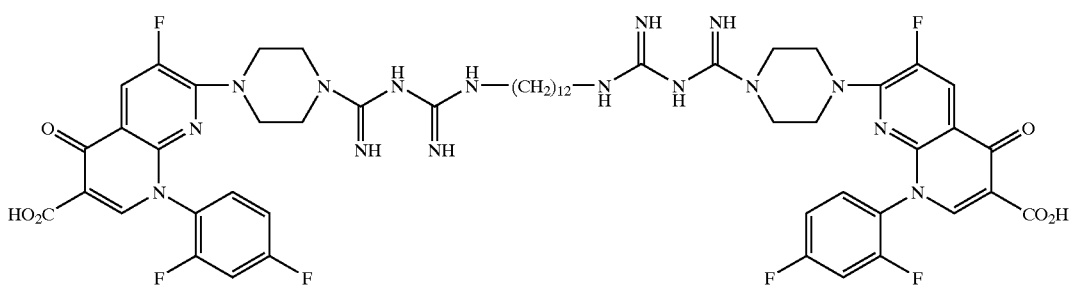
51.
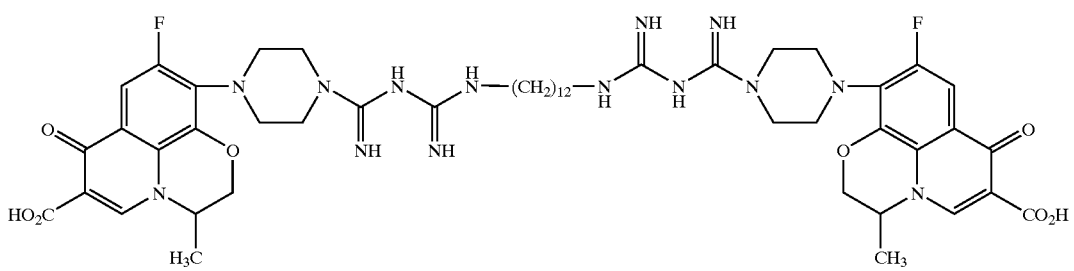
52.
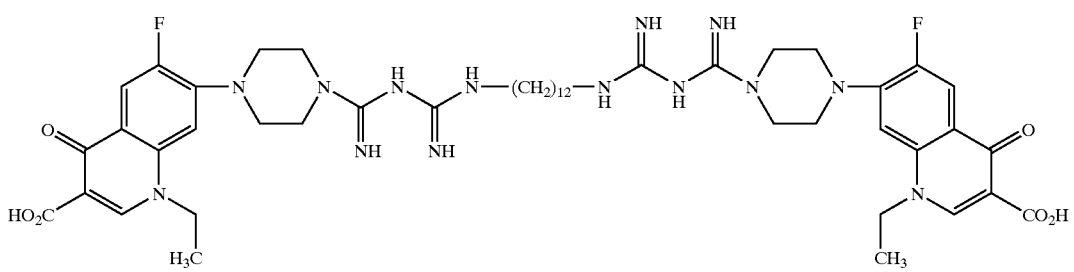
53.
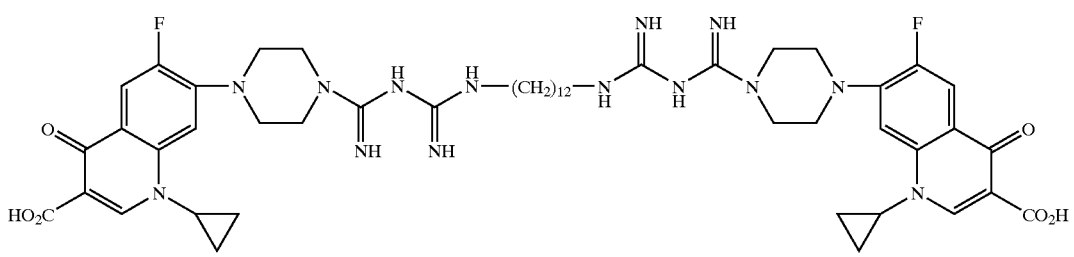

54.
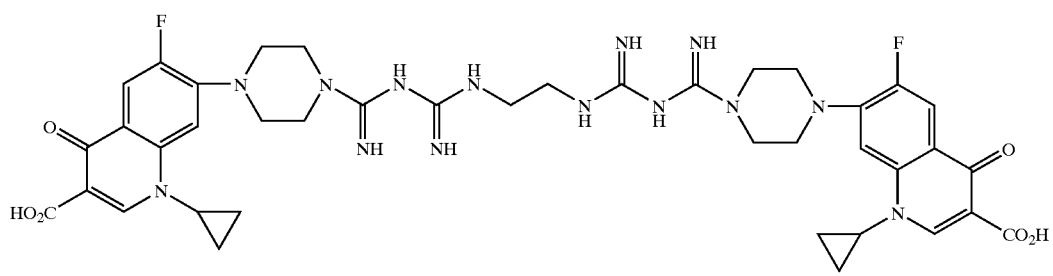
55.
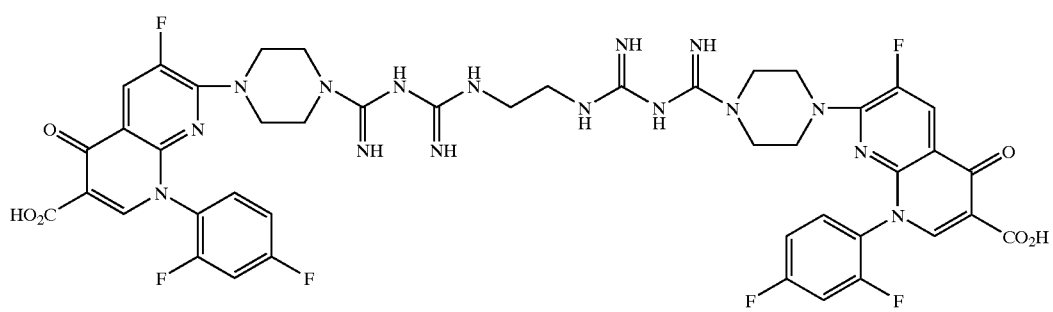
56.
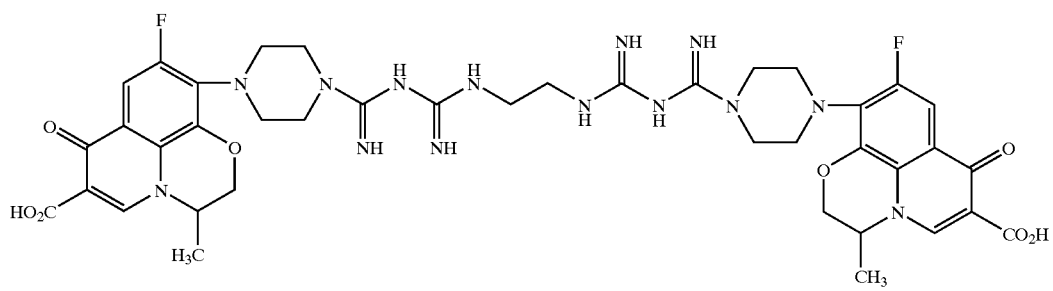
57.
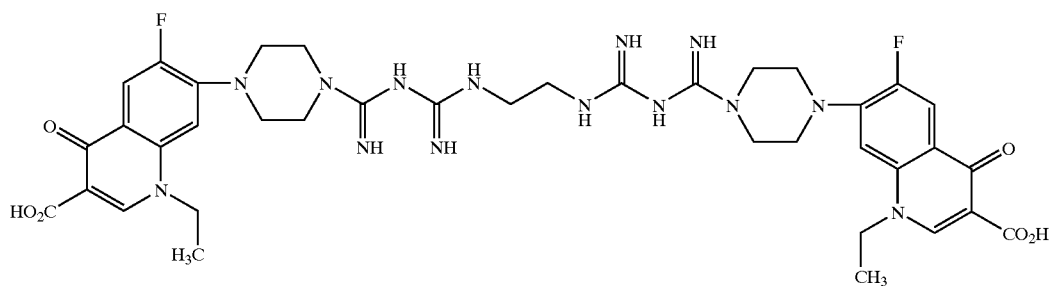
58.
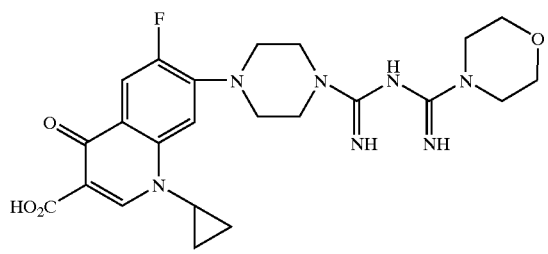
59.
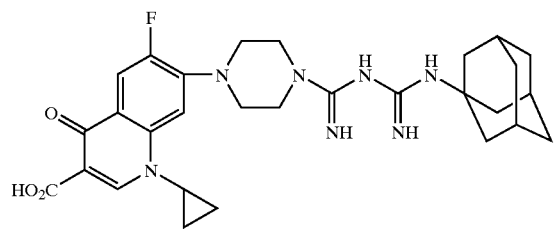

60.
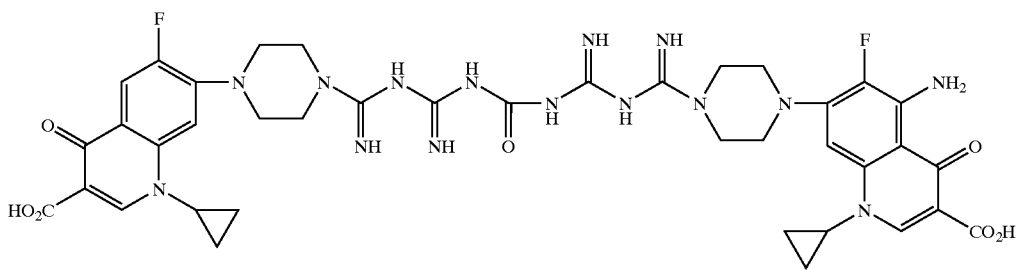
61.
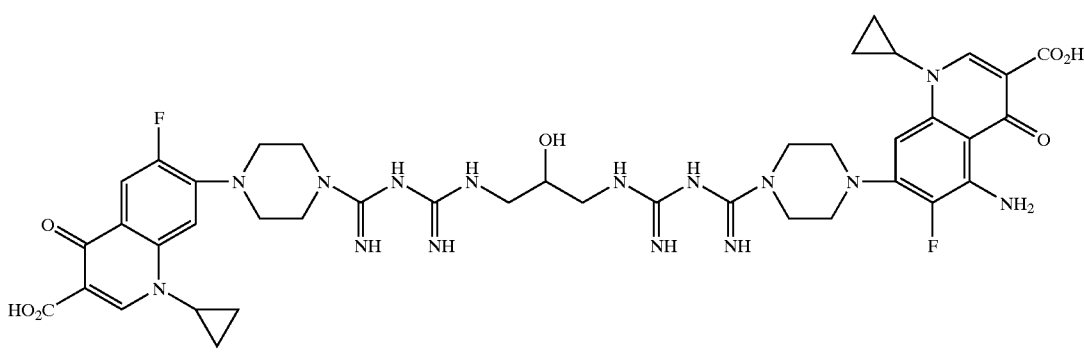
62.
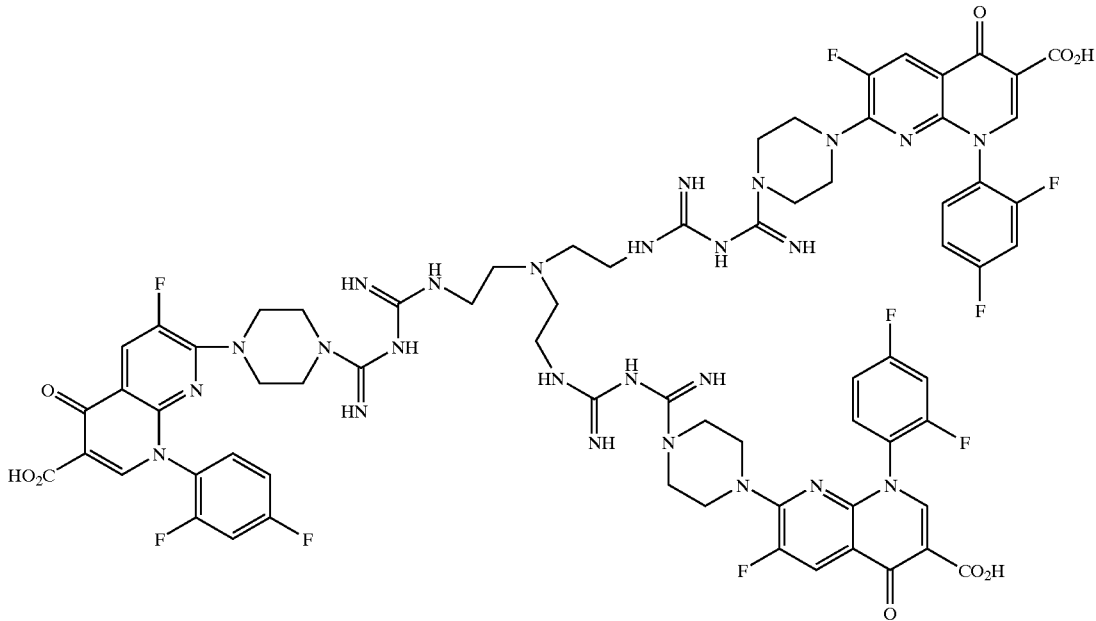
63.
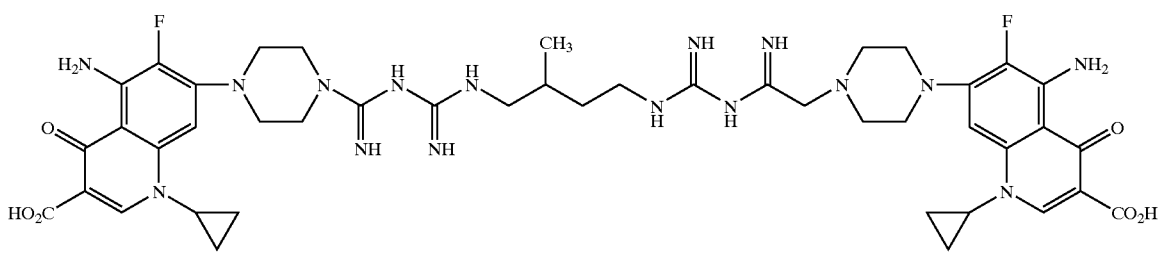

-continued
64.
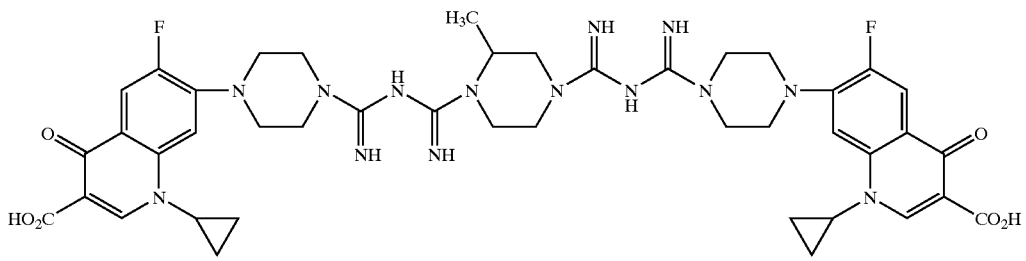
65.
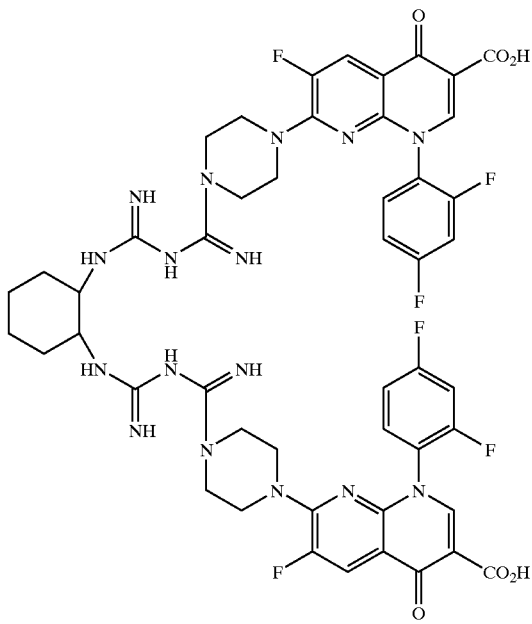
66.
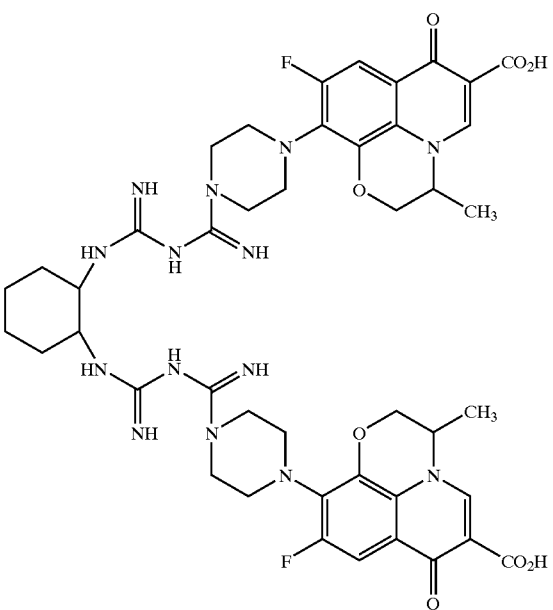
67.
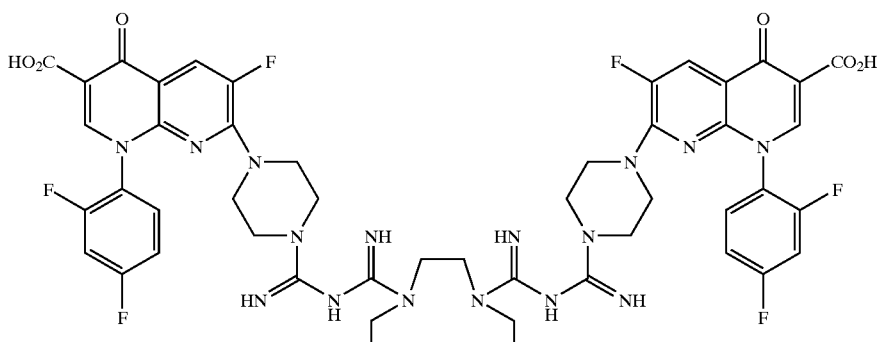

68.
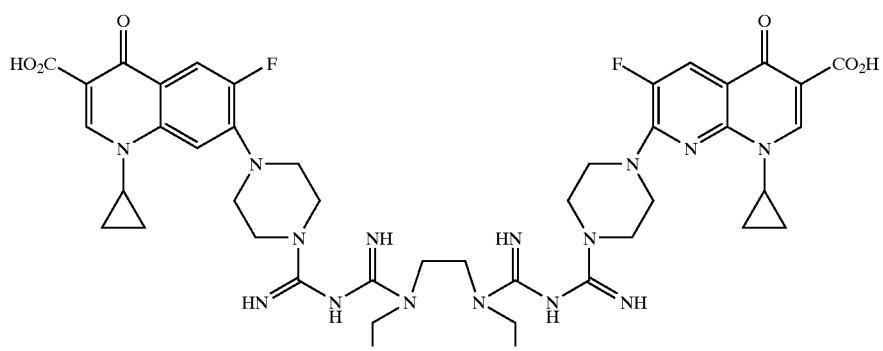
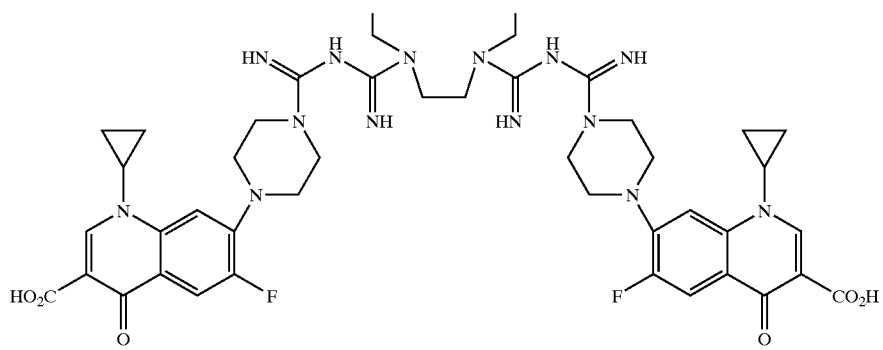
69.
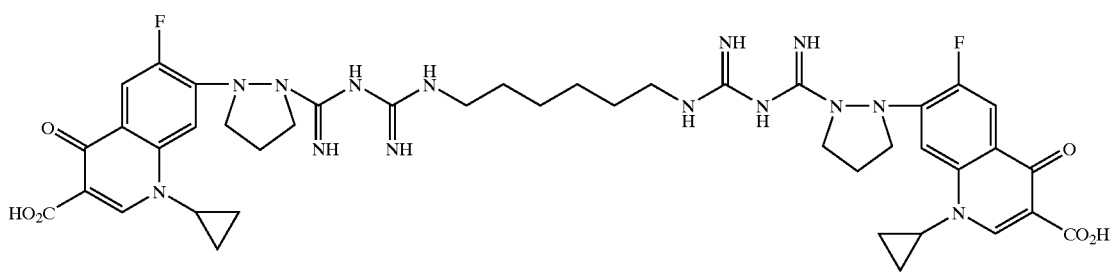
70.
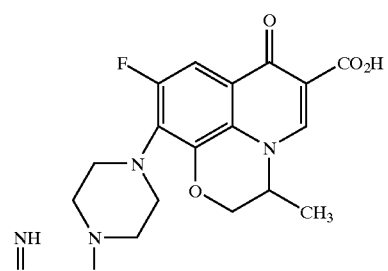

-continued
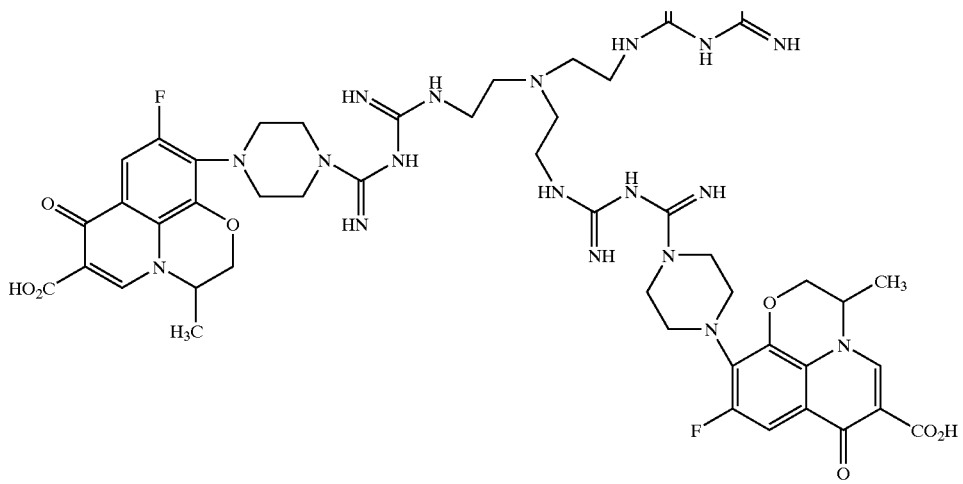
71.
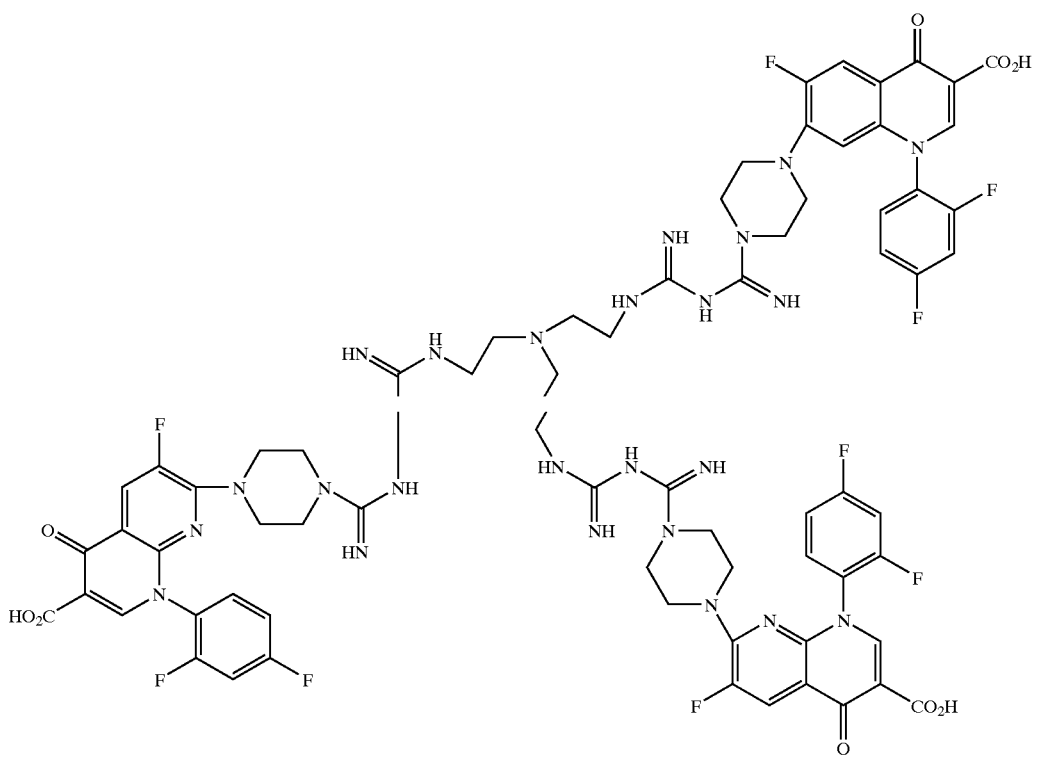
72.
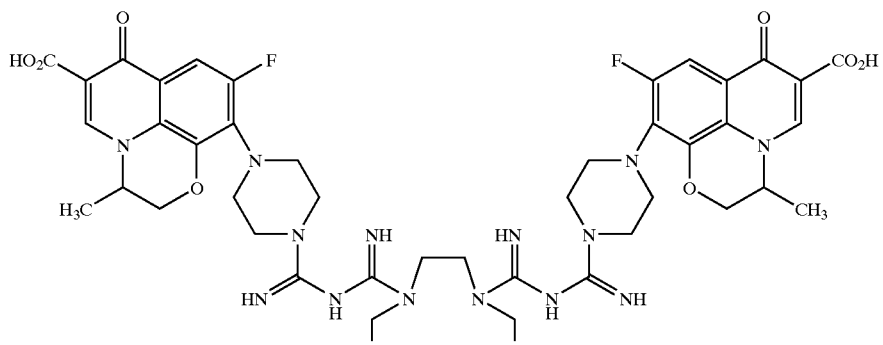

-continued
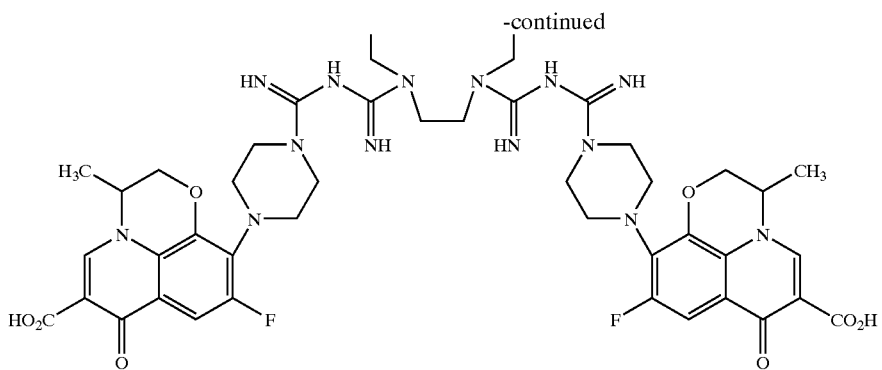
73.
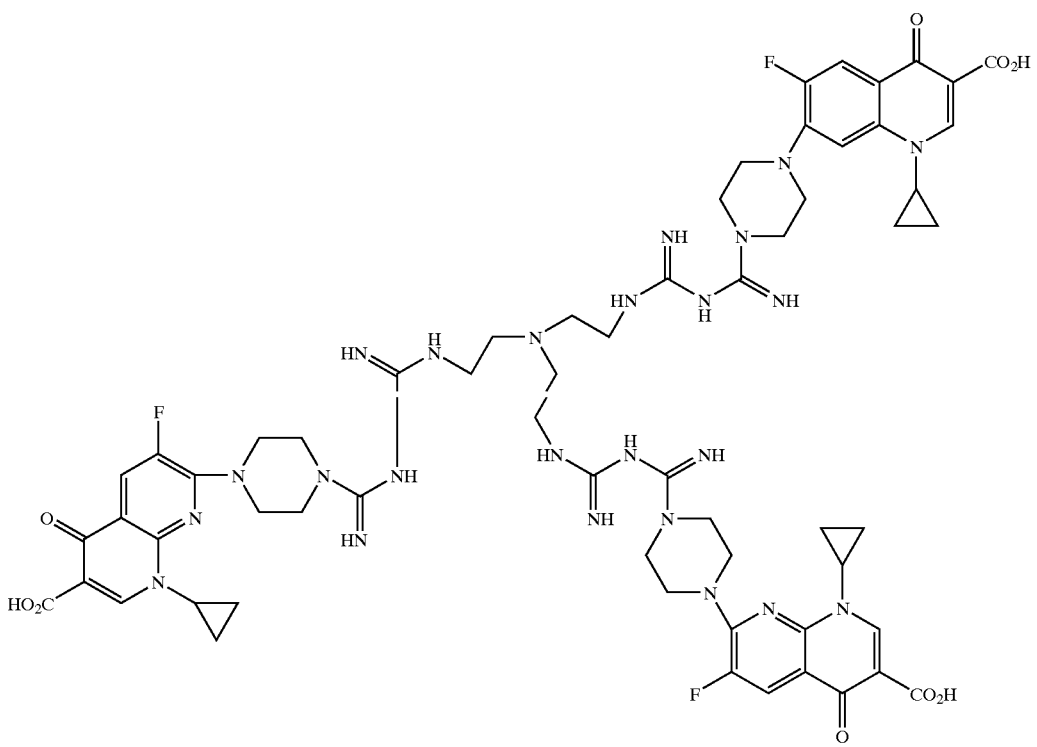
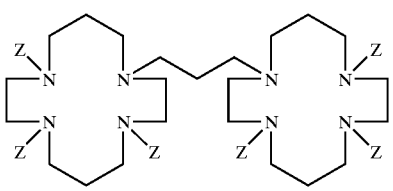
where each Z is:
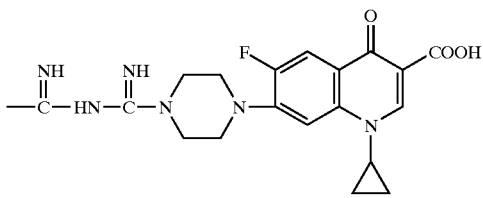
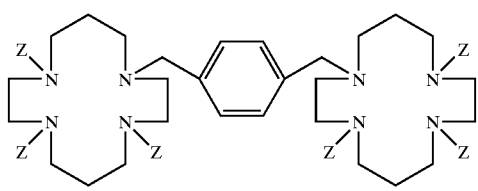
where each Z is:
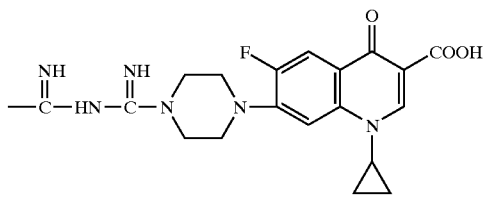

What is claimed is:
1. A compound having the following structure:
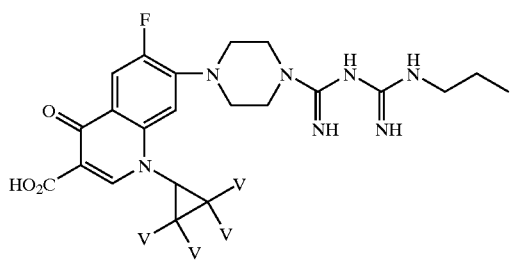
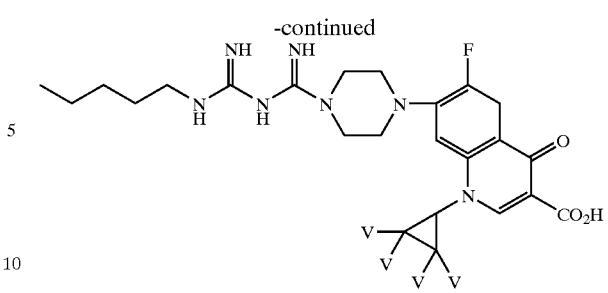
where each V is independently hydrogen or halogen.
2. A compound selected from the group consisting of:
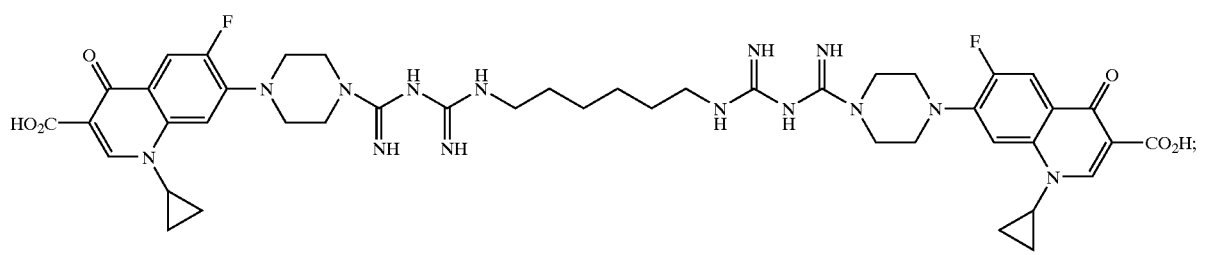
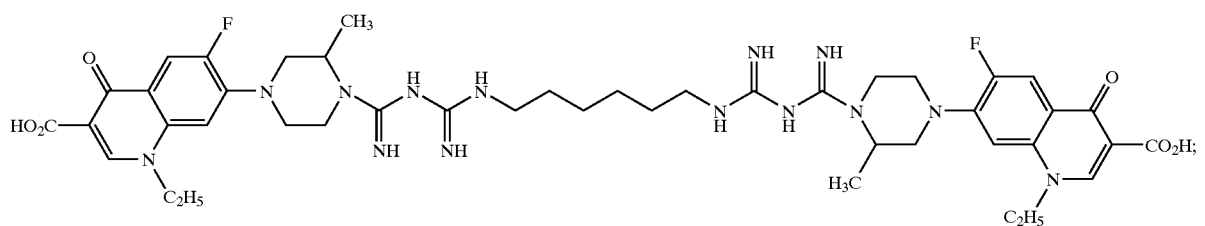
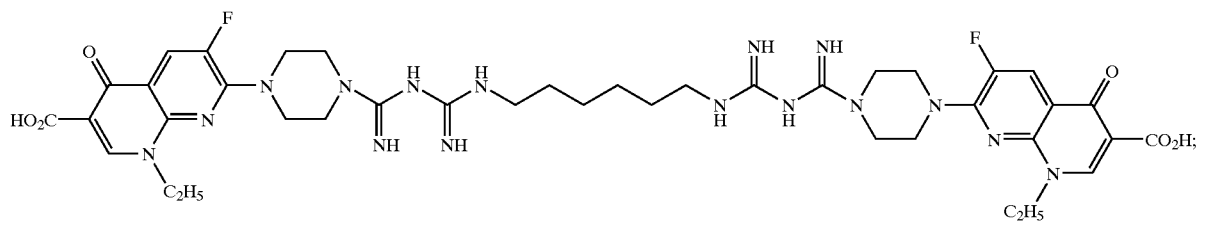
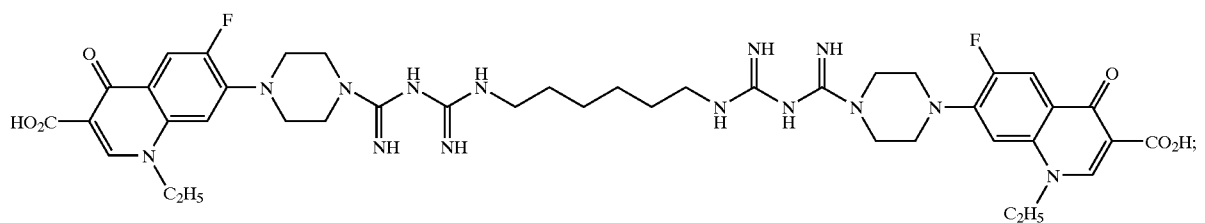
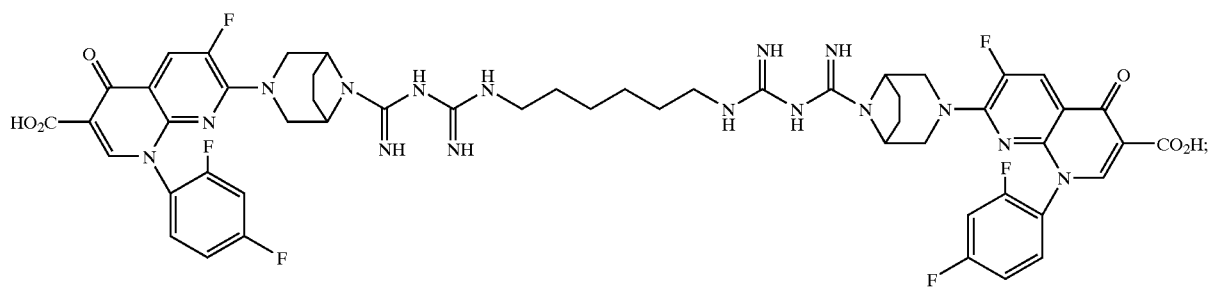

-continued
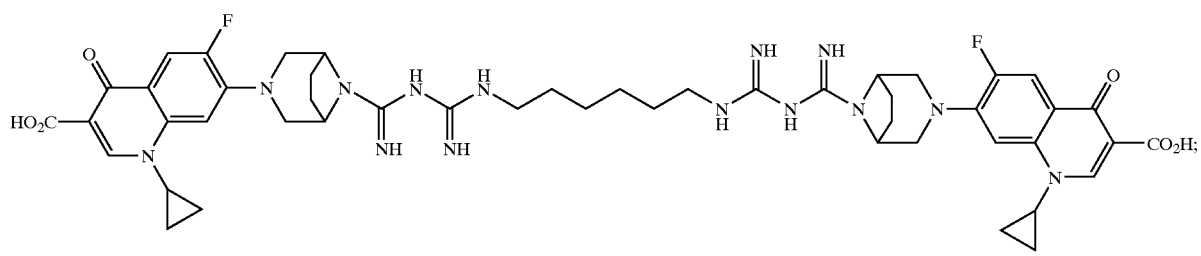
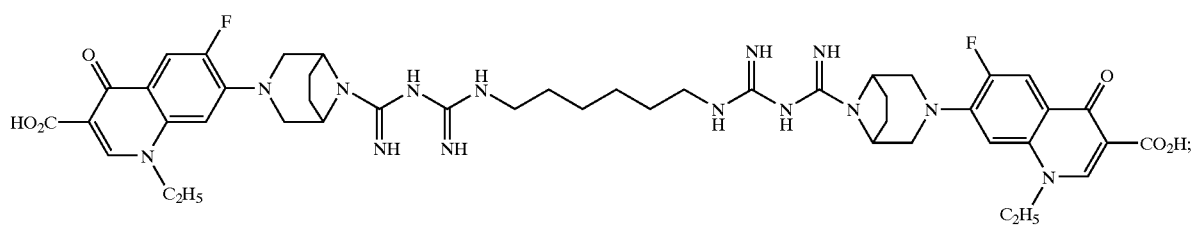
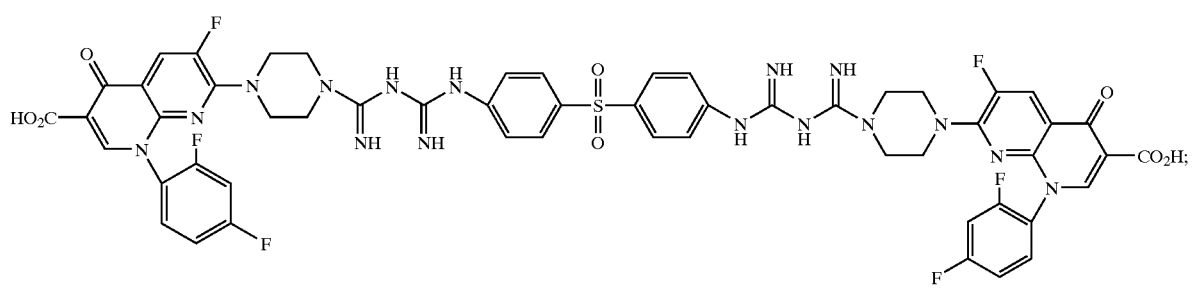
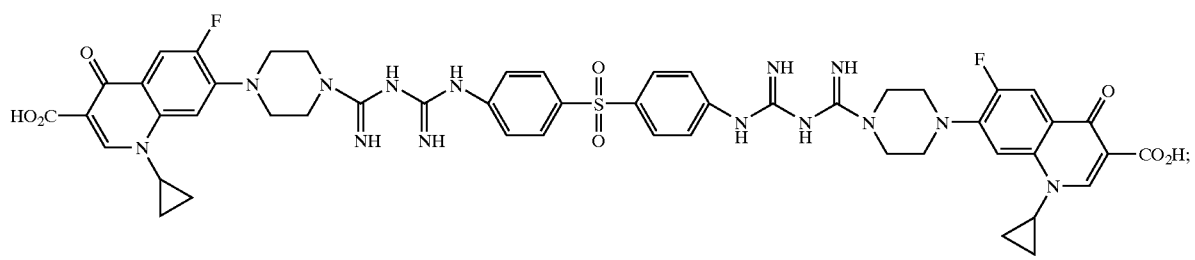
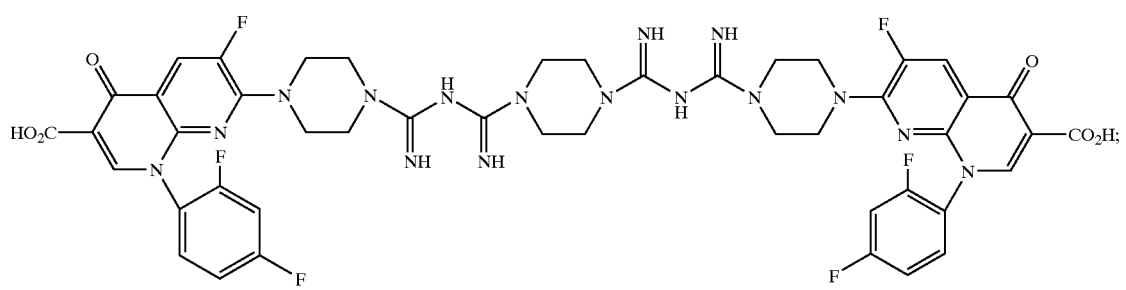
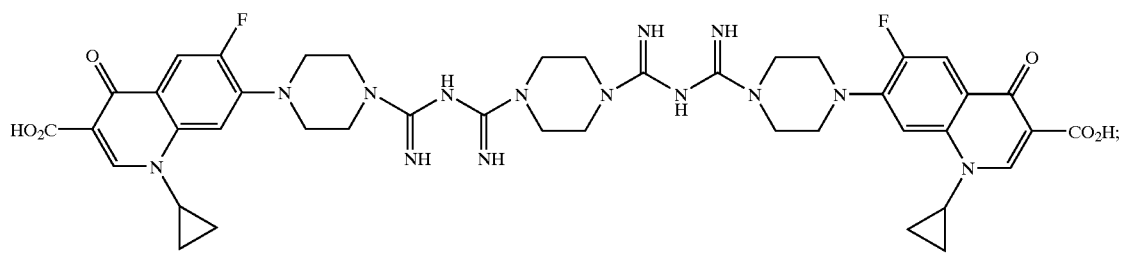

-continued
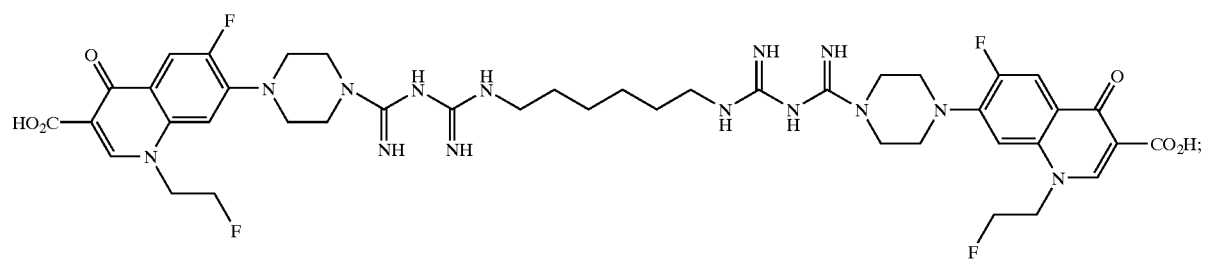
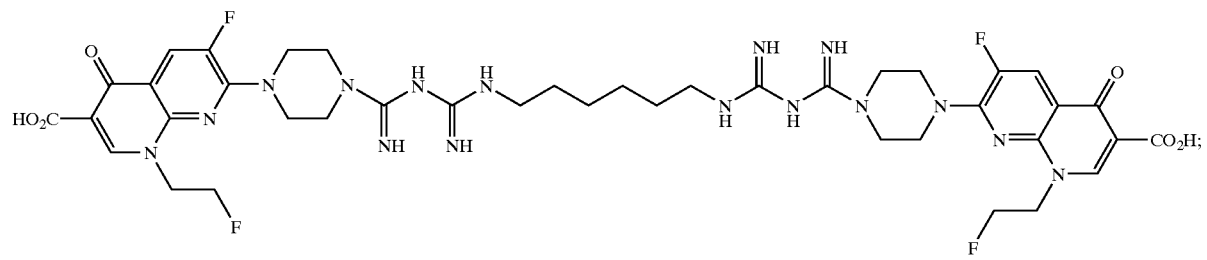
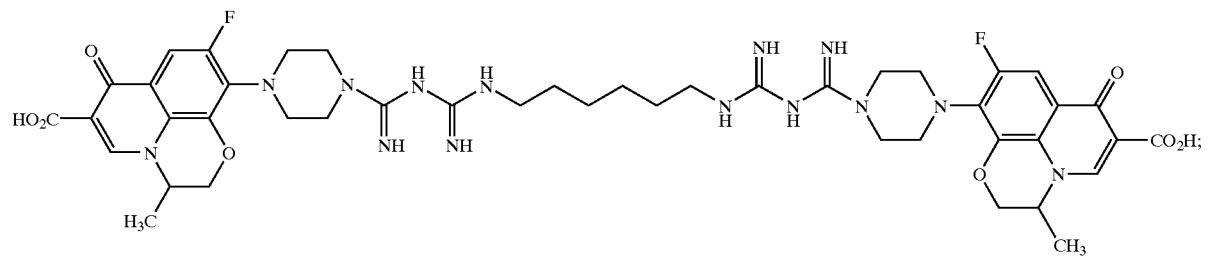
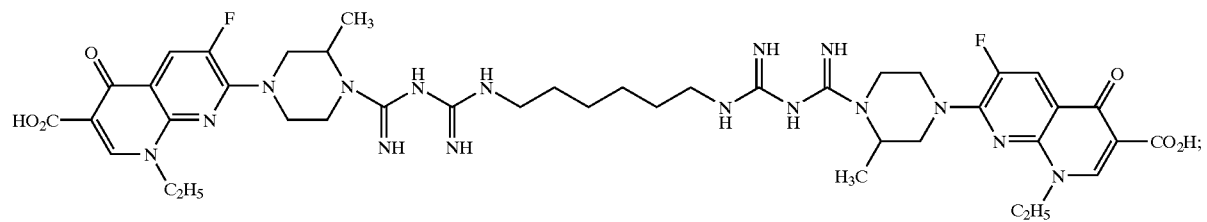
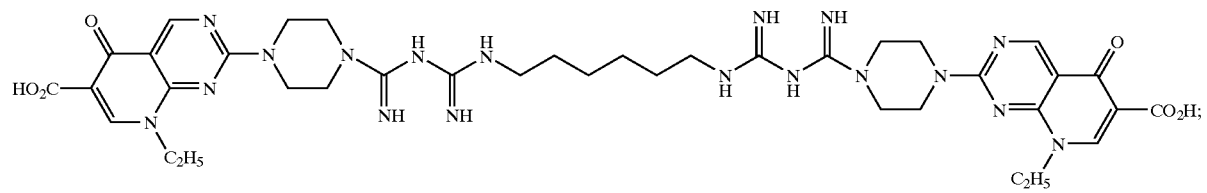
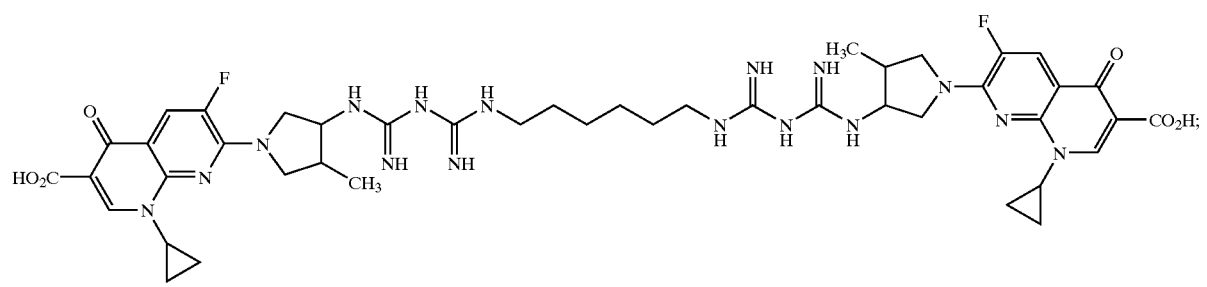

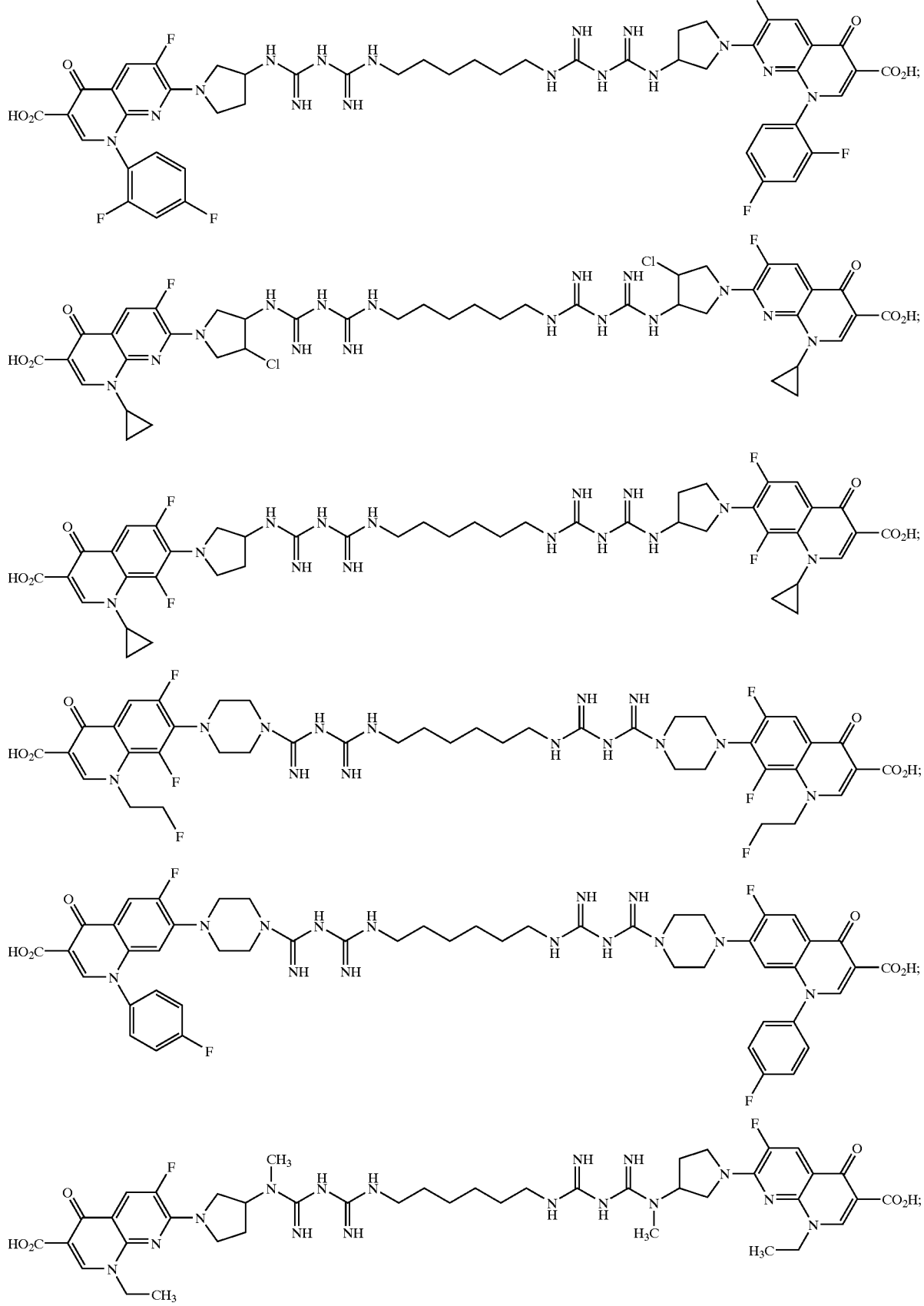

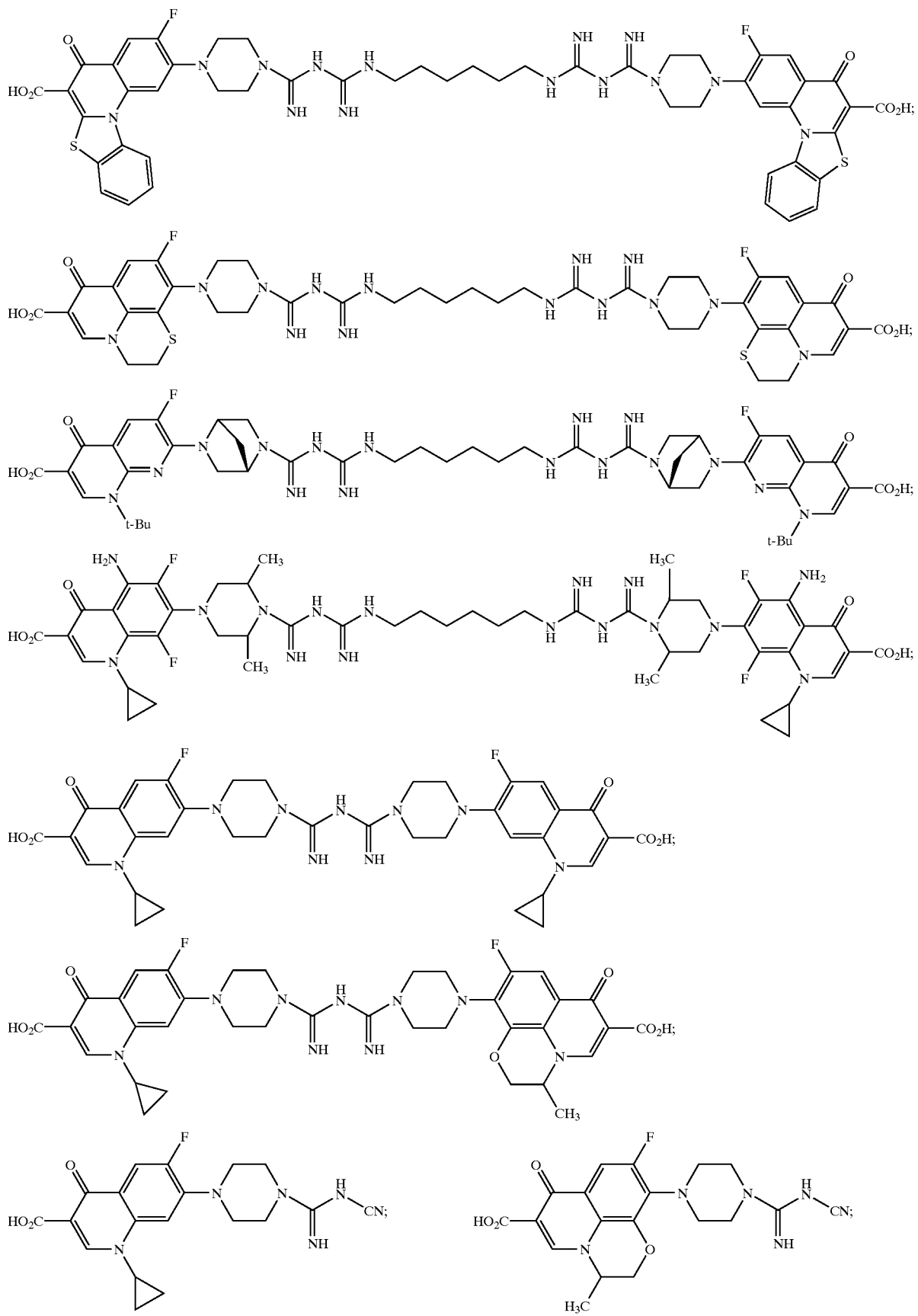
-continued

129
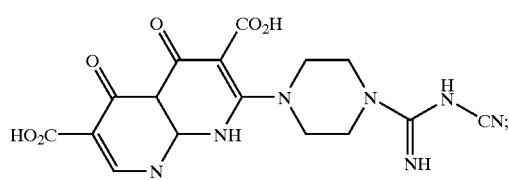
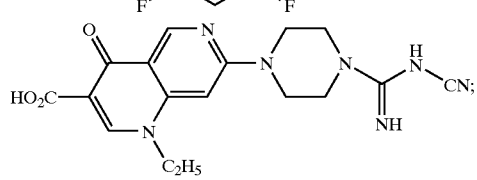
130
-continued
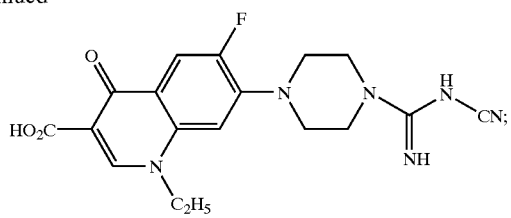
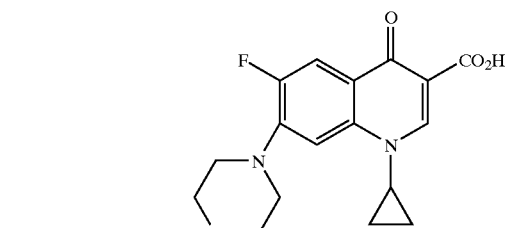
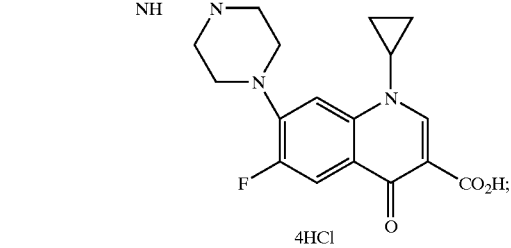
4HCl
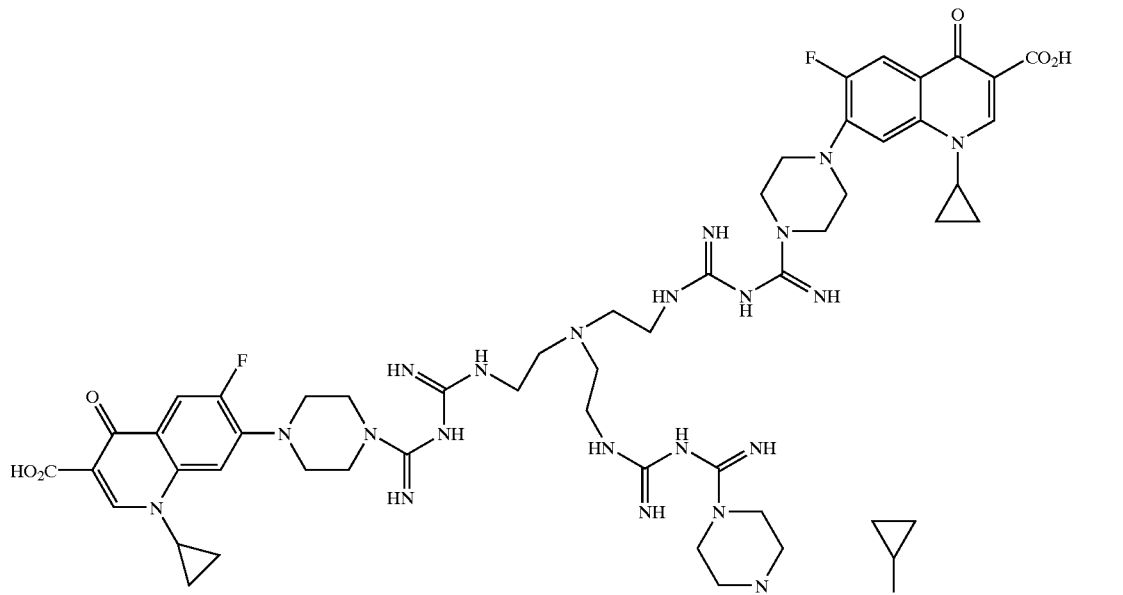

-continued
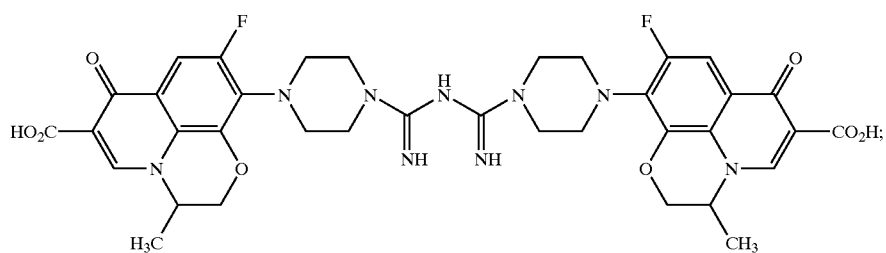
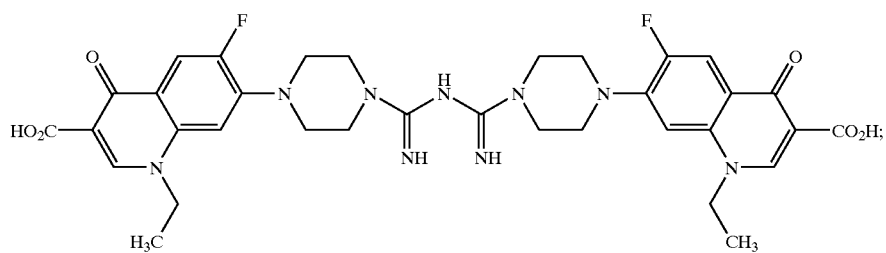
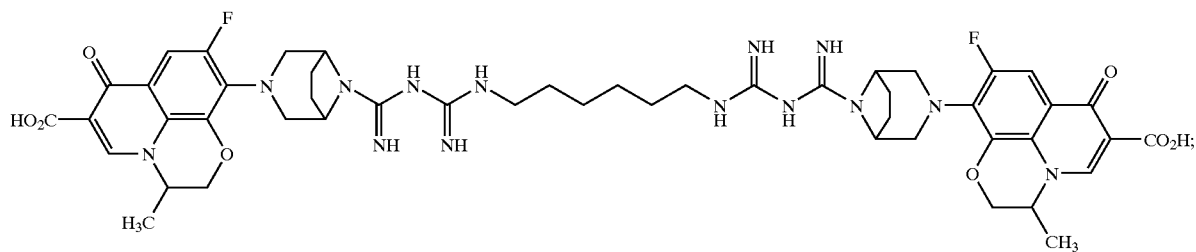
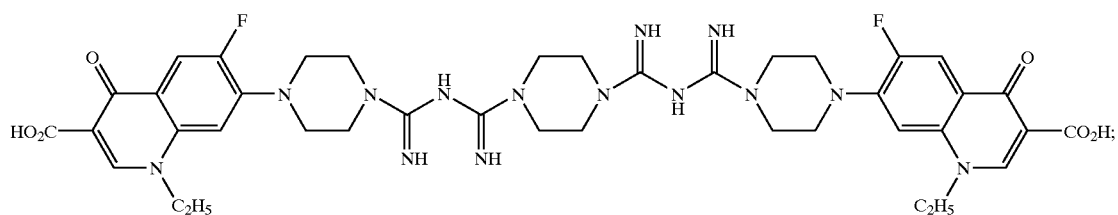
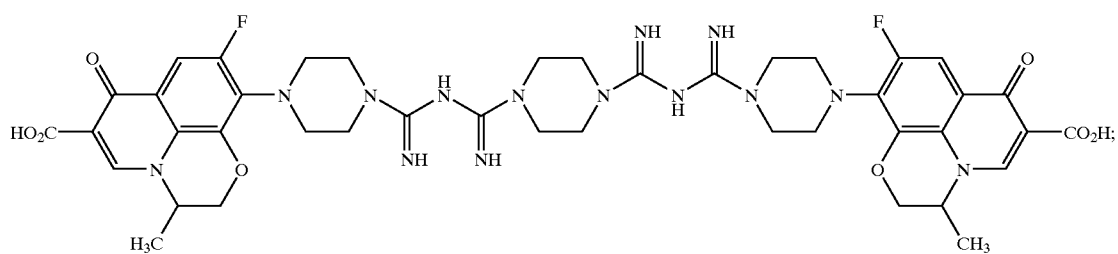
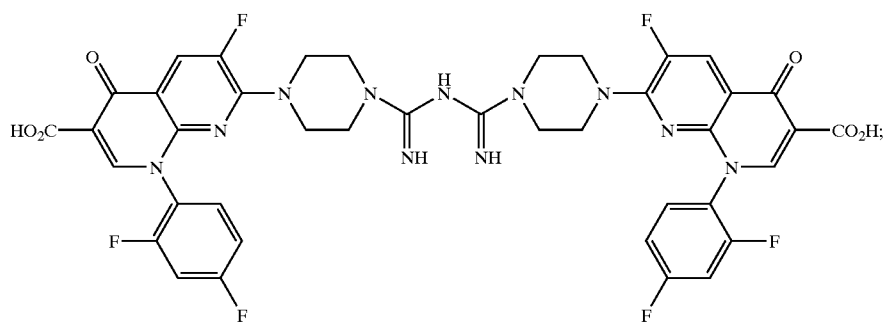

-continued
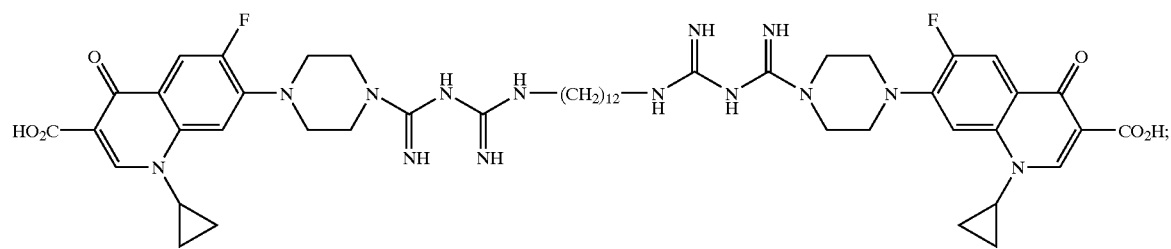
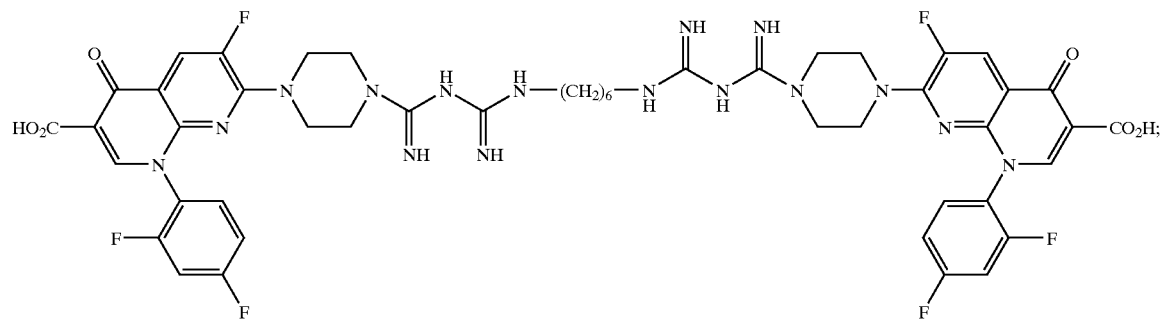
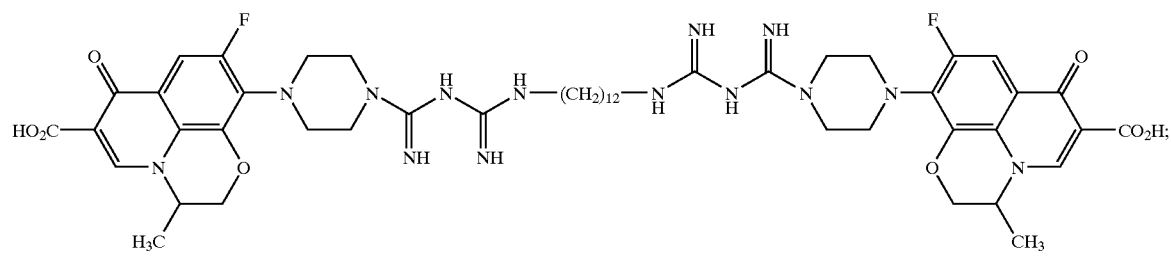
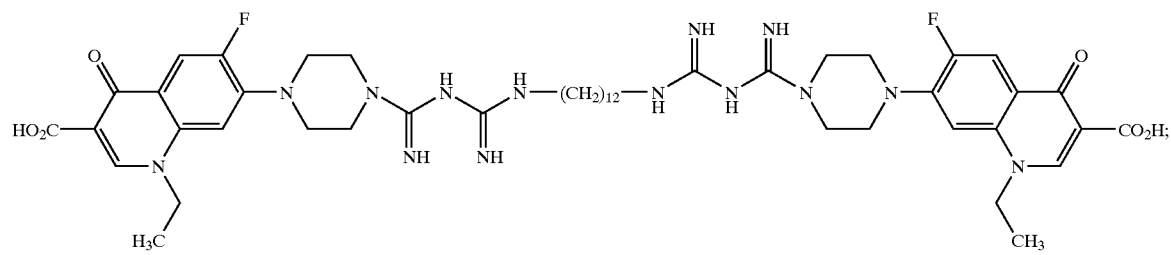
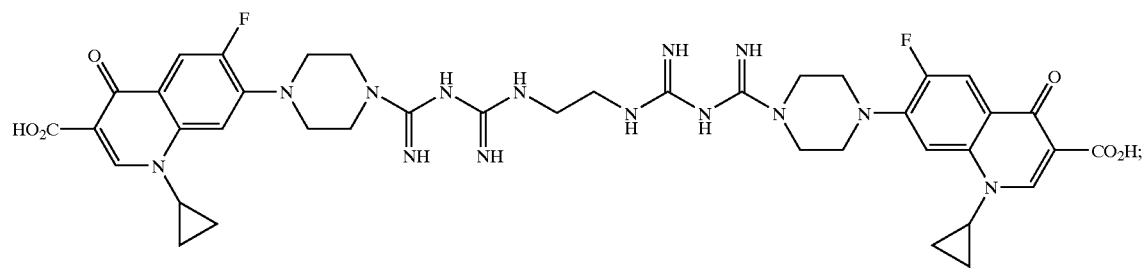
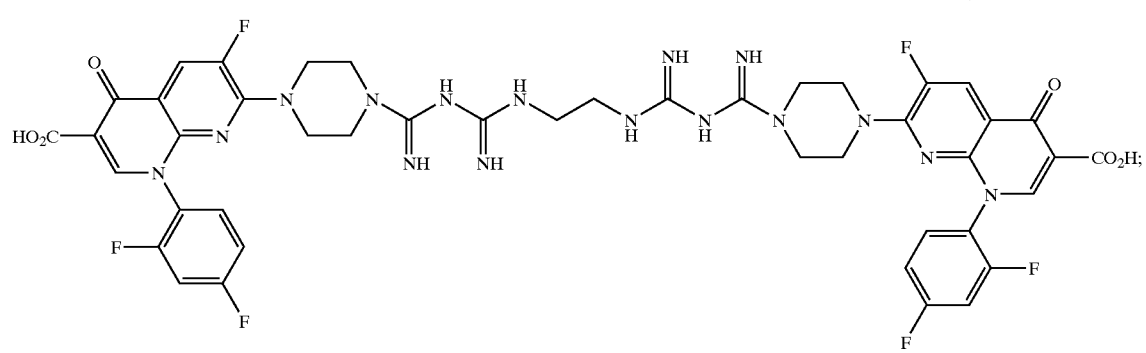

-continued
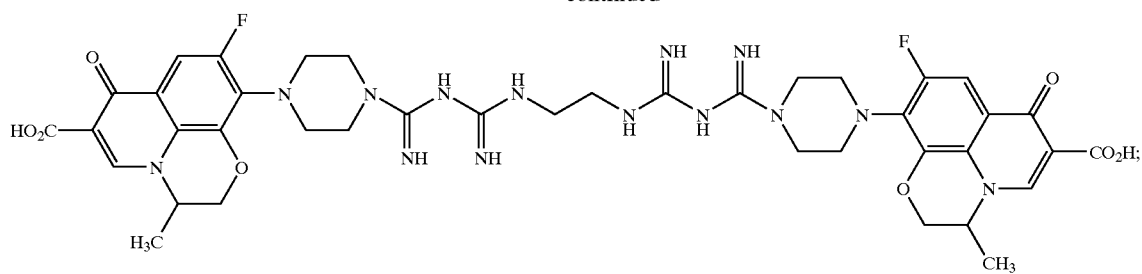
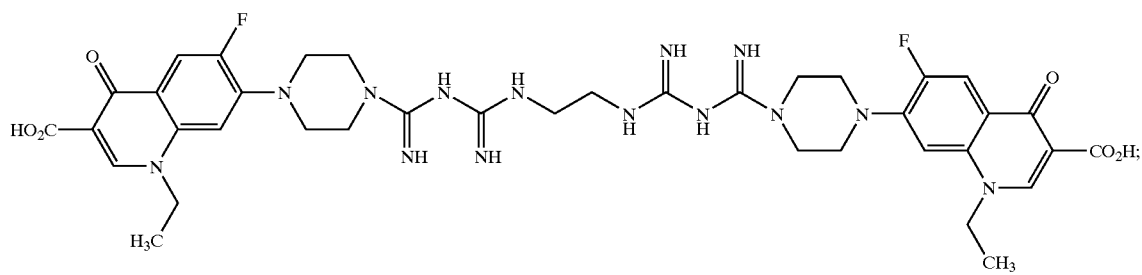
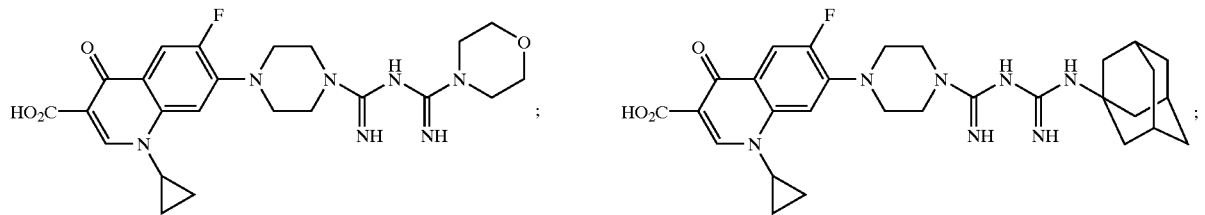
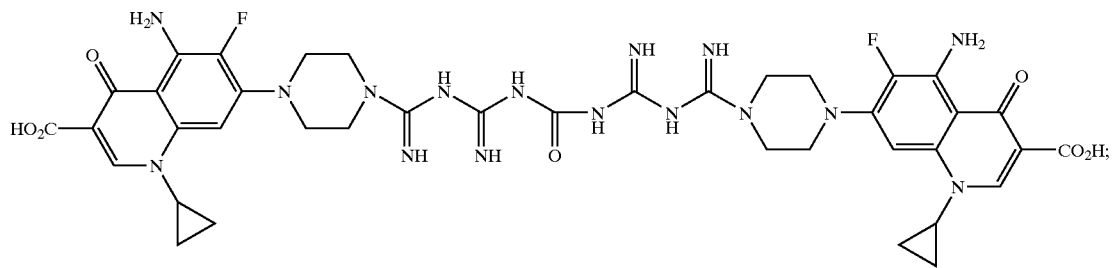
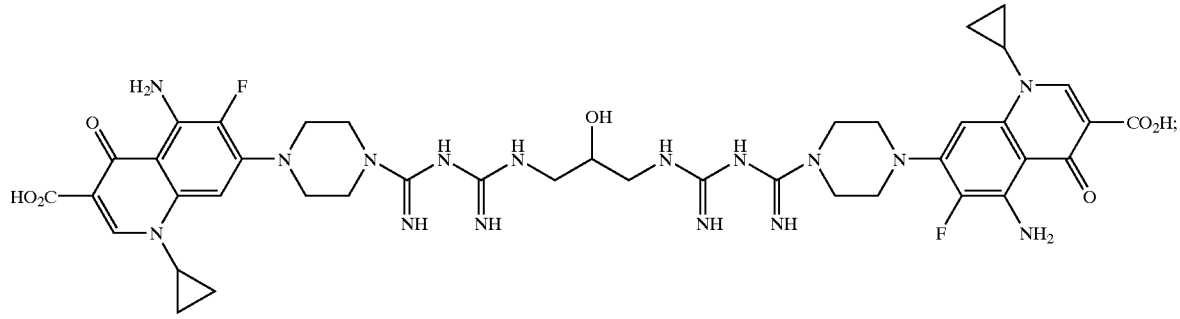
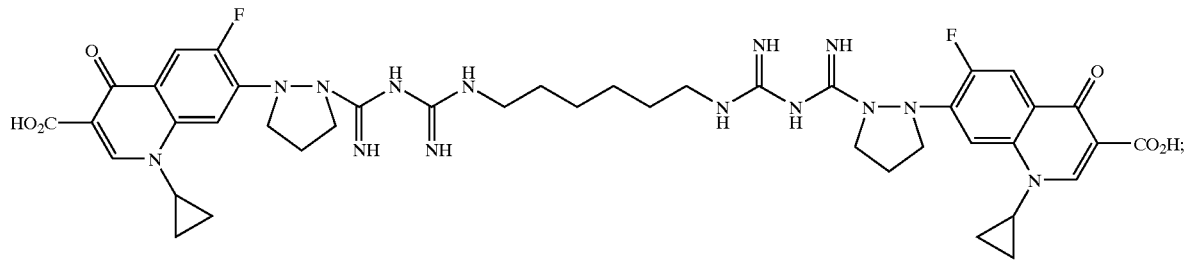

-continued
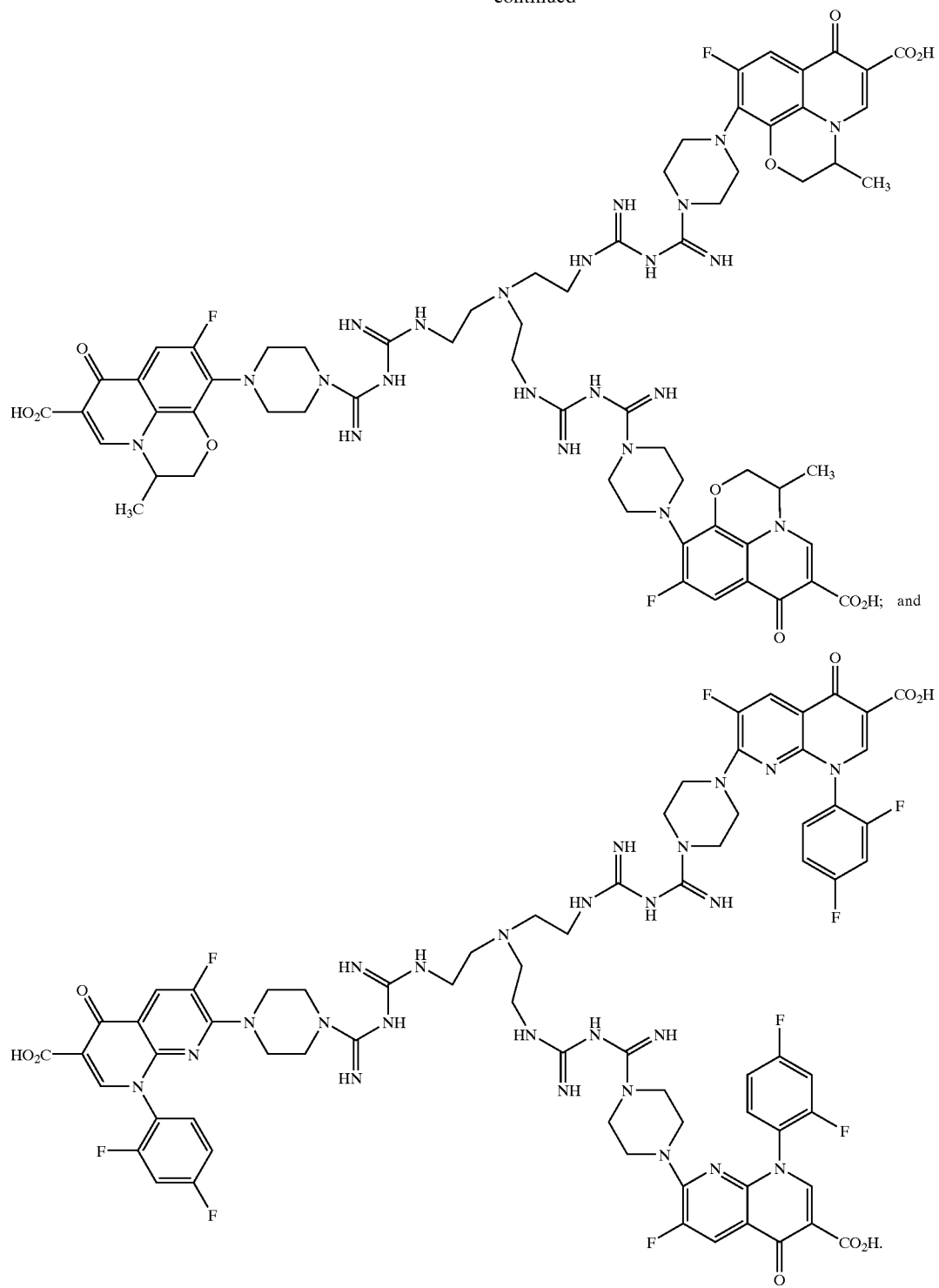
* * * * *